US012735421B2

(12) United States Patent
Yang et al.

(10) Patent No.: US 12,735,421 B2
(45) Date of Patent: Sep. 15, 2026

(54) PLASMIN INHIBITOR, PREPARATION METHOD THEREFOR, AND APPLICATION THEREOF

(71) Applicant: SCINNOHUB PHARMACEUTICAL CO., LTD, Chengdu (CN)

(72) Inventors: Anle Yang, Chengdu (CN); Sen Ji, Chengdu (CN); Zhi Wang, Chengdu (CN); Hao Wang, Chengdu (CN); Dewei Zhang, Chengdu (CN); Xiao Wang, Chengdu (CN); Huan Shen, Chengdu (CN); Jie Xiang, Chengdu (CN); Jialing Xian, Chengdu (CN); Yan Wang, Chengdu (CN); Xiao Hu, Chengdu (CN); Xiaodong Zhang, Chengdu (CN); Jun Tang, Chengdu (CN)

(73) Assignee: SCINNOHUB PHARMACEUTICAL CO., LTD, Chengdu (CN)

( * ) Notice: Subject to any disclaimer, the term of this patent is extended or adjusted under 35 U.S.C. 154(b) by 389 days.

(21) Appl. No.: 18/264,310

(22) PCT Filed: Jan. 28, 2022

(86) PCT No.: PCT/CN2022/074754
§ 371 (c)(1),
(2) Date: Aug. 4, 2023

(87) PCT Pub. No.: WO2022/166845
PCT Pub. Date: Aug. 11, 2022

(65) Prior Publication Data

US 2024/0124443 A1 Apr. 18, 2024

(30) Foreign Application Priority Data

Feb. 5, 2021 (CN) ........................ 202110163960.X

(51) Int. Cl.
*C07D 471/04* (2006.01)
*A61K 31/4375* (2006.01)
*A61P 7/04* (2006.01)
*C07D 491/20* (2006.01)

(52) U.S. Cl.
CPC .............. *C07D 471/04* (2013.01); *A61P 7/04* (2018.01); *C07D 491/20* (2013.01)

(58) Field of Classification Search
CPC ...... C07D 471/04; A61K 31/4375; A61P 7/04
USPC ........................................... 546/122; 514/300
See application file for complete search history.

(56) References Cited

U.S. PATENT DOCUMENTS

| | | | |
|---|---|---|---|
| 2007/0197564 | A1 | 8/2007 | Lavey et al. |
| 2012/0053201 | A1 | 3/2012 | Blackburn et al. |
| 2016/0280699 | A1 | 9/2016 | Röhn et al. |
| 2024/0300986 | A1 | 9/2024 | Yang et al. |

FOREIGN PATENT DOCUMENTS

| | | | |
|---|---|---|---|
| CN | 101115760 | A | 1/2008 |
| CN | 102459246 | A | 5/2012 |
| CN | 106458991 | A | 2/2017 |
| CN | 107108638 | A | 8/2017 |
| CN | 110684048 | A | 1/2020 |
| EP | 0 421 436 | A2 | 4/1991 |
| JP | 2001294572 | | 10/2001 |
| WO | WO 2007/002013 | A2 | 1/2007 |
| WO | WO 2008/149163 | A2 | 12/2008 |
| WO | WO 2012/047156 | A1 | 4/2012 |
| WO | 2013142328 | A1 | 9/2013 |
| WO | WO 2015/067549 | A1 | 5/2015 |
| WO | 2016071216 | A1 | 5/2016 |
| WO | 2018226998 | A1 | 12/2018 |
| WO | WO 2019/063015 | A1 | 4/2019 |
| WO | WO 2020/108538 | A1 | 6/2020 |

OTHER PUBLICATIONS

Healy, A.M. et al.: Pharmaceutical solvates, hydrates and amorphous forms. Adv. Drug Deli. Rev., vol. 117, pp. 25-46,2017.*
Kumar, R. et al.: Prodrugs: harnessing chemical modifications for improved therapeutics. J. of Drug Deliv. Sci. and Technol., vo. 90, p. 105103, 2023.*
Ng et al., "Tranexamic acid: a clinical review", *Anaesthesiol Intensive Ther.*, 47(4), pp. 339-350, (2015).
Tengborn et al., "Tranexamic acid—an old drug still going strong and making a revival", *Throb Res.*, 135(2), pp. 231-242, (2015).
Rumthao et al., "Design, Synthesis, and Evaluation of Oxyanion-hole Selective Inhibitor Substituents for the S1 Subsite of Factor Xa," Bioorg Med Chem Lett., vol. 14, No. 20, p. 5165-5170, (2004); Abstract Only.

* cited by examiner

*Primary Examiner* — Charanjit Aulakh
(74) *Attorney, Agent, or Firm* — Hoxie & Associates LLC

(57) ABSTRACT

The present invention relates to a compound of formula (I) capable of inhibiting plasmin activity and having blood coagulation and hemostasis activity, and a pharmaceutically acceptable salt, hydrate, isomer, prodrug and mixture thereof, wherein $R_1$ to $R_3$ are as defined in the description.

(I)

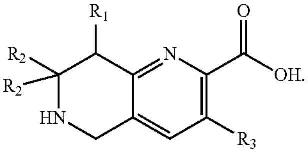

21 Claims, No Drawings

PLASMIN INHIBITOR, PREPARATION METHOD THEREFOR, AND APPLICATION THEREOF

CROSS-REFERENCE TO RELATED APPLICATIONS

The present application is a U.S. National Stage application under 35 U.S.C. § 371 of International Application No. PCT/CN2022/074754, filed on Jan. 28, 2022, which claims priority to Chinese patent application No. 202110163960.X, filed on Feb. 5, 2021, the contents of each of which are hereby incorporated by reference in their entireties.

TECHNICAL FIELD

The invention relates to the field of medicinal chemistry, in particular to a plasmin inhibitors, process of their preparation, and their use in medicine.

BACKGROUND

Plasmin is a proteolytic enzyme that degrades fibrin. When tissue damage causes vascular rupture, a hemostatic mechanism is triggered involving vasoconstriction, platelet plug formation, initiation of the coagulation process, and the final formation of stable fibrin. At the same time, due to fibrin deposition, the fibrinolytic system is activated, which maintains a balance between fibrin formation and lysis, and plays a role in maintaining vessel patency and remodeling damaged tissue during repair of damaged vessel walls (Tengborn L, Blomback M, Berntorp E. Thromb Res. 2015 February; 135(2):231-42).

The fibrinolytic system includes plasminogen, tissue plasminogen activator (tPA) and urokinase plasminogen activator (uPA). Plasminogen binds to lysine residues on the surface of fibrin and is converted to plasmin by an activator (i.e., tPA) released from endothelial cells. Fibrinolysis inhibition can be used to treat bleeding. The use of antifibrinolytic drugs can reduce blood loss in cardiac surgery, trauma, orthopedic surgery, solid organ transplantation, obstetrics and gynecology, neurosurgery and non-surgical conditions (Ng W, Jerath A, Wnsowicz M. Anaesthesiol Intensive Ther. 2015; 47(4):339-50). In the early 1950s, the amino acid lysine was found to inhibit the activation of plasminogen, but the effect was too weak to be useful in the treatment of fibrinolytic hemorrhagic diseases. In 1953, Shosuke Okamoto and others showed that several sulfhydryl- and amino-carboxylic acids had anti-plasma protein effects, and found that c-aminocaproic acid (EACA), a synthetic derivative of lysine, had a strong inhibitory effect on plasminogen. EACA has been widely used clinically, but requires a large dose and is accompanied by mild gastrointestinal side effects such as nausea. In 1962, 4-aminomethyl-cyclohexane-carboxylic acid (AMCHA) was discovered. This compound contains two stereoisomers, and further studies showed that its trans form (trans-4-aminomethyl-cyclohexane-carboxylic acid, i.e., tranexamic acid, TXA) has anti-fibrinolytic activity about 10 times that of EACA, and has been shown to be more tolerated (Tengborn L, Blomback M, Berntorp E. Thromb Res. 2015 February; 135(2):231-42).

Tranexamic acid is a synthetic lysine derivative and antifibrinolytic agent that forms a reversible complex with plasminogen. By binding to plasminogen, interaction of plasminogen and plasmin heavy chain with fibrin lysine residue is blocked, thereby preventing binding of plasminogen to fibrin surface and delaying fibrinolysis. Tranexamic acid has been approved for the treatment of severe menstrual bleeding and various surgical bleeding disorders, and is currently the most commonly used hemostatic drug in clinical practice. However, a large number of literature reports show that tranexamic acid is prone to gastrointestinal adverse reactions after oral administration, such as nausea, vomiting, diarrhea and dyspepsia, and its dosage is relatively high, which may cause complications such as epilepsy in patients.

Other similar hemostatic drugs, such as aminocaproic acid, have the problems of rapid excretion in human body, weak hemostatic effect, short duration of action, many toxic reactions and the like, and can form thrombus when the dosage is too high, thereby limiting the application to patients with thrombosis tendency or thrombotic vascular diseases and renal insufficiency. The mechanism of aminomethylbenzoic acid is the same as that of aminocaproic acid, and its effect is 4 to 5 times stronger than that of aminocaproic acid. It has a significant effect on common chronic bleeding, but has no hemostatic effect on traumatic bleeding and cancer bleeding. In addition, excessive dosage can also promote thrombosis. Aprotinin, a commonly used hemostatic drug in bypass surgery, was also withdrawn from the market by the FDA in 2008 because it can induce renal failure, myocardial infarction, heart failure, and the like.

Hemostatic drugs with other mechanisms, such as carbacola, which acts on blood vessels, can induce epilepsy after repeated use; the thrombin, a hemostatic drug which promotes the blood coagulation process, can be applied to gastrointestinal bleeding or local bleeding only.

In view of the fact that the choice of clinically available hemostatic drugs is very limited, certain defects exist in the aspects of dosage, clinical indications and the like, and the existing drugs of the same type have the problems of large dosages, many adverse reactions, and are prone to complications such as epilepsy, it is necessary to develop a new hemostatic drug to better meet the clinical needs.

DISCLOSURE OF INVENTION

In a first aspect, the invention aims to overcome the above-mentioned drawbacks of the prior art and to provide a novel compound having blood coagulation and hemostasis activity.

In particular, the invention provides a compound represented by the structure of formula I, a pharmaceutically acceptable salt, hydrate, isomer, prodrug and mixture thereof:

Formula I

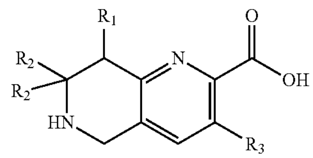

wherein $R_1$ is selected from the group consisting of hydrogen, hydroxy, amino, alkyl, alkoxy, —NH-alkyl, cycloalkyl, aryl, aliphatic heterocyclyl, and aromatic heterocyclyl; wherein said $R_1$ is optionally substituted with 1-2 groups selected from hydroxy, alkyl, arylalkyl, halogen, aryl, cycloalkyl;

$R_2$ is independently selected from the group consisting of hydrogen, carboxyl, amido, alkyl, —NH-alkyl, —$CH_2$O-alkyl, —$CH_2$NH-alkyl, —COO-alkyl, —CONH-alkyl, cycloalkyl, aryl, aliphatic heterocyclyl, aromatic heterocyclyl, arylalkyl, cycloalkylalkyl; wherein said $R_2$ is optionally substituted with 1-2 groups selected from hydroxy, alkyl, alkoxy; or two $R_2$ together with the carbon atom to which they are attached form a cycloalkyl, aliphatic heterocyclyl;

$R_3$ is selected from hydrogen and halogen, and specifically, $R_3$ is selected from hydrogen, fluorine, chlorine and bromine.

In one embodiment, the present invention provides a compound represented by the structure of formula I', a pharmaceutically acceptable salt, hydrate, isomer, prodrug and mixture thereof:

Formula I'

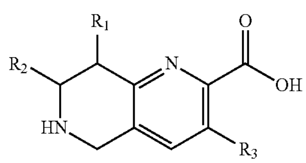

wherein $R_1$ is selected from the group consisting of hydrogen, hydroxy, amino, alkyl, alkoxy, —NH-alkyl, cycloalkyl, aryl, aliphatic heterocyclyl, and aromatic heterocyclyl; wherein said $R_1$ is optionally substituted with 1-2 groups selected from hydroxy, alkyl, halogen, aryl, cycloalkyl;

$R_2$ is selected from the group consisting of hydrogen, carboxyl, amido, alkyl, —NH-alkyl, —$CH_2$O-alkyl, —$CH_2$NH-alkyl, —COO-alkyl, —CONH-alkyl, cycloalkyl, aryl, aliphatic heterocyclyl, and aromatic heterocyclyl; wherein said $R_2$ is optionally substituted with 1-2 groups selected from hydroxy, alkyl;

$R_3$ is selected from hydrogen and halogen, and specifically, $R_3$ is selected from hydrogen, fluorine, chlorine and bromine.

In certain embodiments, $R_1$ is selected from the group consisting of hydrogen, hydroxy, amino, $C_1$-$C_6$ alkyl, $C_1$-$C_6$ alkoxy, —NH-($C_1$-$C_6$) alkyl, $C_3$-$C_6$cycloalkyl, 6- to 10-membered aryl, 4- to 10-membered aliphatic heterocyclyl, 5- to 10-membered aromatic heterocyclyl; wherein said $R_1$ is optionally substituted with 1-2 groups selected from hydroxy, $C_1$-$C_4$ alkyl, halogen, 6- to 10-membered aryl or aromatic heterocyclyl, $C_3$-$C_6$ cycloalkyl.

In certain embodiments, $R_1$ is selected from the group consisting of hydrogen, hydroxy, amino, phenyl, pyridyl, $C_1$-$C_6$ alkyl, $C_1$-$C_6$ alkoxy, —NH-($C_1$-$C_6$) alkyl, $C_3$-$C_6$cycloalkyl, 4- to 7-membered aliphatic heterocyclyl; wherein said $R_1$ is optionally substituted with 1-2 groups selected from hydroxy, $C_1$-$C_4$ alkyl, F, Cl, Br, phenyl, benzyl, cyclopropyl.

In certain embodiments, $R_1$ is selected from the group consisting of hydrogen, hydroxy, amino, phenyl, benzyl, pyridyl, methyl, ethyl, propyl, isopropyl, butyl, methoxy, ethoxy, propoxy, —$NHCH_3$, —$NHCH_2CH_3$, —$NHCH_2CH_2CH_3$, cyclopropyl, cyclobutyl, cyclopentyl, piperidinyl, morpholinyl, piperazinyl, thiomorpholinyl, 1-oxido-4-thiomorpholinyl, 1,1-dioxido-4-thiomorpholinyl; wherein said $R_1$ is optionally substituted with 1-2 groups selected from hydroxy, F, Cl, Br, methyl, ethyl, propyl, isopropyl, phenyl, benzyl, cyclopropyl.

In certain embodiments, $R_1$ is selected from the group consisting of hydrogen, $C_1$-$C_4$ alkoxy, morpholinyl, piperazinyl, thiomorpholinyl, 1-oxido-4-thiomorpholinyl, and 1,1-dioxido-4-thiomorpholinyl, wherein said $R_1$ is optionally substituted with 1-2 groups selected from hydroxy and benzyl.

In certain embodiments, $R_2$ is selected from the group consisting of hydrogen, carboxyl, amido, $C_1$-$C_6$ alkyl, —$CH_2$O-($C_1$-$C_6$) alkyl, —$CH_2$NH-($C_1$-$C_6$) alkyl, —COO ($C_1$-$C_6$) alkyl, —CONH-($C_1$-$C_6$) alkyl, $C_3$-$C_8$ cycloalkyl, 6- to 10-membered aryl, 4- to 10-membered aliphatic heterocyclyl, 5- to 10-membered aromatic heterocyclyl; wherein said $R_2$ is optionally substituted with 1-2 groups selected from hydroxy, $C_1$-$C_4$ alkyl;

In certain embodiments, $R_2$ is selected from the group consisting of hydrogen, carboxyl, amido, $C_1$-$C_6$ alkyl, —$CH_2$O-($C_1$-$C_6$) alkyl, —$CH_2$NH-($C_1$-$C_6$) alkyl, —COO-($C_1$-$C_6$) alkyl, —CONH-($C_1$-$C_6$) alkyl, $C_3$-$C_6$ cycloalkyl, 6-membered aryl, 4- to 7-membered aliphatic heterocyclyl, 6-membered aromatic heterocyclyl; wherein said $R_2$ is optionally substituted with 1-2 groups selected from hydroxy, $C_1$-$C_4$alkyl;

In certain embodiments, $R_2$ is selected from the group consisting of hydrogen, carboxyl, amido, methyl, ethyl, propyl, isopropyl, n-butyl, t-butyl, pentyl, —$CH_2OCH_3$, —$CH_2OCH_2CH_3$, —$CH_2OCH_2CH_2CH_3$, —$CH_2NHCH_3$, —$CH_2NHCH_2CH_3$, —$CH_2NHCH_2CH_2CH_3$, —$COOCH_3$, —$COOCH_2CH_3$, —$COOCH_2CH_2CH_3$, —$CONHCH_3$, —$CONHCH_2CH_3$, —$CONHCH_2CH_2CH_3$, cyclopropyl, cyclobutyl, cyclopentyl, cyclohexyl, phenyl, benzyl, pyridyl, piperidinyl, morpholinyl, thiomorpholinyl, 1-oxido-thiomorpholinyl, 1,1-dioxido-4-thiomorpholinyl; wherein said $R_2$ is optionally substituted with 1-2 groups selected from hydroxy, methyl, ethyl, propyl, isopropyl.

In certain embodiments, $R_2$ is independently selected from the group consisting of hydrogen, carboxyl, $C_1$-$C_6$ alkyl, —$CH_2$O-($C_1$-$C_6$) alkyl, —COO-($C_1$-$C_6$) alkyl, $C_3$-$C_6$ cycloalkyl, phenyl-($C_1$-$C_4$) alkyl and ($C_3$-$C_6$) cycloalkyl-($C_1$-$C_4$) alkyl, wherein said alkyl, cycloalkyl and phenyl are optionally substituted with 1-2 groups selected from hydroxy and $C_1$-$C_4$ alkoxy; or two $R_2$ together with the carbon atom to which they are attached form a $C_3$-$C_6$ cycloalkyl or tetrahydropyranyl.

In certain embodiments, one of $R_2$ is hydrogen. In certain embodiments, $R_3$ is selected from hydrogen and fluorine.

In certain embodiments, $R_1$ and $R_2$ are not hydrogen simultaneously;

In certain embodiments, $R_1$, $R_2$ and $R_3$ are not hydrogen simultaneously.

In certain embodiments, the compounds of formula I of the present invention have the following structure:

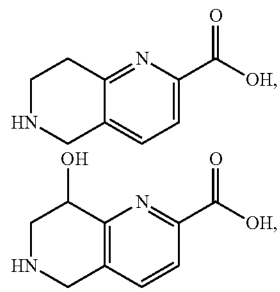

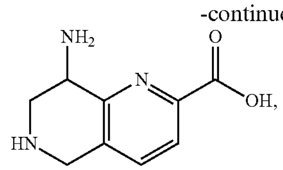
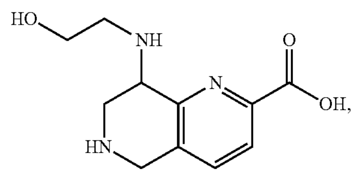
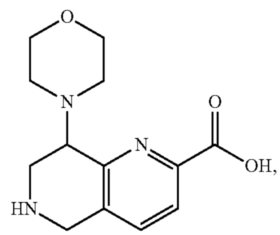
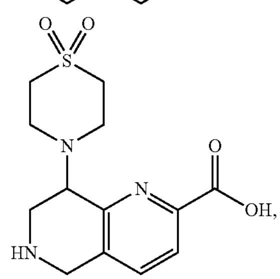
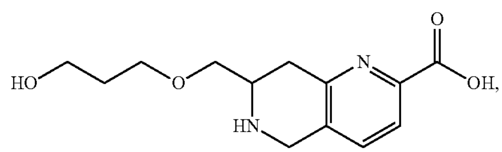
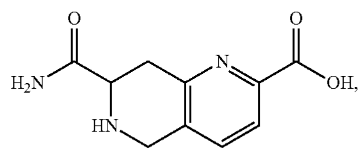
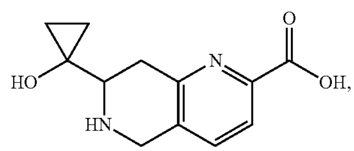
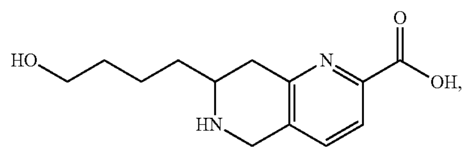
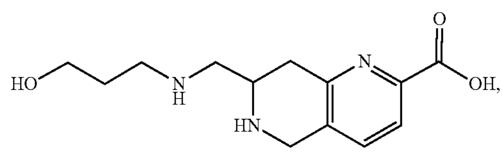
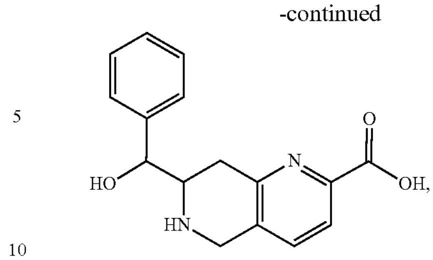
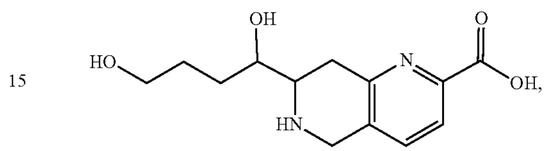
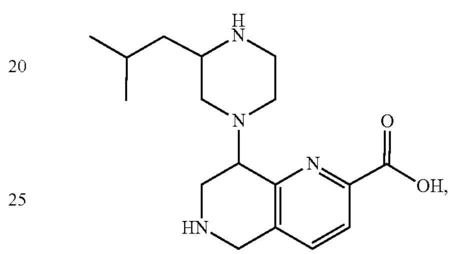
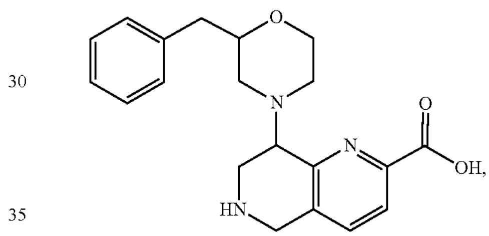
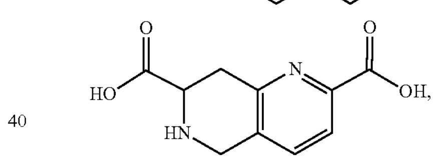
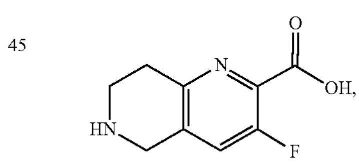
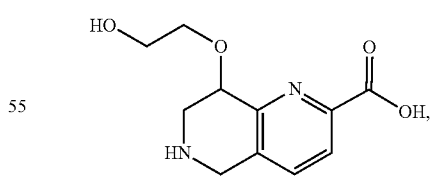
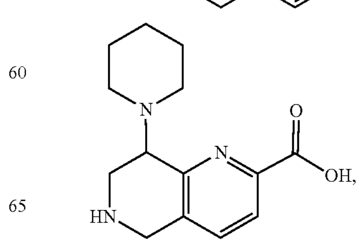

-continued
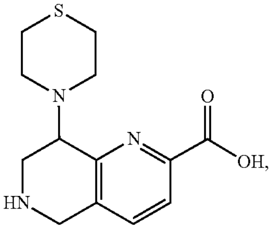
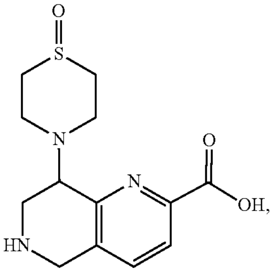
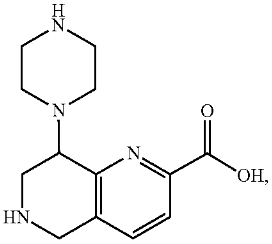
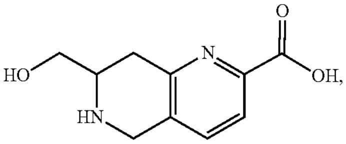
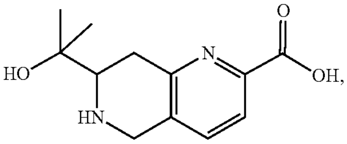
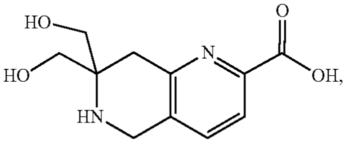
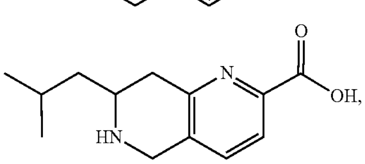
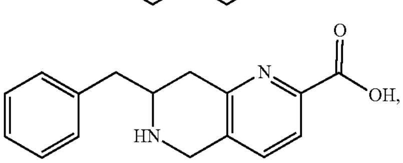
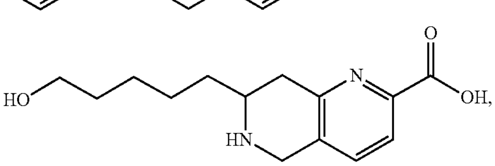
-continued
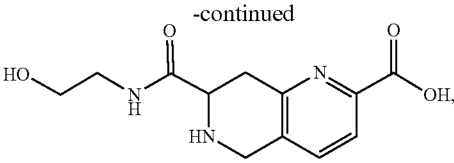
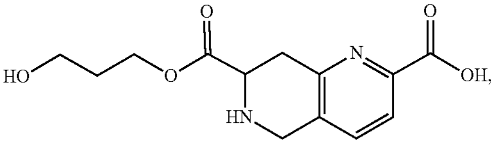
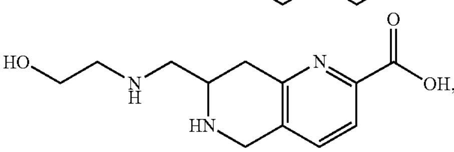
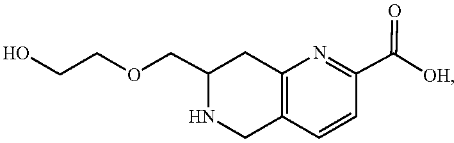
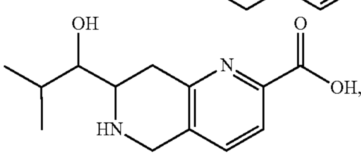
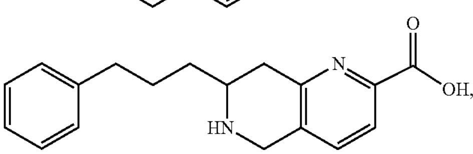
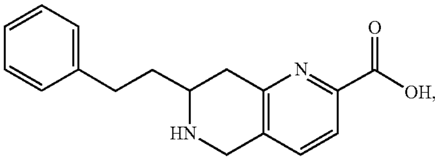
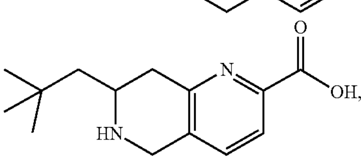
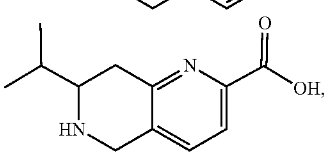
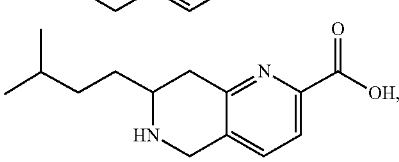
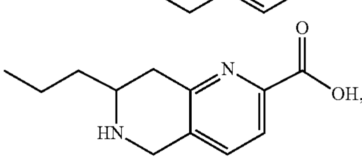
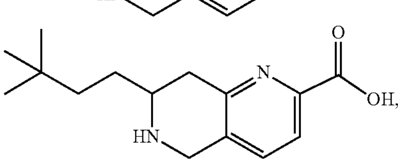

-continued

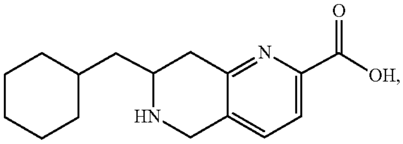
,

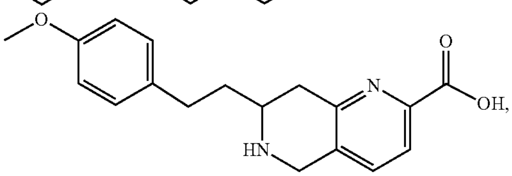
,

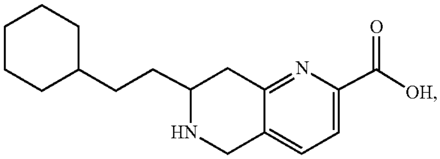
,

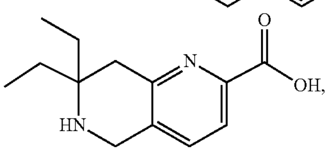
,

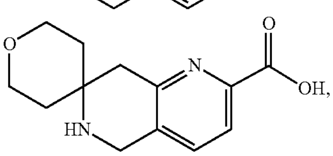
,

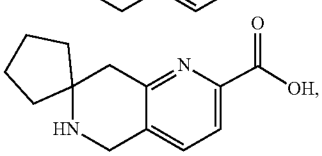
,

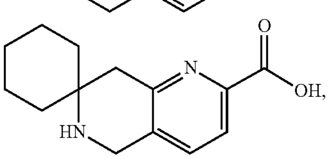
,

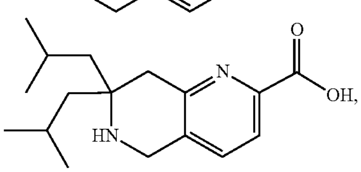
,

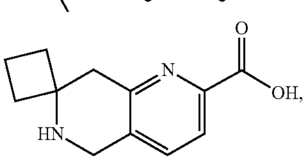
,

Another object of the present invention is to provide a pharmaceutical composition, comprising at least one of the aforementioned compounds, or a pharmaceutically acceptable salt, hydrate, isomer, prodrug and mixture thereof, and at least one pharmaceutically acceptable excipient.

Another object of the present invention is to provide a use of the aforementioned compounds, or a pharmaceutically acceptable salt, hydrate, isomer, prodrug and mixture thereof, or a pharmaceutical composition for the manufacture of a medicament. The medicament has a therapeutic activity of blood coagulation and hemostasis, and can be used for abnormal bleeding caused by hyperfibrinolysis, surgical and post-operative bleeding and the like.

Another object of the present invention is to provide a method for treating and/or alleviating bleeding diseases or conditions, comprising administering to a patient in need thereof one or more of the aforementioned pharmaceutical compositions or compounds of formula I or a pharmaceutically acceptable salt, hydrate, isomer, prodrug or mixture thereof.

Definitions

Unless otherwise stated, the following terms and phrases used herein are intended to have the following meanings. A particular term or phrase should not be considered indeterminate or unclear if it is not specifically defined, but should be understood according to its ordinary meaning. When a trade name appears herein, it is intended to refer to its corresponding commercial product or its active ingredient.

The term "pharmaceutically acceptable" as used herein means suitable for use in contact with tissues of humans and animals without undue toxicity, irritation, allergic reaction or other problems or complications, having a reasonable benefit/risk ratio.

The term "pharmaceutically acceptable salt" refers to salts of the compound of the present invention prepared from a compound of the present invention having a particular substituent with relatively nontoxic acids or bases. When a compound of the present invention contains relatively acidic functional groups, base addition salts can be obtained by contacting the neutral form of such compound with a sufficient amount of base, either in neat or in a suitable inert solvent. When a compound of the present invention contains relatively basic functional groups, acid addition salts can be obtained by contacting the neutral form of such compound with a sufficient amount of acid, either in neat or in a suitable inert solvent.

The compounds of the present invention may exist in specific geometric or stereoisomeric forms. The present invention contemplates all such compounds, including the cis and trans isomers, (−)- and (+)- enantiomers, (R)- and (S)-enantiomers, diastereomers, (D)-isomers, (L)-isomers, and racemic and other mixtures thereof, all of which are within the scope of the present invention.

"Alkyl" refers to a straight chain or branched saturated aliphatic hydrocarbon group, for example, $C_1$-$C_4$ alkyl and $C_1$-$C_6$ alkyl refer to saturated aliphatic hydrocarbon groups containing 1 to 4 carbon atoms and 1 to 6 carbon atoms, respectively, including but not limited to, methyl, ethyl, propyl, isopropyl, n-butyl, isobutyl, tert-butyl, pentyl, isopentyl, neopentyl, hexyl, 3,3-dimethylbutyl, and the like, and their various isomers.

"Alkoxy" means-O-alkyl; for example, $C_1$-$C_6$ alkoxy refers to a straight chain or branched alkoxy containing 1 to 6 carbon atoms, $C_1$-$C_3$ alkoxy refers to a straight chain or branched alkoxy containing 1 to 3 carbon atoms. Typical alkoxy groups include, but are not limited to, methoxy, ethoxy, n-propoxy, isopropoxy, and the like.

"Cycloalkyl" refers to a saturated or partially unsaturated monocyclic or polycyclic cyclic hydrocarbon substituent. For example, "$C_3$-$C_6$ cycloalkyl" refers to cycloalkyl groups containing 3 to 6 carbon atoms. Typical cycloalkyl groups include, but are not limited to, cyclopropyl, cyclobutyl, cyclopentyl, cyclopentenyl, cyclohexyl, cyclohexenyl, and the like.

"Aliphatic heterocyclyl" refers to a saturated, monocyclic hydrocarbon substituent in which one or more ring atoms are replaced with a heteroatom selected from N, O and S, the remaining ring atoms are carbon, and wherein the S heteroatom is optionally oxidized. For example, "3-8 membered aliphatic heterocyclyl" means a saturated cyclic hydrocarbon substituent containing 3 to 8 ring atoms, wherein one or more ring atoms are replaced with a heteroatom selected from N, O and S, the remaining ring atoms are carbon, and wherein the S heteroatom is optionally oxidized. Specific examples of the aliphatic heterocyclyl in the present invention include, but are not limited to, oxetanyl, pyrrolidinyl, tetrahydrofuranyl, tetrahydropyranyl, tetrahydrothiophenyl, piperidinyl, piperazinyl, morpholinyl, thiomorpholinyl, 1-oxido-4-thiomorpholinyl and 1,1-dioxido-4-thiomorpholinyl, etc.

"Aromatic heterocyclyl" refers to an aromatic cyclic substituent in which one or more ring atoms are replaced with a heteroatom selected from N, O and S, with the remaining ring atoms being carbon. For example, "5-6 membered aromatic heterocyclyl" refers to an aromatic heterocyclyl containing 5 to 6 ring atoms. Specific examples of the aromatic heterocyclyl described herein include, but are not limited to, pyridyl, pyrimidinyl, imidazolyl, pyridazinyl, pyrazolyl, thiazolyl, oxazolyl, isoxazolyl, 1,2, 4-oxadiazolyl.

"Aryl" refers to an aromatic cyclic group, e.g., "6-10 membered aryl" refers to an aromatic cyclic group containing 6 to 10 carbon ring atoms. Examples of aryl described herein include, but are not limited to, phenyl, naphthyl, and the like.

"Halogen" includes fluorine, chlorine, bromine and iodine.

"Optionally" means that the subsequently described event or circumstance may, but need not, occur.

The abbreviations used in the present invention are known to those skilled in the art and, unless otherwise indicated, are intended to have the meanings known in the art. For example, DMF represents N,N-dimethylformamide; THF represents tetrahydrofuran; Me represents methyl.

Tests have proved that the compounds of the present invention have excellent blood coagulation and hemostasis activities, which are obviously superior to tranexamic acid, the most widely used hemostatic drug in clinical practice, and have great clinical application value.

DETAILED DESCRIPTION

The following examples illustrate the synthesis of the compounds and intermediates of the present invention by way of example only and should not be construed as limiting the scope of the invention. Unless otherwise specified, the raw materials and reagents involved in the present invention can be obtained from commercial sources, and the specific sources do not influence the implementation of the technical solution of the present invention.

Preparation 1: preparation of tert-butyl 2-chloro-8-hydroxy-7,8-dihydro-1,6-naphthyridine-6(5H)-carboxylate

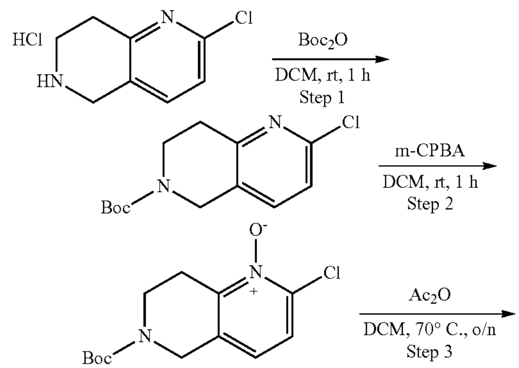

-continued

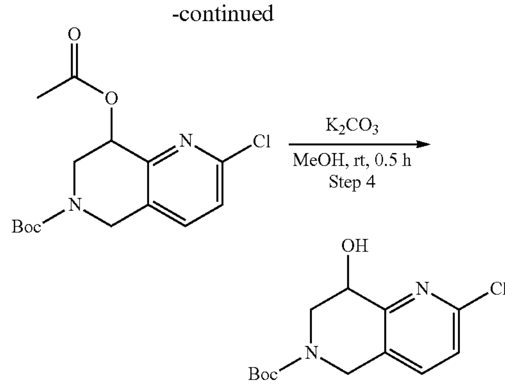

Step 1: preparation of tert-butyl 2-chloro-7,8-dihydro-1,6-naphthyridine-6(5H)-carboxylate 2-Chloro-5,6,7,8-tetrahydro-1,6-naphthyridine hydrochloride (5 g) was dissolved in dichloromethane (50 ml), triethylamine (10 ml) was added, and di-tert-butyl dicarbonate (6.7 ml) was slowly added dropwise. After the completion of addition, the reaction was carried out at room temperature for 1 hour, and LC-MS showed that the reaction was complete. The system was concentrated to give a crude oil, which was separated by chromatographic column to obtain the title compound (6 g).

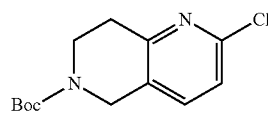 [SMILES: CC(C)(C)OC(=O)N1CCc2nc(Cl)ccc2C1]

MS (ESI) m/z $(M+H)^+$=269.1.

Step 2: preparation of 6-(tert-butoxycarbonyl)-2-chloro-5,6,7,8-tetrahydro-1,6-naphthyridine 1-oxide Tert-butyl 2-chloro-7,8-dihydro-1,6-naphthyridine-6(5H)-carboxylate (9 g) was weighed out and dissolved in dichloromethane (100 ml), and m-chloroperoxybenzoic acid (11.7 g) was added in portions under cooling with an ice-bath. The reaction was carried out at room temperature for 1 hour, and LC-MS showed that the reaction was complete. Dichloromethane and water were added, the layers were separated and the aqueous layer was extracted, and the organic phase was concentrated to dryness. The resulting crude product was purified by column chromatography to obtain the title compound (7.0 g).

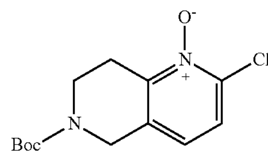

MS (ESI) m/z $(M+H)^+$=285.1.

Step 3: preparation of tert-butyl 8-acetoxy-2-chloro-7,8-dihydro-1,6-naphthyridine-6(5H)-carboxylate 6-(Tert-butyloxycarbonyl)-2-chloro-5,6,7,8-tetrahydro-1,6-naphthyridine 1-oxide (7 g) was weighed out and dissolved in acetic anhydride (80 mL), the system was evacuated and backfilled with nitrogen (3 times), and then heated to 70° C. to react overnight. LC-MS showed that the reaction was complete. The reaction was concentrated under reduced pressure to remove most of acetic anhydride, and ethyl acetate and water were added. The aqueous phase was extracted with ethyl acetate for 3 times, and the extract was washed with saturated sodium bicarbonate solution for 2 times. The organic phase was dried and concentrated, and the residue was separated and purified by chromatographic column to obtain the title compound (5 g).

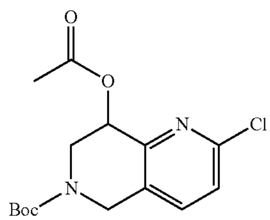 [SMILES: CC(=O)OC1CN(C(=O)OC(C)(C)C)Cc2ccc(Cl)nc21]

MS (ESI) m/z $(M+H)^+$=327.1.

Step 4: preparation of tert-butyl 2-chloro-8-hydroxy-7,8-dihydro-1,6-naphthyridine-6(5H)-carboxylate Tert-butyl 8-acetoxy-2-chloro-7,8-dihydro-1,6-naphthyridine-6(5H)-carboxylate (3 g) was weighed out and dissolved in methanol (30 ml), and potassium carbonate (635 mg) was added. After the completion of addition, the reaction was carried out at room temperature for 0.5 hour, LC-MS showed that the reaction was complete. Ethyl acetate and water were added, the aqueous layer was extracted with ethyl acetate for 3 times. The organic phase was dried and concentrated to give an oily crude product, which was separated and purified by column chromatography to obtain the title compound (1.9 g).

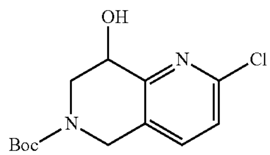 [SMILES: CC(C)(C)OC(=O)N1Cc2ccc(Cl)nc2C(O)C1]

MS (ESI) m/z $(M+H)^+$=285.1.

Preparation 2: preparation of 6-(tert-butyl)7-methyl 2-chloro-7,8-dihydro-1,6-naphthyridine-6,7(5H)-dicarboxylate

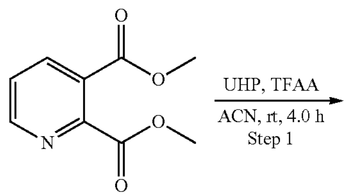

-continued

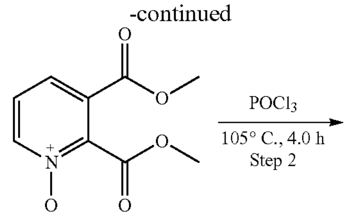

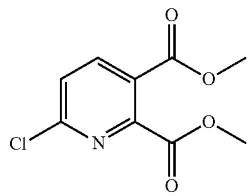

LiBH4
THF/MeOH, rt, 3 h
Step 3

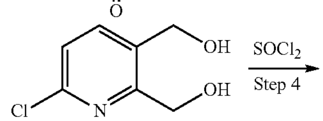

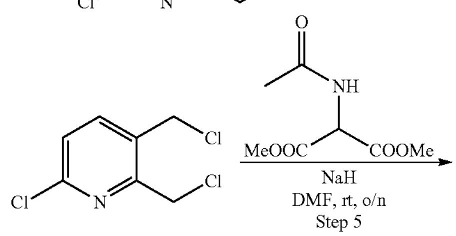

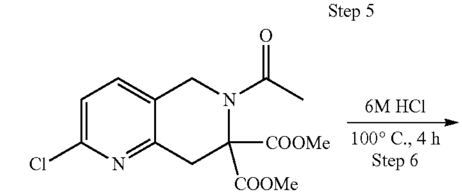

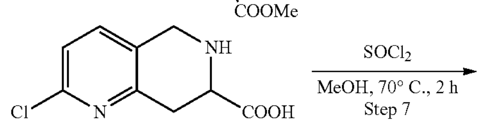

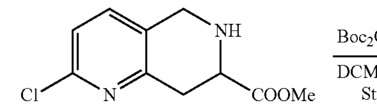

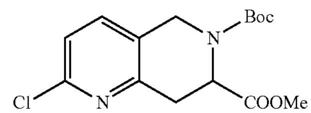 [SMILES: COC(=O)C1Cc2nc(Cl)ccc2CN1C(=O)OC(C)(C)C]

Step 1: preparation of 2,3-bis(methoxycarbonyl)pyridine 1-oxide

Dimethyl pyridin-2,3-dicarboxylate (4.90 g) was weighed out and dissolved in acetonitrile (60 mL), carbamide peroxide (4.71 g) was added under cooling with an ice bath, and trifluoroacetic anhydride (10.5 g) was slowly added dropwise. After the completion of addition, the system became a clear solution, and the temperature was raised to room temperature and reacted for 4 hours. TLC showed substantial completion of the reaction. The reaction was quenched by adding aqueous sodium metabisulfite solution. Dichloromethane and water were added, the layers were separated and the aqueous layer was extracted with mixed solvent (DCM/MeOH=10/1). The organic phase was dried over anhydrous sodium sulfate, filtered with suction, and the filtrate was concentrated to dryness to obtain the title compound (5.15 g).

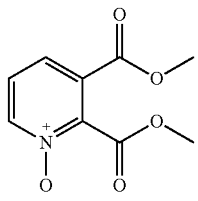

MS (ESI) m/z $(M+H)^+$=212.1.

Step 2: preparation of dimethyl 6-chloropyridine-2,3-dicarboxylate

Phosphorus oxychloride (30 mL) was added to 2,3-bis(methoxycarbonyl)pyridine 1-oxide (5.15 g) under ice-cooling, and the temperature was raised to 105° C. to react for 4 hours. TLC showed completion of the reaction. The reaction mixture was concentrated under reduced pressure, diluted with ethyl acetate, added dropwise to crushed ice, aqueous sodium carbonate solution was added to adjust pH=10, extracted with ethyl acetate, and the organic phase was washed with aqueous sodium chloride solution. The organic phase was concentrated to dryness and the crude product was purified by column chromatography to obtain the title compound (3.52 g).

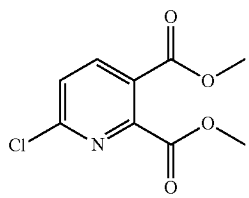

MS (ESI) m/z $(M+H)^+$=230.1.

Step 3: preparation of (6-chloropyridin-2,3-diyl)methanol

Dimethyl 6-chloropyridine-2,3-dicarboxylate (3.50 g) was weighed out and dissolved in tetrahydrofuran (72 mL) and methanol (1.5 mL), and lithium borohydride (0.84 g) was added in portions under ice bath cooling. The mixture was allowed to warm to room temperature and reacted for 3 hours. TLC showed that the reaction was complete. The reaction system was poured into aqueous sodium bicarbonate solution, ethyl acetate was added, the aqueous layer was separated and extracted, the organic phase was dried over anhydrous sodium sulfate, filtered with suction, and the filtrate was concentrated to obtain the title compound (2.63 g).

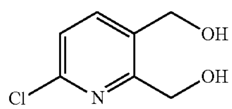 [SMILES: OCc1ccc(Cl)nc1CO]

MS (ESI) m/z $(M+H)^+$=174.1.

Step 4: preparation of 6-chloro-2,3-bis(chloromethyl)pyridine

Thionyl chloride (40 mL) was added to (6-chloropyridin-2,3-diyl)dimethanol (2.63 g) under ice-bath cooling, and reacted at room temperature for 3 hours. Due to the presence of some monochlorinated intermediate, the temperature was raised to 35° C. and reacted for 3 hours, and TLC showed that the reaction was complete. The system was concentrated under reduced pressure, diluted with ethyl acetate, added dropwise to crushed ice, aqueous sodium carbonate solution was added to adjust pH=10, extracted with ethyl acetate, and the organic phase was washed with aqueous sodium chloride solution. The organic phase was concentrated to dryness and the crude product was purified by column chromatography to obtain the title compound (2.1 g).

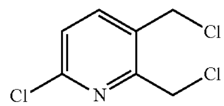 [SMILES: ClCc1ccc(Cl)nc1CCl]

MS (ESI) m/z $(M+H)^+$=210.1.

Step 5: preparation of Dimethyl 6-acetyl-2-chloro-5,6-dihydro-1,6-naphthyridine-7,7(8H)-dicarboxylate 6-Chloro-2,3-bis(chloromethyl)pyridine (2.10 g) was weighed out and dissolved in N,N-dimethylformamide (15 mL), and dimethyl acetylaminomalonate (2.17 g) and sodium hydride (0.40 g) were added successively under ice bath cooling. The reaction was carried out at room temperature for 1 hour, and sodium hydride (0.40 g) was added under ice bath cooling, and then reacted at room temperature overnight. TLC showed the reaction was complete. Ethyl acetate and water were added, the aqueous layer was separated and extracted. The organic phase was concentrated to dryness and the crude product was purified by column chromatography to obtain the title compound (1.74 g).

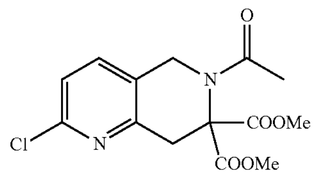 [SMILES: COC(=O)C1(C(=O)OC)Cc2nc(Cl)ccc2CN1C(C)=O]

MS (ESI) m/z $(M+H)^+$=327.1.

Step 6: preparation of 2-chloro-5,6,7,8-tetrahydro-1,6-naphthyridine-7-carboxylic acid hydrochloride 6M hydrochloric acid (15 mL) was added to dimethyl 6-acetyl-2-chloro-5,6-dihydro-1,6-naphthyridine-7,7(8H)-dicarboxylate (1.74 g) and reacted under sealed condition at 100° C. for 4 hours. TLC showed completion of the reaction. The system was concentrated to dryness under reduced pressure to obtain the title compound (1.16 g).

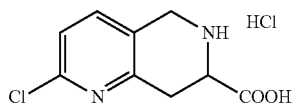 [SMILES: O=C(O)C1Cc2nc(Cl)ccc2CN1 ; Cl]

MS (ESI) m/z $(M+H)^+$=213.1.

Step 7: preparation of methyl 2-chloro-5,6,7,8-tetrahydro-1,6-naphthyridine-7-carboxylate hydrochloride 2-Chloro-5,6,7,8-tetrahydro-1,6-naphthyridine-7-carboxylic acid hydrochloride (1.16 g) was weighed out and dissolved in methanol (20 mL), and thionyl chloride (1.67 g) was slowly added dropwise under ice bath cooling. The reaction was refluxed at 70° C. for 2 hours, and TLC showed completion of the reaction. The system was concentrated to dryness under reduced pressure to obtain the title compound (1.23 g).

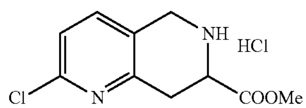 [SMILES: COC(=O)C1Cc2nc(Cl)ccc2CN1 ; Cl]

MS (ESI) m/z $(M+H)^+$=227.1.

Step 8: preparation of 6-(tert-butyl) 7-methyl 2-chloro-7,8-dihydro-1,6-naphthyridine-6,7(5H)-dicarboxylate Methyl 2-chloro-5,6,7,8-tetrahydro-1,6-naphthyridine-7-carboxylate hydrochloride (1.23 g) was weighed out and dissolved in dichloromethane (25 mL), and triethylamine (1.89 g) and di-tert-butyl dicarbonate (1.53 g) were added successively. The reaction was allowed to react at room temperature for 2 hours, and TLC showed completion of the reaction. Dichloromethane and water were added, the aqueous layer was separated and extracted, and the organic phase was concentrated to dryness. The resulting crude product was purified by column chromatography to obtain the title compound (1.19 g).

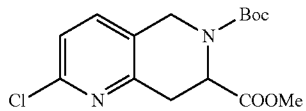 [SMILES: COC(=O)C1Cc2nc(Cl)ccc2CN1C(=O)OC(C)(C)C]

MS (ESI) m/z $(M+H)^+$=327.1.

$^1$H NMR (400 MHz, Chloroform-d) δ 7.42 (dd, J=12.5, 8.0 Hz, 1H), 7.21 (d, J=8.1 Hz, 1H), 5.34 (d, J=6.7 Hz, 0.5H), 5.07 (dd, J=7.2, 2.9 Hz, 0.5H), 4.79 (dd, J=22.4, 17.0 Hz, 1H), 4.52 (dd, J=31.0, 17.1 Hz, 1H), 3.68 (d, J=7.7 Hz, 3H), 3.55-3.38 (m, 1H), 3.38-3.20 (m, 1H), 1.52 (d, J=17.9 Hz, 9H).

Example 1: preparation of 5,6,7,8-tetrahydro-1,6-naphthyridine-2-carboxylic acid hydrochloride

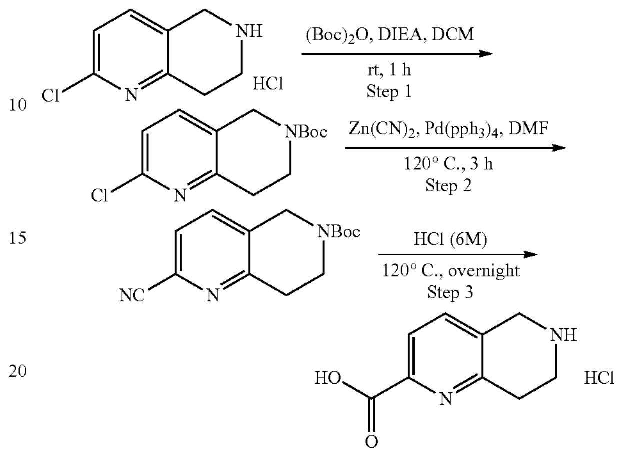

Step 1: preparation of tert-butyl 2-chloro-7,8-dihydro-1,6-naphthyridine-6(5H)-carboxylate 2-Chloro-5,6,7,8-tetrahydro-1,6-naphthyridine hydrochloride (0.9 g) was weighed out and suspended in dichloromethane (15 mL), N,N-diisopropylethylamine (1.4 g) was added to release the free base, and then di-tert-butyl dicarbonate (1.15 g) was added and reacted at room temperature for 1 h. TLC indicated complete consumption of the starting material. Purification by column chromatography gave the title compound (1.12 g).

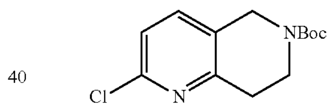

MS (ESI) m/z $(M+H)^+$=269.0.

Step 2: preparation of tert-butyl 2-cyano-7,8-dihydro-1,6-naphthyridine-6(5H)-carboxylate Tert-butyl 2-chloro-7,8-dihydro-1,6-naphthyridine-6(5H)-carboxylate (1.12 g) was weighed out and dissolved in N,N-dimethylformamide (20 mL), zinc cyanide (2.44 g) and tetrakis(triphenylphosphine)palladium (483 mg) were added, the system was evacuated and backfilled with argon (3 times), and then reacted at 120° C. for 3 hours. TLC showed complete consumption of the starting material. The mixture was diluted with ethyl acetate, filtered through celite, extracted 2 times with ethyl acetate. The organic phase was washed 1 time with saturated brine, dried over anhydrous sodium sulfate and concentrated. The residue was purified by column chromatography to give the title compound (1.1 g).

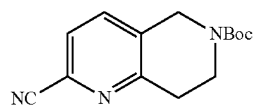 [SMILES: CC(C)(C)OC(=O)N1CCc2nc(C#N)ccc2C1]

MS (ESI) m/z $(M+H)^+$=260.0.

Step 3: preparation of 5,6,7,8-tetrahydro-1,6-naphthyridine-2-carboxylic acid hydrochloride Tert-butyl 2-cyano-7,8-dihydro-1,6-naphthyridine-6(5H)-carboxylate (1.1 g) was weighed out and dissolved in 6M aqueous hydrochloric acid (25 mL) and reacted at 120° C. overnight. LCMS indicated complete consumption of starting material and the reaction was concentrated to dryness. The residue was separated by pre-HPLC to give a pale yellow solid (726 mg).

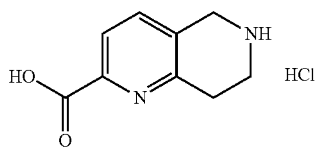 [SMILES: O=C(O)c1ccc2c(n1)CCNC2 ; Cl]

MS (ESI) m/z $(M+H)^+$=179.0.

$^1$H NMR (400 MHz, Methanol-d 4) δ 8.21 (d, J=8.1 Hz, 1H), 8.12 (d, J=8.0 Hz, 1H), 4.60 (s, 2H), 3.71 (t, J=6.4 Hz, 2H), 3.42 (t, J=6.4 Hz, 2H).

Example 2: preparation of 8-hydroxy-5,6,7,8-tetrahydro-1,6-naphthyridine-2-carboxylic acid hydrochloride

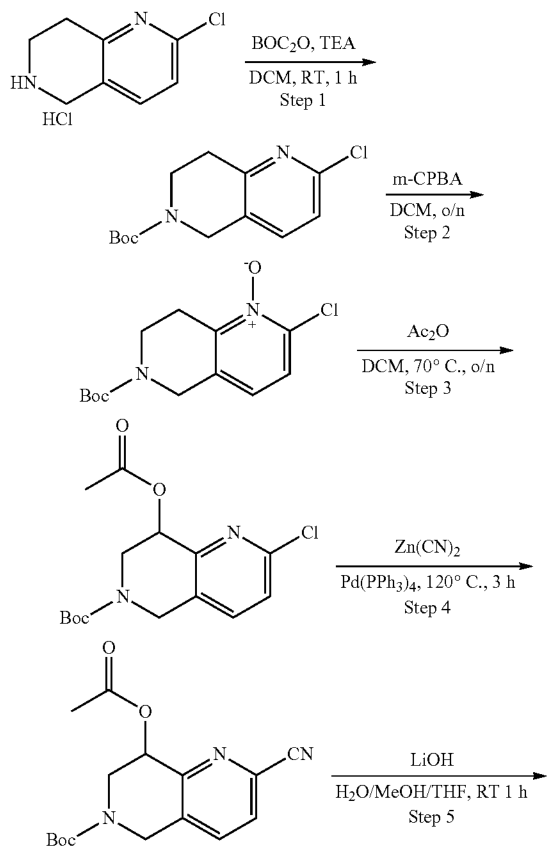

-continued

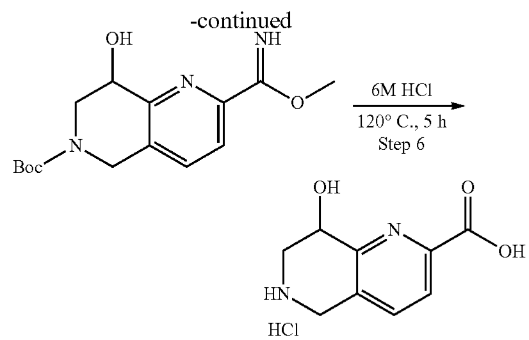

Step 1: preparation of tert-butyl 2-chloro-7,8-dihydro-1,6-naphthyridine-6(5H)-carboxylate 2-Chloro-5,6,7,8-tetrahydro-1,6-naphthyridine hydrochloride (5 g) was dissolved in dichloromethane (50 ml), triethylamine (10 ml) was added, and then di-tert-butyl dicarbonate (6.7 ml) was slowly added dropwise. After the addition was complete, the reaction was carried out at room temperature for 1 hour, and LC-MS showed completion of the reaction. The system was concentrated to give a crude oil, which was purified by column chromatography to give the title compound (5.5 g).

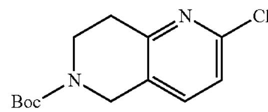 [SMILES: CC(C)(C)OC(=O)N1CCc2nc(Cl)ccc2C1]

MS (ESI) m/z $(M+H)^+$=269.1.

Step 2: preparation of 6-(tert-butoxycarbonyl)-2-chloro-5,6,7,8-tetrahydro-1,6-naphthyridine-1-oxide Tert-butyl 2-chloro-7,8-dihydro-1,6-naphthyridine-6(5H)-carboxylate (2 g) was weighed out and dissolved in dichloromethane (50 ml), and m-chloroperoxybenzoic acid (2.6 g) was added in portions under ice-bath cooling. The reaction was carried out overnight at room temperature, and LC-MS indicated completion of the reaction. Dichloromethane and water were added, the aqueous layer was separated and extracted, and the organic phase was concentrated to dryness. The resulting crude product was purified by column chromatography to give the title compound (1.5 g).

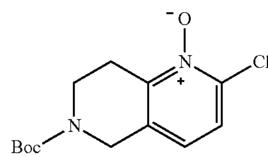 [SMILES: CC(C)(C)OC(=O)N1CCc2c(ccc(Cl)[n+]2[O-])C1]

MS (ESI) m/z $(M+H)^+$=285.1.

Step 3: preparation of tert-butyl 8-acetoxy-2-chloro-7,8-dihydro-1,6-naphthyridine-6(5H)-carboxylate 6-(Tert-butyloxycarbonyl)-2-chloro-5,6,7,8-tetrahydro-1,6-naphthyridine-1-oxide (300 mg) was weighed out and dissolved in acetic anhydride (5 mL), the system was evacuated and backfilled with nitrogen (3 times), and then heated to 70° C. and reacted overnight. LC-MS showed completion of the reaction. The reaction mixture was concentrated under reduced pressure to remove most of the acetic anhydride, and ethyl acetate and water were added. The aqueous was extracted 3 times, the organic phase was washed 2 times with saturated sodium bicarbonate solution, dried and concentrated. The residue was purified by column chromatography to obtain the title compound (280 mg).

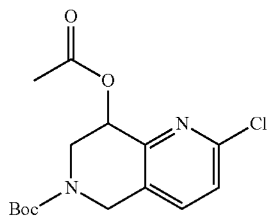 [SMILES: CC(=O)OC1CN(C(=O)OC(C)(C)C)Cc2ccc(Cl)nc21]

MS (ESI) m/z $(M+H)^+$=327.1.

Step 4: preparation of tert-butyl 8-acetoxy-2-cyano-7,8-dihydro-1,6-naphthyridine-6(5H)-carboxylate Tert-butyl 8-acetoxy-2-chloro-7,8-dihydro-1,6-naphthyridine-6(5H)-carboxylate (150 mg) was weighed out and dissolved in N,N-dimethylformamide (6 mL), and zinc cyanide (270 mg) and tetrakis(triphenylphosphine)palladium (105.9 mg) were added. The system was evacuated and backfilled with nitrogen (3 times), then heated to 120° C. and reacted for 3 hours. LC-MS showed completion of the reaction. Ethyl acetate and water were added, the aqueous phase was extracted 3 times with ethyl acetate, and the organic phase was dried and concentrated. The residue was purified by column chromatography to obtain the title compound (60 mg).

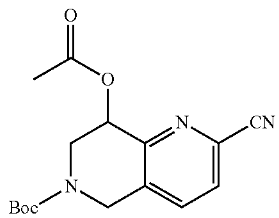 [SMILES: CC(=O)OC1CN(C(=O)OC(C)(C)C)Cc2ccc(C#N)nc21]

MS (ESI) m/z $(M+H)^+$=318.1.

Step 5: preparation of tert-butyl 8-hydroxy-2-(imino (methoxy)methyl)-7,8-dihydro-1,6-naphthyridine-6 (5H)-carboxylate Tert-butyl 8-acetoxy-2-cyano-7,8-dihydro-1,6-naphthyridine-6(5H)-carboxylate (60 mg) was weighed out and dissolved in a solution of methanol (1 mL), tetrahydrofuran (1 mL) and water (1 mL), lithium hydroxide monohydrate (32 mg) was added and reacted at room temperature for 1 hour. LC-MS showed completion of the reaction. Ethyl acetate and water were added, the aqueous phase was extracted 3 times with ethyl acetate, and the organic phase was dried and concentrated to give the title compound (50 mg).

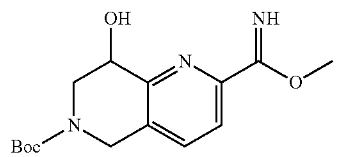 [SMILES: COC(=N)c1ccc2c(n1)C(O)CN(C(=O)OC(C)(C)C)C2]

MS (ESI) m/z $(M+H)^+$=308.1.

Step 6: preparation of 8-hydroxy-5,6,7,8-tetrahydro-1,6-naphthyridine-2-carboxylic acid hydrochloride Tert-butyl 8-hydroxy-2-(imino (methoxy)methyl)-7,8-dihydro-1,6-naphthyridine-6(5H)-carboxylate (50 mg) was weighed out and dissolved in 6M aqueous hydrochloric acid (4 mL). The system was heated to 120° C. and reacted for 5 hours. LC-MS showed the reaction was complete. The reaction was concentrated and the residue was purified by pre-HPLC to give the title compound (35 mg).

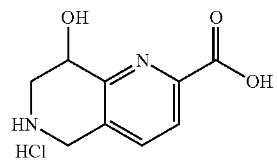 [SMILES: O=C(O)c1ccc2c(n1)C(O)CNC2 ; Cl]

MS (ESI) m/z $(M+H)^+$=195.0.

$^1$H NMR (400 MHz, Deuterium Oxide) δ 8.13 (d, J=8.1 Hz, 1H), 7.96 (d, J=8.1 Hz, 1H), 5.07 (s, 1H), 4.64-4.45 (m, 2H), 3.79-3.57 (m, 2H).

Example 3: preparation of 8-amino-5,6,7,8-tetrahydro-1,6-naphthyridine-2-carboxylic acid dihydrochloride

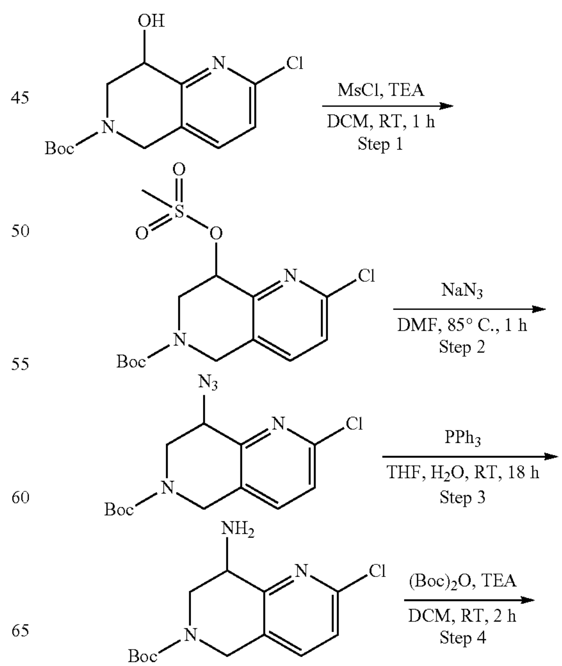

-continued

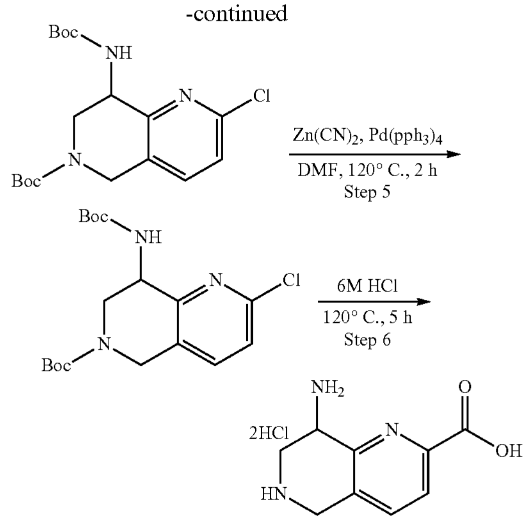

Step 1: preparation of tert-butyl 2-chloro-8-((methylsulfonyl)oxy)-7,8-dihydro-1,6-naphthyridine-6(5H)-carboxylate Tert-butyl 2-chloro-8-hydroxy-7,8-dihydro-1,6-naphthyridine-6(5H)-carboxylate (100 mg) was weighed out and dissolved in dichloromethane (4 ml), and triethylamine (106 mg) was added under ice-bath cooling. The system was evacuated and backfilled with nitrogen (3 times), then methanesulfonyl chloride (80 mg) was added dropwise, and the reaction was allowed to proceed at room temperature for 1 hour. LC-MS showed completion of the reaction. Dichloromethane and water were added, the aqueous layer was separated and extracted, and the organic phase was concentrated to dryness to give the title compound (126.7 mg).

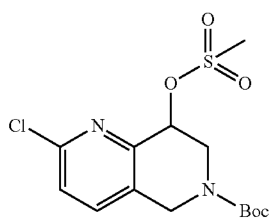 [SMILES: CC(C)(C)OC(=O)N1Cc2ccc(Cl)nc2C(OS(C)(=O)=O)C1]

MS (ESI) m/z $(M+H)^+$=363.1.

Step 2: preparation of tert-butyl 8-azido-2-chloro-7,8-dihydro-1,6-naphthyridine-6(5H)-carboxylate Tert-butyl 2-chloro-8-((methanesulfonyl)oxy)-7,8-dihydro-1,6-naphthyridine-6(5H)-carboxylate (126 mg) was weighed out and dissolved in N,N-dimethylformamide (4 ml), and sodium azide (30 mg) was added under ice-bath cooling. The reaction was heated to 85° C. for 1 hour and TLC showed completion of the reaction. Ethyl acetate and water were added, the aqueous layer was separated and extracted, and the organic phase was concentrated to dryness. The resulting crude product was purified by column chromatography to give the title compound (90 mg).

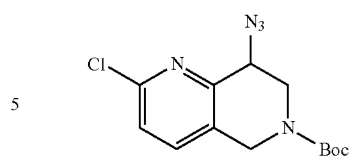

MS (ESI) m/z $(M+H)^+$=310.1.

Step 3: preparation of tert-butyl 8-amino-2-chloro-7,8-dihydro-1,6-naphthyridine-6(5H)-carboxylate Tert-butyl 8-azido-2-chloro-7,8-dihydro-1,6-naphthyridine-6(5H)-carboxylate (90 mg) was weighed out and dissolved in tetrahydrofuran (3 mL) and water (0.3 mL), triphenylphosphine (152 mg) was added and the reaction was carried out at room temperature for 18 hours. LC-MS showed completion of the reaction. Ethyl acetate and water were added, the aqueous layer was extracted with ethyl acetate (3 times), the organic layer was dried and concentrated, and the residue was purified by column chromatography to obtain the title compound (70 mg).

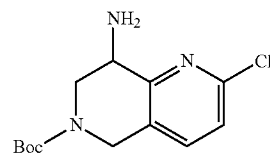

MS (ESI) m/z $(M+H)^+$=284.1.

Step 4: preparation of tert-butyl 8-((tert-butoxycarbonyl)amino)-2-chloro-7,8-dihydro-1,6-naphthyridine-6(5H)-carboxylate Tert-butyl 8-amino-2-chloro-7,8-dihydro-1,6-naphthyridine-6(5H)-carboxylate (70 mg) was weighed out and dissolved in methylene chloride (6 mL), triethylamine (37 mg) was added, and then di-tert-butyl dicarbonate (80 mg) was slowly added dropwise. The reaction was carried out at room temperature for 2 hours. LC-MS showed completion of the reaction. The system was concentrated and the residue was purified by column chromatography to give the title compound (70 mg).

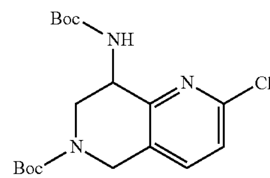 [SMILES: CC(C)(C)OC(=O)NC1CN(C(=O)OC(C)(C)C)Cc2ccc(Cl)nc21]

MS (ESI) m/z $(M+H)^+$=384.1.

Step 5: preparation of tert-butyl 8-((tert-butoxycarbonyl) amino)-2-cyano-7,8-dihydro-1,6-naphthyridine-6(5H)-carboxylate Tert-butyl 8-((tert-butoxycarbonyl)amino)-2-chloro-7,8-dihydro-1,6-naphthyridine-6(5H)-carboxylate (30 mg) was dissolved in N,N-dimethylformamide (3 mL), zinc cyanide (90 mg) and tetrakis(triphenylphosphine)palladium (72 mg)

were added, the system was evacuated and backfilled with nitrogen (3 times), and the mixture was heated to 120° C. for 2 hours. LC-MS showed completion of the reaction. Ethyl acetate and water were added, the aqueous layer was extracted with ethyl acetate (3 times), the organic phase was dried and concentrated, and the residue was purified by column chromatography to obtain the title compound (25 mg).

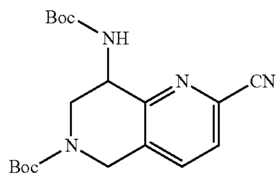 [SMILES: CC(C)(C)OC(=O)NC1CN(C(=O)OC(C)(C)C)Cc2ccc(C#N)nc21]

MS (ESI) m/z $(M+H)^+$=375.2.

Step 6: preparation of 8-amino-5,6,7,8-tetrahydro-1,6-naphthyridine-2-carboxylic acid dihydrochloride Tert-butyl 8-((tert-butoxycarbonyl) amino)-2-cyano-7,8-dihydro-1,6-naphthyridine-6(5H)-carboxylate (25 mg) was weighed out and dissolved in 6M aqueous hydrochloric acid (4 mL). The system was heated to 120° C. and reacted for 5 hours. LC-MS showed the reaction was complete. The reaction was concentrated and the residue was purified by pre-HPLC to give the title compound (13 mg).

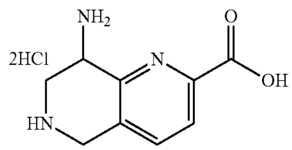 [SMILES: NC1CNCc2ccc(C(=O)O)nc21]

MS (ESI) m/z $(M+H)^+$=193.9.

$^1$H NMR (400 MHz, Deuterium Oxide) δ 8.09 (d, J=8.1 Hz, 1H), 7.90 (d, J=8.1 Hz, 1H), 4.96 (dd, J=9.9, 6.2 Hz, 1H), 4.58 (d, J=2.6 Hz, 2H), 4.11 (dd, J=13.0, 6.1 Hz, 1H), 3.63 (dd, J =13.0, 9.9 Hz, 1H).

Example 4: preparation of 8-((2-hydroxyethyl) amino)-5,6,7,8-tetrahydro-1,6-naphthyridine-2-carboxylic acid dihydrochloride

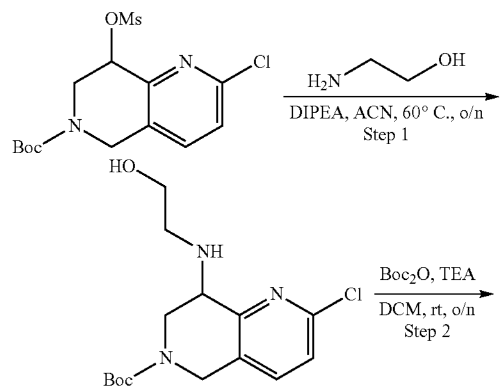

-continued

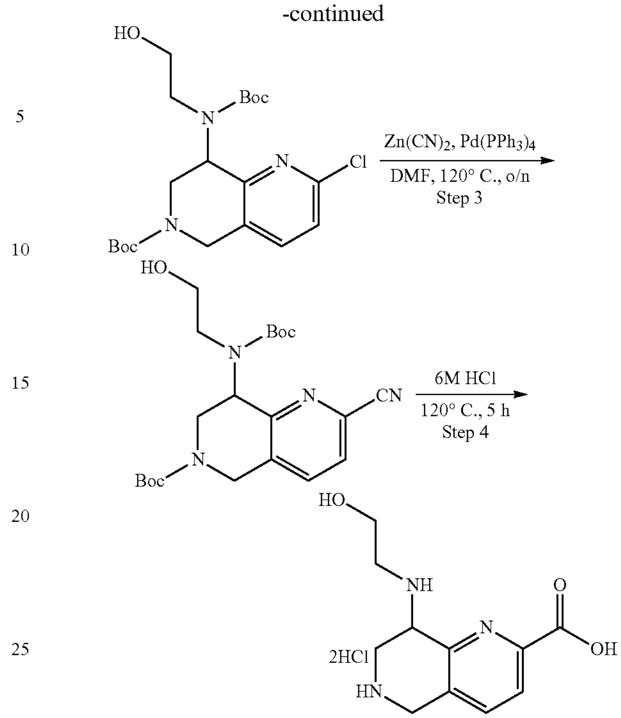

Step 1: preparation of tert-butyl 2-chloro-8-((2-hydroxyethyl)amino)-7,8-dihydro-1,6-naphthyridine-6(5H)-carboxylate Tert-butyl 2-chloro-8-((methanesulfonyl)oxy)-7,8-dihydro-1,6-naphthyridine-6(5H)-carboxylate (100 mg) was dissolved in acetonitrile (4 mL) at room temperature, and N,N-diisopropylethylamine (0.23 mL) and ethanolamine (34 mg) were added. The reaction was heated to 60° C. overnight, and TLC showed completion of the reaction. Dichloromethane and water were added, the layers were separated, the aqueous layer was extracted with dichloromethane, and the organic phase was concentrated to dryness. The resulting crude product was purified by silica gel column chromatography to give the title compound (54 mg).

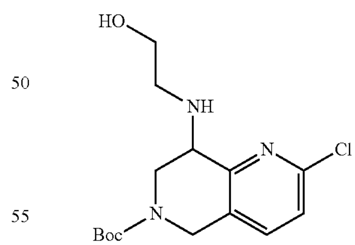

MS (ESI) m/z $(M+H)^+$=328.0.

Step 2: preparation of tert-butyl 8-((tert-butoxycarbonyl) (2-hydroxyethyl)amino)-2-chloro-7,8-dihydro-1,6-naphthyridine-6(5H)-carboxylate Tert-butyl 2-chloro-8-((2-hydroxyethyl)amino)-7,8-dihydro-1,6-naphthyridine-6(5H)-carboxylate (53 mg) was dissolved in methylene chloride (4 mL) at room temperature, triethylamine (32 mg) and di-tert-butyl dicarbonate (53 mg) were added and the reaction was stirred overnight. LC-MS showed that the reaction was complete. Dichloromethane and water were added, the layers were separated, the aqueous layer was extracted with dichloromethane, and the organic phase was concentrated to dryness. The resulting crude product was purified by silica gel column chromatography to give the title compound (60 mg).

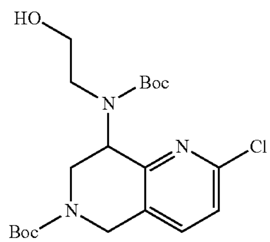 [SMILES: CC(C)(C)OC(=O)N1Cc2ccc(Cl)nc2C(N(CCO)C(=O)OC(C)(C)C)C1]

MS (ESI) m/z $(M+H)^+$=428.1.

Step 3: preparation of tert-butyl 8-((tert-butoxycarbonyl) (2-hydroxyethyl)amino)-2-cyano-7,8-dihydro-1,6-naphthyridine-6(5H)-carboxylate Tert-butyl 8-((tert-butoxycarbonyl) (2-hydroxyethyl) amino)-2-chloro-7,8-dihydro-1,6-naphthyridine-6(5H)-carboxylate (43 mg) was dissolved in N,N-dimethylformamide (5 mL) at room temperature, zinc cyanide (246 mg) and tetrakis(triphenylphosphine)palladium (808 mg) were added, the system was evacuated and backfilled with nitrogen (3 times), and the mixture was heated to 120° C. and stirred overnight. LC-MS showed completion of the reaction. The mixture was filtered, added with ethyl acetate and water, the layers were separated, the aqueous layer was extracted 3 times with ethyl acetate, the organic phase was dried and concentrated, and the resulting crude product was purified by pre-TLC to give the title compound (30 mg).

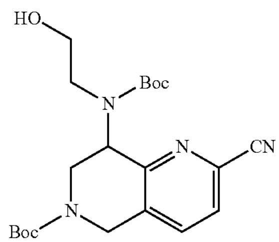 [SMILES: CC(C)(C)OC(=O)N1Cc2ccc(C#N)nc2C(N(CCO)C(=O)OC(C)(C)C)C1]

MS (ESI) m/z $(M+H)^+$=419.1.

Step 4: preparation of 8-((2-hydroxyethyl)amino)-5,6,7,8-tetrahydro-1,6-naphthyridine-2-carboxylic acid dihydrochloride Tert-butyl 8-((tert-butoxycarbonyl) (2-hydroxyethyl) amino)-2-cyano-7,8-dihydro-1,6-naphthyridine-6(5H)-carboxylate (30 mg) was weighed out and dissolved in 6M aqueous hydrochloric acid (5 mL). The system was heated to 120° C. for 5 hours. LC-MS showed the reaction was complete. The reaction was concentrated and the residue was purified by pre-HPLC to give the title compound (15.8 mg).

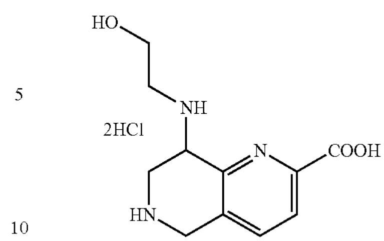

MS (ESI) m/z $(M+H)^+$=238.0.

$^1$H NMR (400 MHz, Deuterium Oxide) δ 8.20 —7.78 (m, 2H), 4.97 (s, 1H), 4.53 (s, 2H), 4.18 (d, J=12.0 Hz, 1H), 3.87 (s, 2H), 3.70 (d, J=12.0 Hz, 1H), 3.34 (d, J=28.0 Hz, 2H).

Example 5: preparation of 8-morpholino-5,6,7,8-tetrahydro-1,6-naphthyridine-2-carboxylic acid hydrochloride

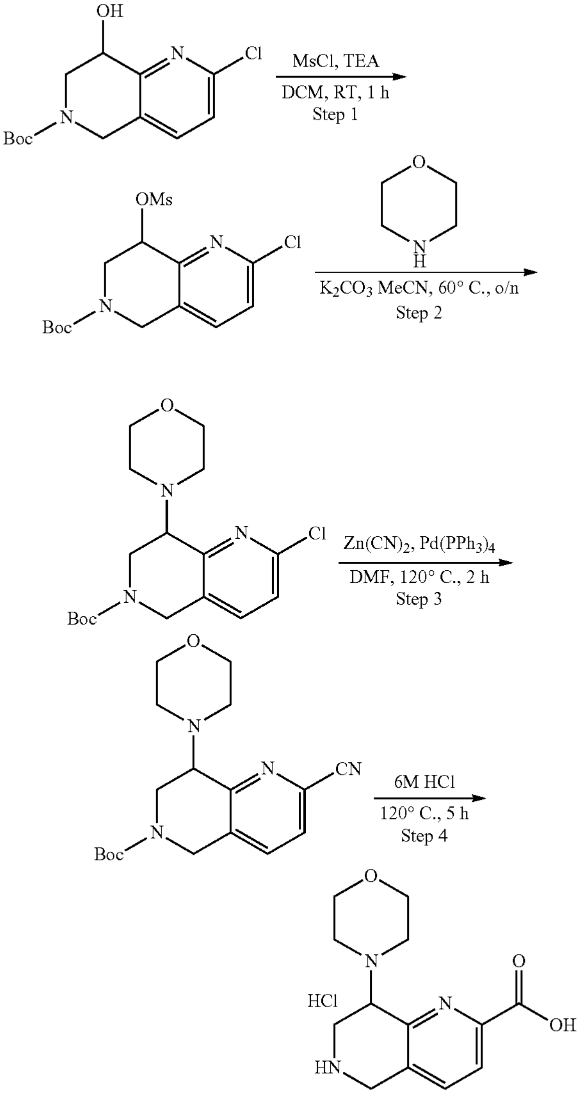

Step 1: preparation of tert-butyl 2-chloro-8-((methylsulfonyl)oxy)-7,8-dihydro-1,6-naphthyridine-6(5H)-carboxylate Tert-butyl 2-chloro-8-hydroxy-7,8-dihydro-1,6-naphthyridine-6(5H)-carboxylate (270 mg) was weighed out and dissolved in dichloromethane (8 ml), and triethylamine (300 mg) was added under ice-bath cooling. The system was evacuated and backfilled with nitrogen (3 times), methanesulfonyl chloride (230 mg) was added dropwise thereto, and the reaction was allowed to proceed at room temperature for 1 hour, and LC-MS showed completion of the reaction. Dichloromethane and water were added, the layers were separated and the aqueous layer was extracted, and the organic phase was concentrated to dryness to give the title compound (310 mg).

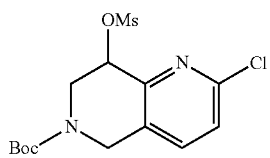 [SMILES: CC(C)(C)OC(=O)N1Cc2ccc(Cl)nc2C(OS(C)(=O)=O)C1]

MS (ESI) m/z $(M+H)^+$=363.1.

Step 2: preparation of tert-butyl 2-chloro-8-morpholino-7,8-dihydro-1,6-naphthyridine-6(5H)-carboxylate Tert-butyl 2-chloro-8-((methanesulfonyl)oxy)-7,8-dihydro-1,6-naphthyridine-6(5H)-carboxylate (150 mg) was weighed out and dissolved in N,N-dimethylformamide (2 ml) and acetonitrile (2 ml), potassium carbonate (138 mg) and morpholine (174 mg) were added. The reaction was heated to 60° C. overnight and TLC showed completion of the reaction. Ethyl acetate and water were added, the layers were separated and the aqueous layer was extracted, and the organic phase was concentrated to dryness. The resulting crude product was purified by column chromatography to give the title compound (120 mg).

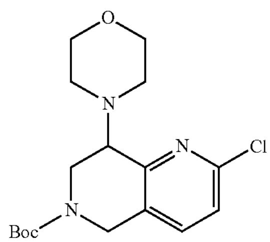 [SMILES: CC(C)(C)OC(=O)N1Cc2ccc(Cl)nc2C(N2CCOCC2)C1]

MS (ESI) m/z $(M+H)^+$=354.1.

Step 3: preparation of tert-butyl 2-cyano-8-morpholino-7,8-dihydro-1,6-naphthyridine-6(5H)-carboxylate Tert-butyl 2-chloro-8-morpholino-7,8-dihydro-1,6-naphthyridine-6(5H)-carboxylate (120 mg) was weighed out and dissolved in N,N-dimethylformamide (5 mL), zinc cyanide (318 mg) and tetrakis(triphenylphosphine)palladium (196 mg) were added, the system was evacuated and backfilled with nitrogen (3 times), and the mixture was heated to 120° C. for 2 hours. LC-MS showed completion of the reaction. Ethyl acetate and water were added, the aqueous layer was extracted 3 times with ethyl acetate, and the organic phase was dried and concentrated to dryness. The residue was purified by column chromatography to give the title compound (100 mg).

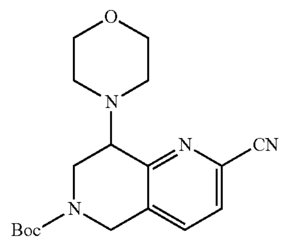 [SMILES: CC(C)(C)OC(=O)N1Cc2ccc(C#N)nc2C(N2CCOCC2)C1]

MS (ESI) m/z $(M+H)^+$=345.1.

Step 4: preparation of 8-morpholino-5,6,7,8-tetrahydro-1,6-naphthyridine-2-carboxylic acid hydrochloride Tert-butyl 2-cyano-8-morpholino-7,8-dihydro-1,6-naphthyridine-6(5H)-carboxylate (42 mg) was weighed out and dissolved in 6M aqueous hydrochloric acid (4 mL). The system was heated to 120° C. for 5 hours. LC-MS showed the reaction was complete. The reaction was concentrated and the residue was purified by pre-HPLC to give the title compound (31 mg).

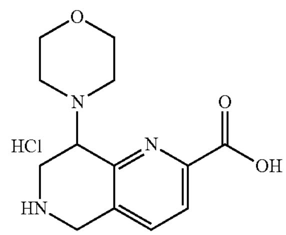

MS (ESI) m/z $(M+H)^+$=264.0.

$^1$H NMR (400 MHz, Deuterium Oxide) δ7.90 (d, J=8.0 Hz, 1H), 7.80 (d, J=8.1 Hz, 1H), 4.63-4.35 (m, 3H), 3.83 (q, J=4.8, 3.7 Hz, 6H), 2.96 (tq, J=12.4, 7.4, 6.0 Hz, 4H).

Example 6: preparation of 8-(1,1-dioxido-thiomorpholino)-5,6,7,8-tetrahydro-1,6-naphthyridine-2-carboxylic acid hydrochloride

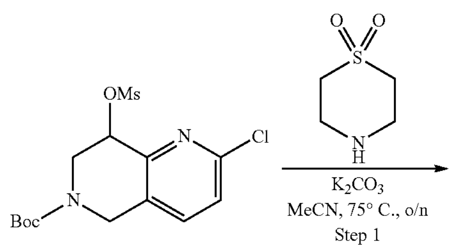

-continued

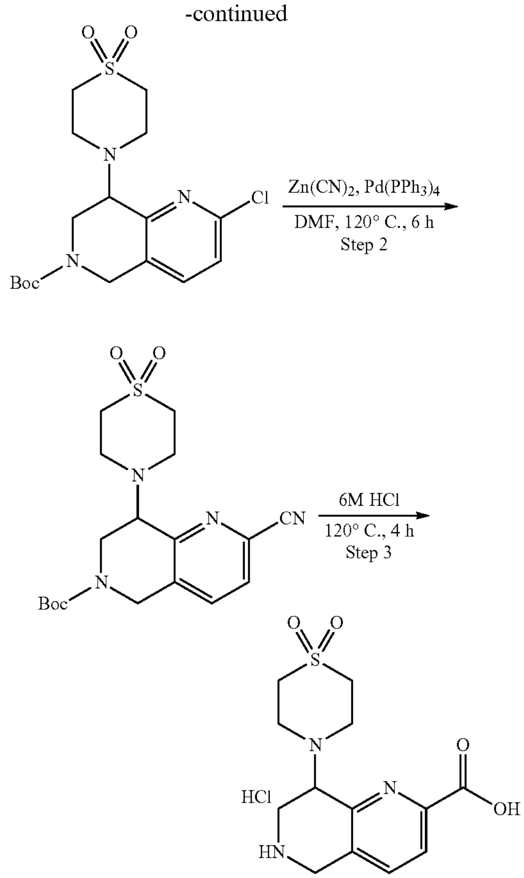

Step 1: preparation of tert-butyl 2-chloro-8-(1,1-dioxido-thiomorpholino)-7,8-dihydro-1,6-naphthyridine-6(5H)-carboxylate Tert-butyl 2-chloro-8-((methanesulfonyl)oxy)-7,8-dihydro-1,6-naphthyridine-6(5H)-carboxylate (65 mg) was weighed out and dissolved in acetonitrile (5 mL), and thiomorpholine 1,1-dioxide (540 mg) and potassium carbonate (550 mg) were added successively. The temperature was allowed to raise to 75° C. overnight and TLC showed substantial completion of the reaction. Ethyl acetate and water were added, the layers were separated and the aqueous layer was extracted, and the organic phase was concentrated to dryness. The resulting crude product was purified by column chromatography to give the title compound (28 mg).

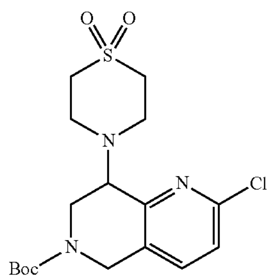 [SMILES: CC(C)(C)OC(=O)N1Cc2ccc(Cl)nc2C(N2CCS(=O)(=O)CC2)C1]

MS (ESI) m/z $(M+H)^+$=402.1.

Step 2: preparation of tert-butyl 2-cyano-8-(1,1-dioxido-thiomorpholino)-7,8-dihydro-1,6-naphthyridine-6(5H)-carboxylate Tert-butyl 2-chloro-8-(1,1-dioxido-thiomorpholino)-7,8-dihydro-1,6-naphthyridine-6(5H)-carboxylate (28 mg) was weighed out and dissolved in N,N-dimethylformamide (2.5 mL), and zinc cyanide (82 mg) and tetrakis(triphenylphosphine)palladium (81 mg) were added successively. The system was evacuated and backfilled with nitrogen (3 times), and the reaction was carried out at 120° C. for 6 hours. TLC showed substantial completion of the reaction. Ethyl acetate was added and the mixture was suction filtered, the filtrate was washed with aqueous ammonium chloride, the organic phase was concentrated to dryness and the resulting crude product was purified by column chromatography to give the title compound (25 mg).

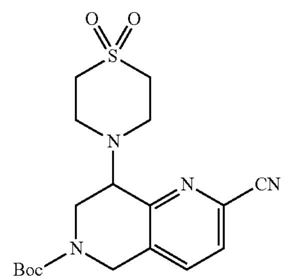 [SMILES: CC(C)(C)OC(=O)N1Cc2ccc(C#N)nc2C(N2CCS(=O)(=O)CC2)C1]

MS (ESI) m/z $(M+H)^+$=393.1.

Step 3: preparation of 8-(1,1-dioxido-thiomorpholino)-5,6,7,8-tetrahydro-1,6-naphthyridine-2-carboxylic acid hydrochloride Tert-butyl 2-cyano-8-(1,1-dioxido-thiomorpholino)-7,8-dihydro-1,6-naphthyridine-6(5H)-carboxylate (25 mg) was weighed out and added with 6M hydrochloric acid (2.5 mL). The reaction was carried out under sealed condition at 120° C. for 4 hours, and TLC showed substantial completion of the reaction. The system was concentrated to dryness and the residue was purified by pre-HPLC to give the title compound (4.5 mg).

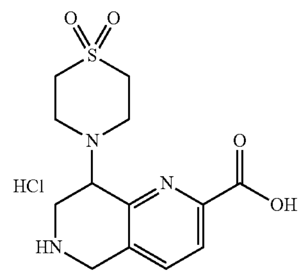 [SMILES: Cl ; O=C(O)c1ccc2c(n1)C(N1CCS(=O)(=O)CC1)CNC2]

MS (ESI) m/z $(M+H)^+$=312.0.

$^1$H NMR (400 MHz, Deuterium Oxide) δ 7.81 (d, J=8.1 Hz, 1H), 7.74 (d, J=8.1 Hz, 1H), 4.54-4.35 (m, 2H), 4.32 (dd, J=6.2, 4.3 Hz, 1H), 3.68 (dd, J=13.2, 6.2 Hz, 1H), 3.59 (dd, J=13.2, 4.3 Hz, 1H), 3.29-3.12 (m, 4H), 3.04 (dt, J=7.5, 3.7 Hz, 4H).

Example 7: preparation of 7-((3-hydroxypropoxy)methyl)-5,6,7,8-tetrahydro-1,6-naphthyridine-2-carboxylic acid hydrochloride

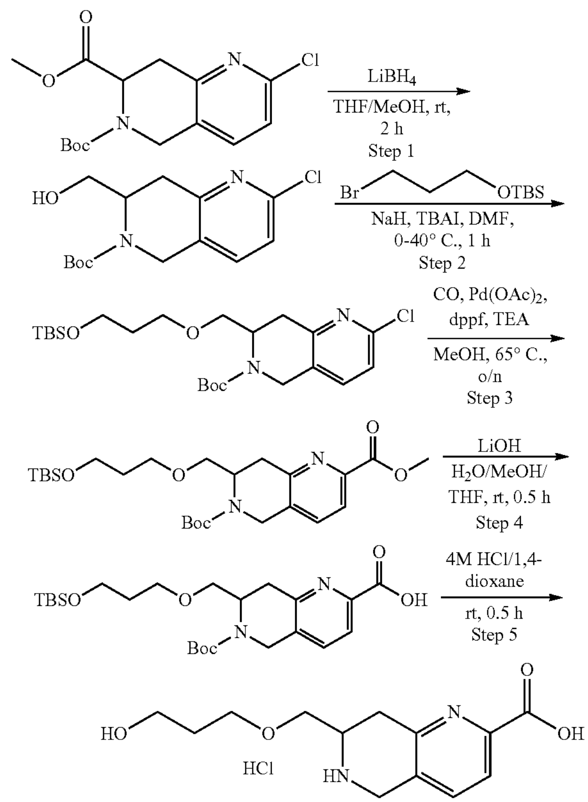

Step 1: preparation of tert-butyl 2-chloro-7-(hydroxymethyl)-7,8-dihydro-1,6-naphthyridine-6-(5H)-carboxylate 6-(Tert-butyl) 7-methyl 2-chloro-7,8-dihydro-1,6-naphthyridine-6,7(5H)-dicarboxylate (1.00 g) was dissolved in tetrahydrofuran (20 mL)/methanol (1 mL) at room temperature, lithium borohydride (0.340 g) was added under ice-bath cooling, and the reaction was stirred for 2 hours. LCMS showed completion of the reaction. Saturated ammonium chloride solution was added dropwise under ice-bath cooling to quench the reaction, ethyl acetate and water were added, the layers were separated and the aqueous layer was extracted with ethyl acetate. The combined organic phase was dried over anhydrous sodium sulfate, filtered, and the solvent was removed under reduced pressure. The obtained crude product was purified by silica gel column chromatography to give the title compound (0.90 g).

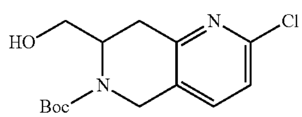 [SMILES: CC(C)(C)OC(=O)N1Cc2ccc(Cl)nc2CC1CO]

MS (ESI) m/z $(M+H)^+$=299.0.

Step 2: preparation of tert-butyl 7-((3-((tert-butyldimethylsilyl)oxy)propoxylmethyl)-2-chloro-7,8-dihydro-1,6-naphthyridine-6(5H)-carboxylate Sodium hydride (0.024 g) was charged to a reaction flask at room temperature, N,N-dimethylformamide (2 mL) was added under nitrogen atmosphere, and the system was cooled in an ice bath for 10 minutes. 3-Bromopropoxy tert-butyldimethylsilane (1.77 g) was added, and then tert-butyl 2-chloro-7-(hydroxymethyl)-7,8-dihydro-1,6-naphthyridine-6-(5H)-carboxylate (208 mg) and tetrabutylammonium iodide (26 mg) were added. After completion of the addition, the mixture was heated to 40° C. and stirred for 1 hour, and TLC indicated completion of the reaction. Saturated ammonium chloride solution was added dropwise under ice-bath cooling to quench the reaction, ethyl acetate and water were added, the layers were separated and the aqueous layer was extracted with ethyl acetate. The organic phase was washed with saturated ammonium chloride solution. The combined organic phase was dried over anhydrous sodium sulfate, filtered, and concentrated under reduced pressure. The obtained crude product was purified by silica gel column chromatography to give the title compound (40 mg).

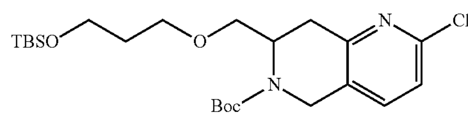 [SMILES: CC(C)(C)OC(=O)N1Cc2ccc(Cl)nc2CC1COCCCO[Si](C)(C)C(C)(C)C]

MS (ESI) m/z $(M+H)^+$=471.1.

Step 3: preparation of 6-(tert-butyl) 2-methyl 7-((3-((tert-butyldimethylsilyl)oxy)propoxylmethyl)-7,8-dihydro-1,6-naphthyridine-2,6(5H)-dicarboxylate Tert-butyl 7-((3-((tert-butyldimethylsilyl)oxy)propoxylmethyl)-2-chloro-7,8-dihydro-1,6-naphthyridine-6 (5H)-carboxylate (37 mg) was dissolved in methanol (20 mL) at room temperature, palladium acetate (9 mg), 1',1-bis(diphenylphosphino)ferrocene (44 mg) and triethylamine (8 mg) were added. After the addition was complete, the system was purged with carbon monoxide, then heated to 65° C. and stirred overnight under carbon monoxide atmosphere. LCMS showed that the reaction was complete, and the solvent was removed under reduced pressure. The obtained crude product was purified by pre-TLC to give the title compound (33 mg).

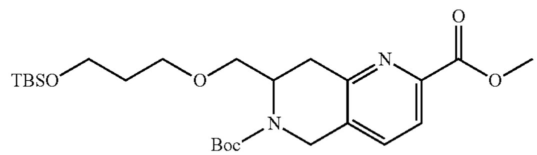 [SMILES: COC(=O)c1ccc2c(n1)CC(COCCCO[Si](C)(C)C(C)(C)C)N(C(=O)OC(C)(C)C)C2]

MS (ESI) m/z (M+H)+=495.0.

Step 4: preparation of 6-(tert-butoxycarbonyl)-74(3-((tert-butyldimethylsilyl)oxy)propoxy)methyl)-5,6,7,8-tetrahydro-1,6-naphthyridine-2-carboxylic acid 6-(Tert-butyl) 2-methyl 7-((3-((tert-butyldimethylsilyl)oxy)propoxy) methyl)-7,8-dihydro-1,6-naphthyridine-2,6

(5H)-dicarboxylate (58 mg) was dissolved in tetrahydrofuran (1 mL)/methanol (1 mL)/water (1 mL) system at room temperature, lithium hydroxide monohydrate (10 mg) was added, and the system was stirred for 30 minutes. LCMS showed that the reaction was complete. The reaction mixture was made weakly acidic with hydrogen chloride in 1,4-dioxane (4M), and concentrated under reduced pressure. The crude title compound was obtained and used directly in the next step.

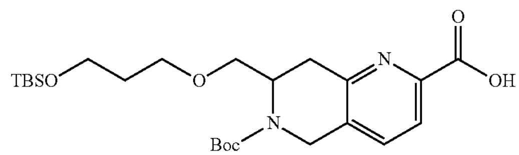 [SMILES: CC(C)(C)OC(=O)N1Cc2ccc(C(=O)O)nc2CC1COCCCO[Si](C)(C)C(C)(C)C]

MS (ESI) m/z $(M+H)^+$=481.1.

Step 5: preparation of 7-(3-hydroxypropoxy) methyl)-5,6,7,8-tetrahydro-1,6-naphthyridine-2-carboxylic acid hydrochloride The crude 6-(tert-butoxycarbonyl)-74(3-((tert-butyldimethylsilyl)oxy)propoxy) methyl)-5,6,7,8-tetrahydro-1,6-naphthyridine-2-carboxylic acid obtained in step 4 was added to a solution of hydrogen chloride in 1,4-dioxane (4M, 2 mL) at room temperature and stirred for 30 minutes. LCMS showed that the reaction was complete. The reaction mixture was concentrated under reduced pressure, and the residue was purified by pre-HPLC to give the title compound (28.3 mg).

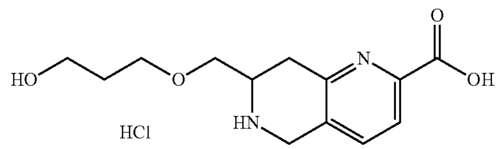 [SMILES: O=C(O)c1ccc2c(n1)CC(COCCCO)NC2 ; Cl]

MS (ESI) m/z $(M+H)^+$=267.1.

$^1H$ NMR (400 MHz, Deuterium Oxide) δ 7.69 (s, 2H), 4.44 (s, 2H), 3.98-3.80 (m, 2H), 3.70-3.56 (m, 5H), 3.14 (dd, J=17.4, 7.9 Hz, 2H), 1.77 (p, J=6.3 Hz, 2H).

Example 8: preparation of 7-carbamoyl-5,6,7,8-tetrahydro-1,6-naphthyridine-2-carboxylic acid hydrochloride

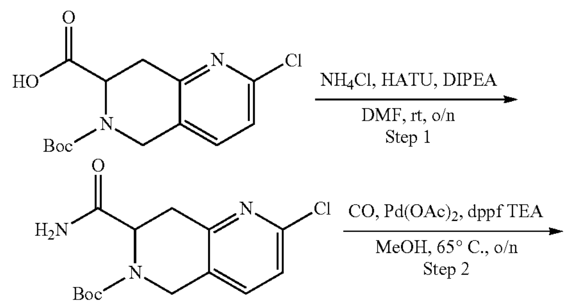

-continued

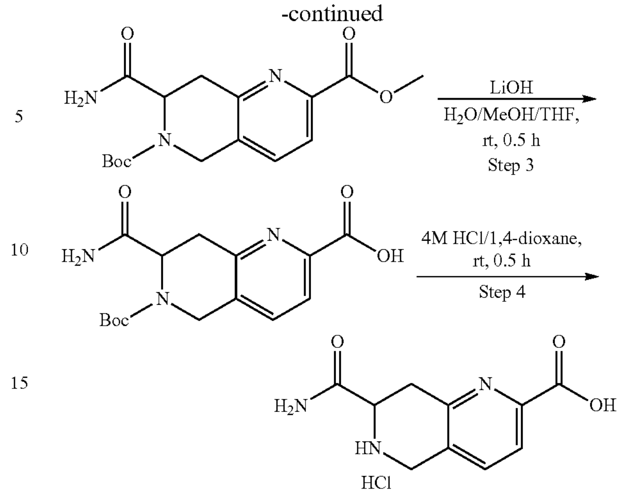

Step 1: preparation of tert-butyl 7-carbamoyl-2-chloro-7,8-dihydro-1,6-naphthyridine-6-(5H)-carboxylate 6-(tert-butoxycarbonyl)-2-chloro-5,6,7,8-tetrahydro-1,6-naphthyridine-7-carboxylic acid (86 mg) was dissolved in N,N-dimethylformamide (4 mL) at room temperature, 2-(7-azabenzotriazol-1-yl)-N,N,N',N'-tetramethyluronium hexafluorophosphate (157 mg), ammonium chloride (87 mg) and N,N-diisopropylethylamine (356 mg) were added successively under ice-bath cooling. After completion of the addition, the reaction was stirred overnight at room temperature, and LCMS indicated completion of the reaction. Sodium bicarbonate solution was added, the mixture was extracted with ethyl acetate and the extract was washed with saturated ammonium chloride solution. The organic phases were combined, dried over anhydrous sodium sulfate, filtered, concentrated under reduced pressure, and the resulting crude product was purified by pre-TLC to give the title compound (46 mg).

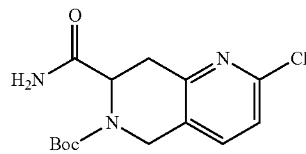 [SMILES: CC(C)(C)OC(=O)N1Cc2ccc(Cl)nc2CC1C(N)=O]

MS (ESI) m/z $(M+H)^+$=312.0.

Step 2: preparation of 6-(tert-butyl) 2-methyl 7-carbamoyl-7,8-dihydro-1,6-naphthyridine-2,6(5H)-dicarboxylate Tert-butyl 7-carbamoyl-2-chloro-7,8-dihydro-1,6-naphthyridine-6-(5H)-carboxylate (40 mg) was dissolved in methanol (20 mL) at room temperature, palladium acetate (15 mg), 1,1'-bis(diphenylphosphino)ferrocene (72 mg) and triethylamine (65 mg) were added, and after completion of addition, the system was purged with carbon monoxide, and then heated to 65° C. and stirred overnight under carbon monoxide atmosphere. The reaction was completed as detected by LCMS, and the reaction mixture was concentrated under reduced pressure. The crude product was purified by pre-TLC to give the title compound (39 mg).

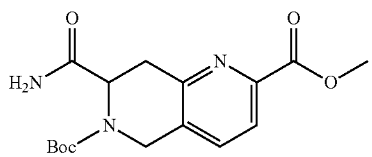 [SMILES: COC(=O)c1ccc2c(n1)CC(C(N)=O)N(C(=O)OC(C)(C)C)C2]

MS (ESI) m/z $(M+H)^+$=336.0.

Step 3: preparation of 6-(tert-butoxycarbonyl)-7-carbamoyl-5,6,7,8-tetrahydro-1,6-naphthyridine-2-carboxylic acid 6-(tert-butyl) 2-methyl 7-carbamoyl-7,8-dihydro-1,6-naphthyridine-2,6(5H)-dicarboxylate (39 mg) was dissolved in tetrahydrofuran (1 mL)/methanol (1 mL)/water (1 mL) system at room temperature, lithium hydroxide monohydrate (10 mg) was added and the mixture was stirred for 30 min The reaction was completed as detected by LCMS, and the reaction mixture was concentrated under reduced pressure to give crude title compound.

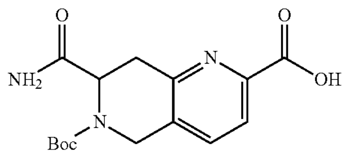 [SMILES: CC(C)(C)OC(=O)N1Cc2ccc(C(=O)O)nc2CC1C(N)=O]

MS (ESI) m/z $(M+H)^+$=322.0.

Step 4: preparation of 7-carbamoyl-5,6,7,8-tetrahydro-1,6-naphthyridine-2-carboxylic acid hydrochloride The crude 6-(tert-butoxycarbonyl)-7-carbamoyl-5,6,7,8-tetrahydro-1,6-naphthyridine-2-carboxylic acid obtained in step 3 was added to a solution of hydrogen chloride in 1,4-dioxane (4M, 2 mL) at room temperature and stirred for 30 minutes. LCMS showed that the reaction was complete. The reaction mixture was concentrated under reduced pressure, and the residue was purified by pre-HPLC to give the title compound (10 mg).

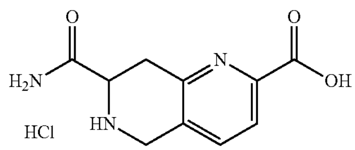 [SMILES: Cl ; NC(=O)C1Cc2nc(C(=O)O)ccc2CN1]

MS (ESI) m/z $(M+H)^+$=222.1.

$^1$H NMR (400 MHz, Deuterium Oxide) δ 8.16-7.86 (m, 2H), 4.63-4.58 (m, 1H), 4.55-4.42 (m, 2H), 3.74-3.49 (m, 1H), 3.46-3.22 (m, 1H).

Example 9: preparation of 7-(1-hydroxycyclopropyl)-5,6,7,8-tetrahydro-1,6-naphthyridine-2-carboxylic acid hydrochloride

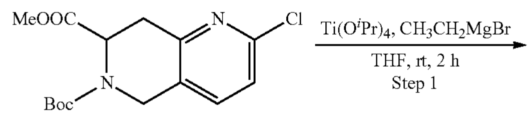

-continued

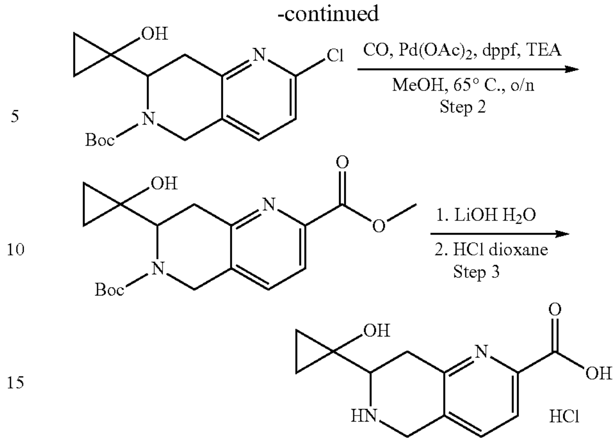

Step 1: preparation of tert-butyl 2-chloro-7-(1-hydroxycyclopropyl)-7,8-dihydro-1,6-naphthyridine-6(5H)-carboxylate 6-(Tert-butyl) 7-methyl 2-chloro-7,8-dihydro-1,6-naphthyridine-6,7(5H)-dicarboxylate (98 mg) and tetraisopropyl titanate (85 mg) were added into a dry reaction flask, the system was evacuated and backfilled with nitrogen (3 times), and tetrahydrofuran (2.5 mL) was injected. A solution of ethylmagnesium bromide in tetrahydrofuran (1.2 mL, 1.0M) was slowly added dropwise under ice-bath cooling, and the system was slowly warmed to room temperature and reacted for 2 hours. TLC showed the reaction was complete. Saturated aqueous ammonium chloride solution was added to quench the reaction, ethyl acetate and water were added, the aqueous layer was separated and extracted, and the organic phase was concentrated to dryness. The resulting crude product was purified by column chromatography to give the title compound (50 mg).

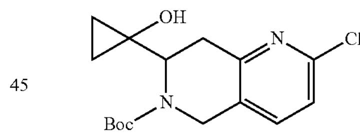

MS (ESI) m/z $(M+H)^+$=325.1.

Step 2: preparation of 6-(tert-butyl) 2-methyl 7-(1-hydroxycyclopropyl)-7,8-dihydro-1,6-naphthyridine-2,6(5H)-dicarboxylate Tert-butyl 2-chloro-7-(1-hydroxycyclopropyl)-7,8-dihydro-1,6-naphthyridine-6(5H)-carboxylate (50 mg) was weighed out and dissolved in methanol (8 mL), and palladium acetate (17 mg), 1,1'-bis(diphenylphosphino)ferrocene (83 mg), and triethylamine (76 mg) were added successively. The system was purged with carbon monoxide, and then reacted at 65° C. overnight under carbon monoxide atmosphere. TLC showed substantial completion of the reaction. The reaction mixture was concentrated to dryness under reduced pressure, and the resulting crude product was purified by column chromatography to give the title compound (40 mg).

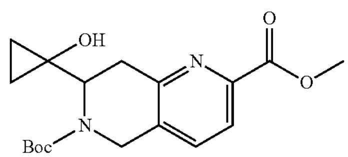 [SMILES: COC(=O)c1ccc2c(n1)CC(C1(O)CC1)N(C(=O)OC(C)(C)C)C2]

MS (ESI) m/z $(M+H)^+$=349.1.

Step 3: preparation of 7-(1-hydroxycyclopropyl)-5,6,7,8-tetrahydro-1,6-naphthyridine-2-carboxylic acid hydrochloride 6-(Tert-butyl) 2-methyl 7-(1-hydroxycyclopropyl)-7,8-dihydro-1,6-naphthyridine-2,6(5H)-dicarboxylate (40 mg) was weighed out and dissolved in a mixture of methanol (2 mL), tetrahydrofuran (2 mL) and water (2 mL), and lithium hydroxide monohydrate (10 mg) was added. The reaction was allowed to proceed at room temperature for 1 hour, and TLC showed substantial completion of the reaction. The system was concentrated to dryness, methylene chloride (3 mL) and hydrogen chloride in 1,4-dioxane (1 mL, 4.0M) were added and the reaction was allowed to proceed at room temperature for 1 hour, TLC indicated substantial completion of the reaction. The system was concentrated to dryness and purified by pre-HPLC to give the title compound (14.8 mg).

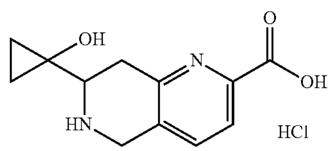 [SMILES: O=C(O)c1ccc2c(n1)CC(C1(O)CC1)NC2 ; Cl]

MS (ESI) m/z $(M+H)^+$=235.1.

$^1$H NMR (400 MHz, Deuterium Oxide) δ 7.71 (s, 2H), 4.43 (s, 2H), 3.29 (d, J=15.6 Hz, 1H), 3.21 (s, 2H), 0.9 (s, 2H), 0.74 (s, 2H).

Example 10: preparation of 7-(4-hydroxybutyl)-5,6,7,8-tetrahydro-1,6-naphthyridine-2-carboxylic acid hydrochloride

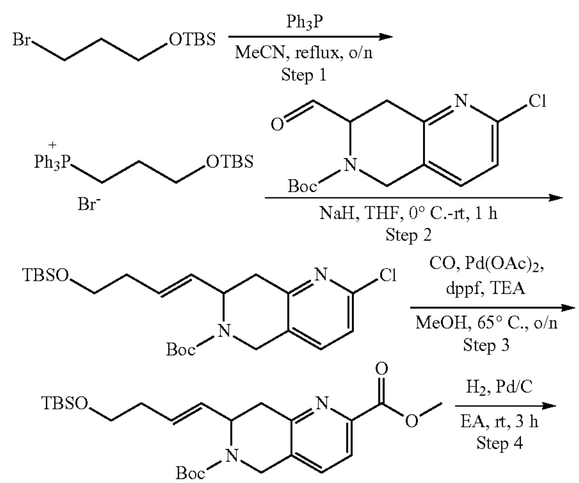

-continued

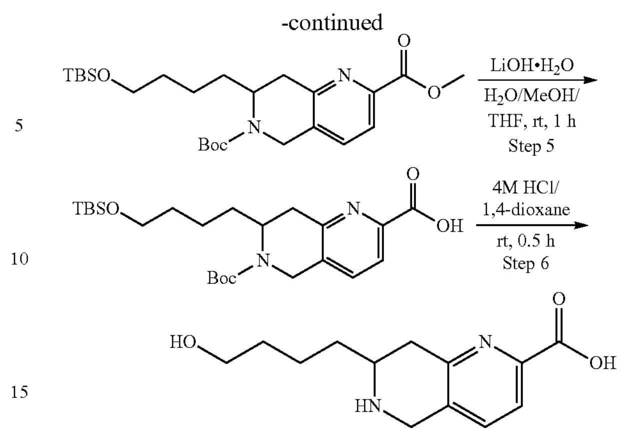

Step 1: preparation of (3-((tert-butyldimethylsilyl)oxy)propyl)triphenylphosphonium bromide 3-Bromopropoxy tert-butyldimethylsilane (1.012 g) and triphenylphosphine (1.048 g) were dissolved in acetonitrile (15 mL) at room temperature, the reaction was warmed to 80° C. and stirred overnight. LCMS showed completion of the reaction, and the reaction mixture was concentrated under reduced pressure. The resulting crude product was purified by silica gel column chromatography to give the title compound (1.176 g).

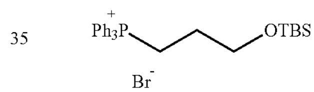

MS (ESI) m/z $(M+H)^+$=435.2.

Step 2: preparation of tert-butyl 7-(4-((tert-butyldimethylsilyl)oxy)but-1-en-1-yl)-2-chloro-7,8-dihydro-1,6-naphthyridine-6(5H)-carboxylate (3-((Tert-butyldimethylsilyloxy)propyl)triphenylphosphonium bromide (178 mg) was dissolved in tetrahydrofuran under nitrogen atmosphere, sodium hydride (8 mg) was added under ice-bath cooling and stirred for 30 minutes. Tert-butyl 2-chloro-7-formyl-7,8-dihydro-1,6-naphthyridine-6(5H)-carboxylate (96 mg) was added and the reaction was checked for completion by LCMS. The reaction system was placed in an ice bath, quenched by adding water dropwise, extracted with ethyl acetate. The organic phases were combined, dried over anhydrous sodium sulfate, filtered and concentrated under reduced pressure. The resulting crude product was purified by silica gel column chromatography to give the title compound (38 mg).

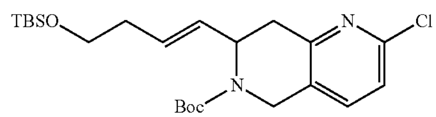 [SMILES: CC(C)(C)OC(=O)N1Cc2ccc(Cl)nc2CC1/C=C/CCO[Si](C)(C)C(C)(C)C]

MS (ESI) m/z $(M+H-Boc)^+$=353.1.

Step 3: preparation of 6-(tert-butyl) 2-methyl 7-(4-((tert-butyldimethylsilyl)oxy)but-1-en-1-yl)-7,8-dihydro-1,6-naphthyridine-2,6(5H)-dicarboxylate At room temperature, tert-butyl 7-(4-((tert-butyldimethylsilyl)oxy)but-1-en-1-yl)-2-chloro-7,8-dihydro-1,6-naphthyridine-6(5H)-carboxylate (36 mg) was dissolved in methanol (20 mL), palladium acetate (9 mg), 1,1'-bis(diphenylphosphino)ferrocene (44 mg) and triethylamine (16 mg) were added. After completion of addition, the system was purged with carbon monoxide, then heated to 65° C. and stirred overnight under carbon monoxide atmosphere. LCMS showed that the reaction was complete, and the reaction mixture was concentrated under reduced pressure. The resulting crude product was purified by pre-TLC to give the title compound (26 mg).

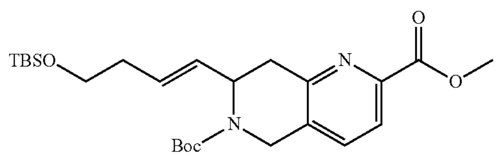 [SMILES: COC(=O)c1ccc2c(n1)CC(/C=C/CCO[Si](C)(C)C(C)(C)C)N(C(=O)OC(C)(C)C)C2]

MS (ESI) m/z $(M+H)^+$=477.2.

Step 4: preparation of 6-(tert-butyl) 2-methyl 7-(4-((tert-butyldimethylsilyl)oxy) butyl)-7,8-dihydro-1,6-naphthyridine-2,6(5H)-dicarboxylate 6-(Tert-butyl) 2-methyl 7-(4-((tert-butyldimethylsilyl)oxy)but-1-en-1-yl)-7,8-dihydro-1,6-naphthyridine-2,6(5H)-dicarboxylate (26 mg) was dissolved in ethyl acetate (20 mL) at room temperature, palladium on carbon (5 mg) was added, the system was purged with hydrogen and stirred under hydrogen atmosphere for 3 hours. LCMS showed completion of the reaction, the mixture was filtered and concentrated under reduced pressure to give the crude title compound (25 mg).

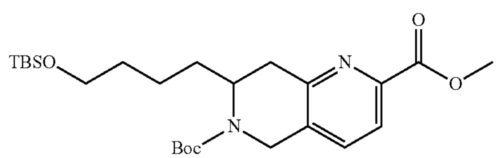 [SMILES: COC(=O)c1ccc2c(n1)CC(CCCCO[Si](C)(C)C(C)(C)C)N(C(=O)OC(C)(C)C)C2]

MS (ESI) m/z $(M+H)^+$=479.3.

Step 5: preparation of 6-(tert-butoxycarbonyl)-7-(4-((tert-butyldimethylsilyl)oxy) butyl)-5,6,7,8-tetrahydro-1,6-naphthyridine-2-carboxylic acid At room temperature, 6-(tert-butyl) 2-methyl 7-(4-((tert-butyldimethylsilyl)oxy) butyl)-7,8-dihydro-1,6-naphthyridine-2,6(5H)-dicarboxylate (25 mg) was dissolved in tetrahydrofuran (1 mL)/methanol (1 mL)/water (1 mL) system, lithium hydroxide monohydrate (21 mg) was added and the reaction was stirred for 1 hour. LC-MS showed completion of the reaction. The system was adjusted to weakly acidic with hydrogen chloride in 1,4-dioxane (4M), and concentrated under reduced pressure to obtain the crude title compound.

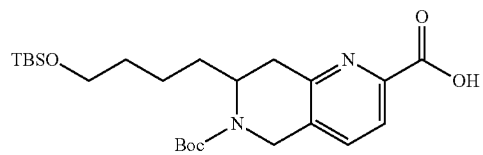 [SMILES: CC(C)(C)OC(=O)N1Cc2ccc(C(=O)O)nc2CC1CCCCO[Si](C)(C)C(C)(C)C]

MS (ESI) m/z $(M+H)^+$=465.1.

Step 6: preparation of 7-(4-hydroxybutyl)-5,6,7,8-tetrahydro-1,6-naphthyridine-2-carboxylic acid hydrochloride The crude 6-(tert-butoxycarbonyl)-7-(4-((tert-butyldimethylsilyl)oxy) butyl)-5,6,7,8-tetrahydro-1,6-naphthyridine-2-carboxylic acid obtained in step 5 was added to hydrogen chloride in 1,4-dioxane (4M, 2 mL) at room temperature and stirred for 30 minutes. LCMS showed completion of the reaction. The reaction mixture was concentrated under reduced pressure, and the residue was purified by pre-HPLC to give the title compound (2.3 mg).

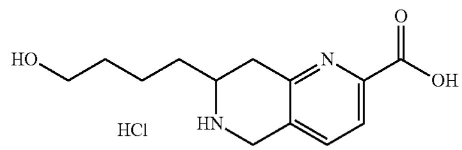 [SMILES: O=C(O)c1ccc2c(n1)CC(CCCCO)NC2 ; Cl]

MS (ESI) m/z (M+H)+=251.1.

1H NMR (400 MHz, Deuterium Oxide) δ 7.66 (s, 2H), 4.38 (s, 2H), 3.72-3.60 (m, 1H), 3.56 (t, J=6.1 Hz, 2H), 3.25 (dd, J=18.0, 4.8 Hz, 1H), 2.93 (dd, J=18.0, 10.8 Hz, 1H), 1.91-1.65 (m, 2H), 1.62-1.39 (m, 4H).

Example 11: preparation of 7-(((3-hydroxypropyl) amino)methyl)-5,6,7,8-tetrahydro-1,6-naphthyridine-2-carboxylic acid dihydrochloride

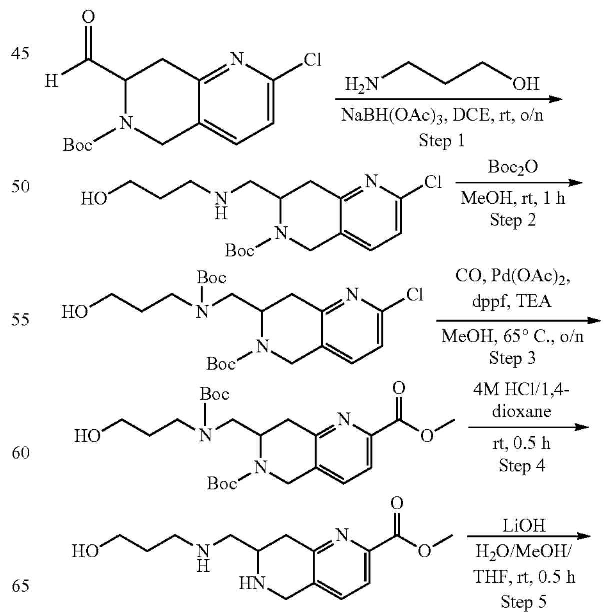

-continued

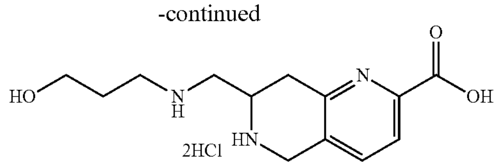

Step 1: preparation of tert-butyl 2-chloro-7-(((3-hydroxypropyl)amino) methyl)-7,8-dihydro-1,6-naphthyridine-6(5H)-carboxylate Tert-butyl 2-chloro-7-formyl-7,8-dihydro-1,6-naphthyridine-6(5H)-carboxylate (97 mg) was dissolved in 1,2-dichloroethane (5 mL) at room temperature, 3-amino-1-propanol (34 mg) was added and stirred for 30 minutes, then sodium triacetoxyborohydride (254 mg) was added and stirred overnight. LCMS showed completion of the reaction. The reaction mixture was diluted with water and dichloromethane (20 mL), washed with water, and extracted with dichloromethane. The organic phase was dried over anhydrous sodium sulfate, filtered, and concentrated under reduced pressure to give the crude title compound, which was used directly in the next reaction.

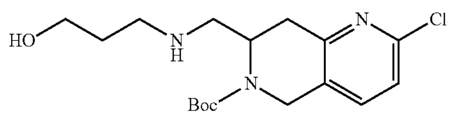 [SMILES: CC(C)(C)OC(=O)N1Cc2ccc(Cl)nc2CC1CNCCCO]

MS (ESI) m/z $(M+H)^+$=356.1.

Step 2: preparation of tert-butyl 7-(((tert-butoxycarbonyl)(3-hydroxypropyl)amino) methyl)-2-chloro-7,8-dihydro-1,6-naphthyridine-6(5H)-carboxylate Tert-butyl 2-chloro-7-(((3-hydroxypropyl)amino) methyl)-7,8-dihydro-1,6-naphthyridine-6(5H)-carboxylate from step 1 was dissolved in methanol (5 mL) at room temperature, di-tert-butyl dicarbonate (87 mg) was added and stirred for 1 hour. LCMS showed completion of the reaction. The reaction mixture was concentrated under reduced pressure, and the resulting crude product was purified by silica gel column chromatography to give the title compound (67 mg).

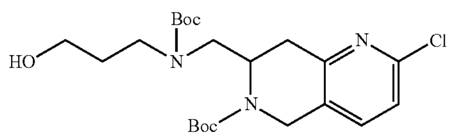 [SMILES: CC(C)(C)OC(=O)N(CCCO)CC1Cc2nc(Cl)ccc2CN1C(=O)OC(C)(C)C]

MS (ESI) m/z $(M+1)^+$=456.0.

Step 3: preparation of 6-(tert-butyl) 2-methyl 7-(((tert-butoxycarbonyl)(3-hydroxypropyl)amino) methyl)-7,8-dihydro-1,6-naphthyridine-2,6(5H)-dicarboxylate At room temperature, tert-butyl 7-(((tert-butoxycarbonyl) (3-hydroxypropyl)amino) methyl)-2-chloro-7,8-dihydro-1,6-naphthyridine-6(5H)-carboxylate (67 mg) was dissolved in methanol (20 mL), and palladium acetate (17 mg), 1,1'-bis(diphenylphosphino)ferrocene (81 mg) and triethylamine (30 mg) were added. After completion of the addition, the system was purged with carbon monoxide and stirred overnight at 65° C. under carbon monoxide atmosphere. LCMS showed completion of the reaction, and the reaction mixture was concentrated under reduced pressure. The resulting crude product was purified by pre-TLC to give the title compound (43 mg).

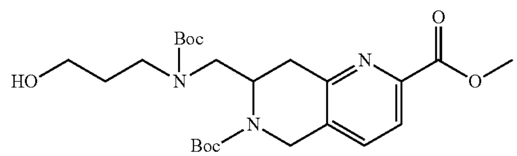 [SMILES: COC(=O)c1ccc2c(n1)CC(CN(CCCO)C(=O)OC(C)(C)C)N(C(=O)OC(C)(C)C)C2]

MS (ESI) m/z $(M+H)^+$=480.0.

Step 4: preparation of methyl 7-(((3-hydroxypropyl) amino) methyl)-5,6,7,8-tetrahydro-1,6-naphthyridine-2-carboxylate 6-(Tert-butyl) 2-methyl 7-(((tert-butoxycarbonyl)(3-hydroxypropyl)amino)methyl)-7,8-dihydro-1,6-naphthyridine-2,6(5H)-dicarboxylate (43 mg) was added to hydrogen chloride in 1,4-dioxane (4M, 2 mL) at room temperature and stirred for 30 min. LCMS showed completion of the reaction, and the reaction mixture was concentrated under reduced pressure to give the crude title compound.

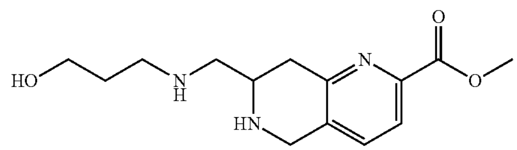 [SMILES: COC(=O)c1ccc2c(n1)CC(CNCCCO)NC2]

MS (ESI) m/z $(M+H)^+$=280.1.

Step 5: preparation of 7-(((3-hydroxypropyl) amino)methyl)-5,6,7,8-tetrahydro-1,6-naphthyridine-2-carboxylic acid hydrochloride The crude methyl 7-(((3-hydroxypropyl) amino)methyl)-5,6,7,8-tetrahydro-1,6-naphthyridine-2-carboxylate obtained in step 4 was dissolved in tetrahydrofuran (1 mL)/methanol (1 mL)/water (1 mL) system, lithium hydroxide monohydrate (38 mg) was added and stirred for 30 minutes. LCMS showed completion of the reaction, the reaction mixture was made weakly acidic with hydrogen chloride in 1,4-dioxane (4M), the solvent was removed under reduced pressure and the residue was purified by pre-HPLC to give the title compound (21.8 mg).

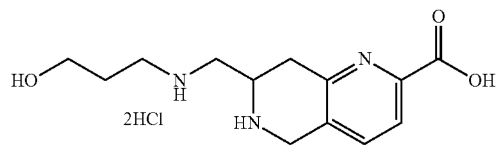 [SMILES: O=C(O)c1ccc2c(n1)CC(CNCCCO)NC2]

MS (ESI) m/z $(M+H)^+$=266.1.

$^1H$ NMR (400 MHz, Deuterium Oxide) δ 7.91 (s, 2H), 4.53-4.26 (m, 2H), 3.88 (s, 1H), 3.65 (t, J=5.8 Hz, 2H), 3.39 (d, J=29.3 Hz, 3H), 3.20 (s, 2H), 3.05 (s, 1H), 1.90 (s, 2H).

Example 12: preparation of 7-(hydroxy(phenyl) methyl)-5,6,7,8-tetrahydro-1,6-naphthyridine-2-carboxylic acid hydrochloride

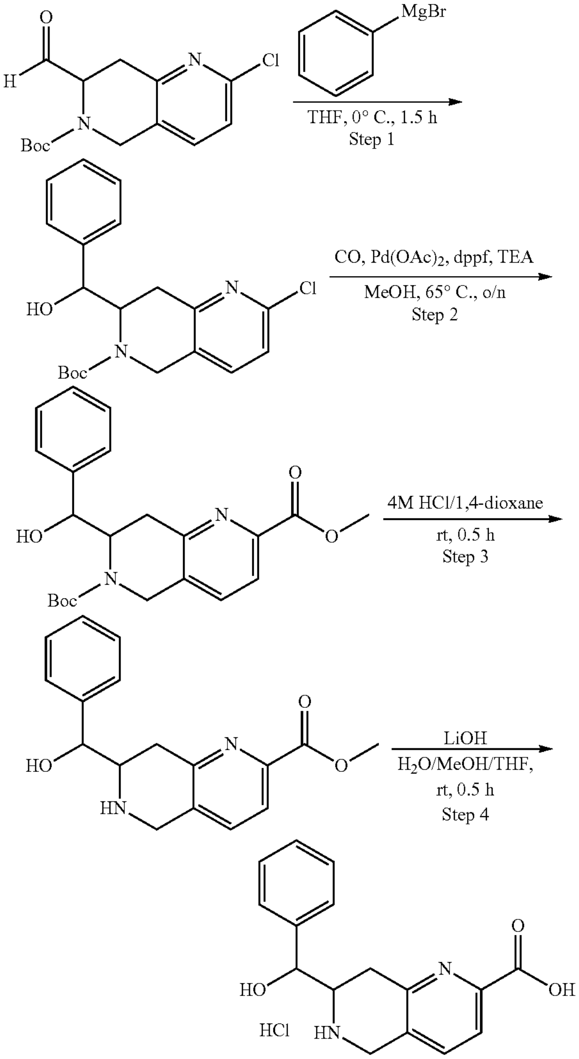

Step 1: preparation of tert-butyl 2-chloro-7-(hydroxy(phenyl)methyl)-7,8-dihydro-1,6-naphthyridine-6(5H)-carboxylate Tert-butyl 2-chloro-7-formyl-7,8-dihydro-1,6-naphthyridine-6(5H)-carboxylate (97 mg) was dissolved in tetrahydrofuran (10 mL) under nitrogen atmosphere, and phenylmagnesium bromide (0.42 mL) was added dropwise under ice-bath cooling and stirred for 1.5 h. LCMS showed completion of the reaction. The reaction was quenched by adding ammonium chloride solution, partitioned between water and ethyl acetate, and the water layer was extracted with ethyl acetate. The organic phases were combined, dried over anhydrous sodium sulfate, filtered, and concentrated under reduced pressure. The resulting crude product was purified by silica gel column chromatography to give the title compound (86 mg).

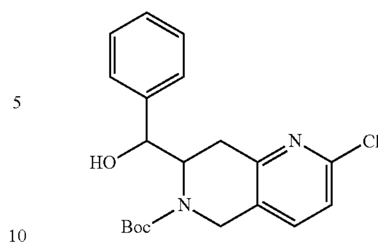

MS (ESI) m/z $(M+H)^+$=375.1.

Step 2: preparation of 6-(tert-butyl) 2-methyl 7-(hydroxy(phenyl)methyl)-7,8-dihydro-1,6-naphthyridine-2,6(5H)-dicarboxylate At room temperature, tert-butyl 2-chloro-7-(hydroxy(phenyl)methyl)-7,8-dihydro-1,6-naphthyridine-6(5H)-carboxylate (86 mg) was dissolved in methanol (20 mL), palladium acetate (23 mg), 1,1'-bis(diphenylphosphino)ferrocene (127 mg) and triethylamine (47 mg) were added. After completion of the addition, the system was purged with carbon monoxide and stirred overnight at 65° C. under carbon monoxide atmosphere. LCMS showed completion of the reaction, and the reaction mixture was concentrated under reduced pressure. The resulting crude product was purified by pre-TLC to give the title compound (67 mg).

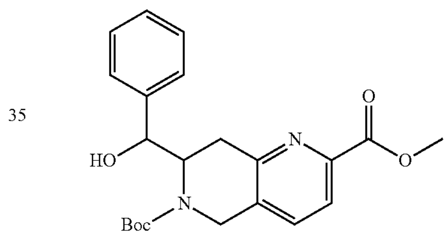

MS (ESI) m/z (M+H =399.1.

Step 3: preparation of methyl 7-(hydroxy(phenyl) methyl)-5,6,7,8-tetrahydro-1,6-naphthyridine-2-carboxylate 6-(Tert-butyl) 2-methyl 7-(hydroxy(phenyl)methyl)-7,8-dihydro-1,6-naphthyridine-2,6(5H) -dicarboxylate (40 mg) was added to hydrogen chloride in 1,4-dioxane (4M, 2 mL) at room temperature and stirred for 30 min. LCMS showed completion of reaction, and the reaction mixture was concentrated under reduced pressure to give the crude title compound.

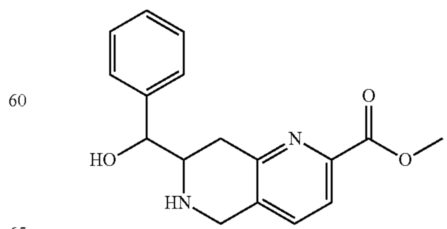

MS (ESI) m/z $(M+H)^+$=299.0.

Step 4: preparation of 7-(hydroxy (phenyl)methyl)-5,6,7,8-tetrahydro-1,6-naphthyridine-2-carboxylic acid hydrochloride The crude methyl 7-(hydroxy(phenyl)methyl)-5,6,7,8-tetrahydro-1,6-naphthyridine-2-carboxylate obtained in step 3 was dissolved in tetrahydrofuran (1 mL)/methanol (1 mL)/water (1 mL) system, lithium hydroxide monohydrate (42 mg) was added and stirred for 30 minutes. LCMS showed completion of the reaction, the reaction mixture was made weakly acidic with hydrogen chloride in 1,4-dioxane (4M), concentrated under reduced pressure, and the residue was purified by pre-HPLC to give the title compound (17.2 mg).

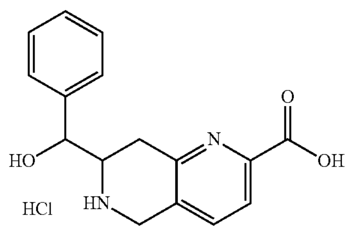 [SMILES: O=C(O)c1ccc2c(n1)CC(C(O)c1ccccc1)NC2 ; Cl]

MS (ESI) m/z $(M+H)^+$=285.1.

$^1H$ NMR (400 MHz, Deuterium Oxide) δ 8.20-8.14 (m, 1H), 8.11 (d, J=8.2 Hz, 1H), 7.57-7.29 (m, 5H), 5.26 (dd, J=3.7, 1.5 Hz, 1H), 4.63 (s, 2H), 4.12-4.00 (m, 1H), 3.30 (dd, J=18.5, 11.9 Hz, 1H), 3.16-3.05 (m, 1H).

Example 13: preparation 7-(1,4-dihydroxybutyl)-5,6,7,8-tetrahydro-1,6-naphthyridine-2-carboxylic acid hydrochloride

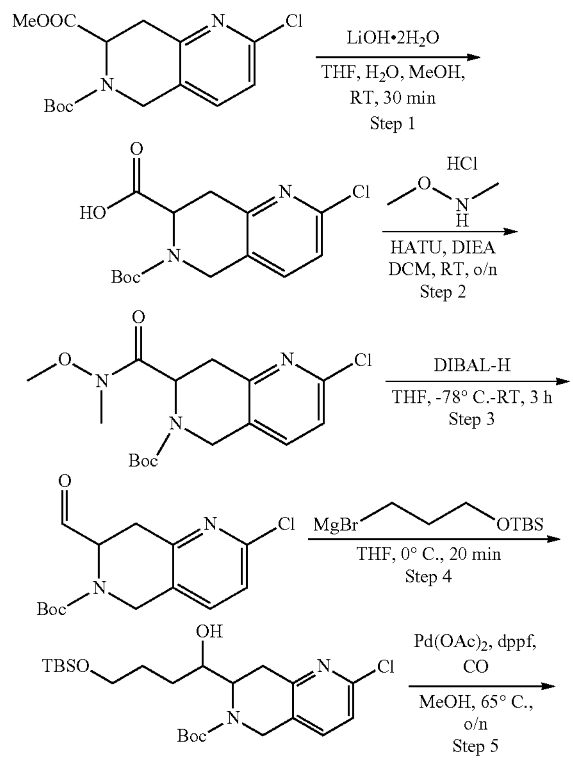

-continued

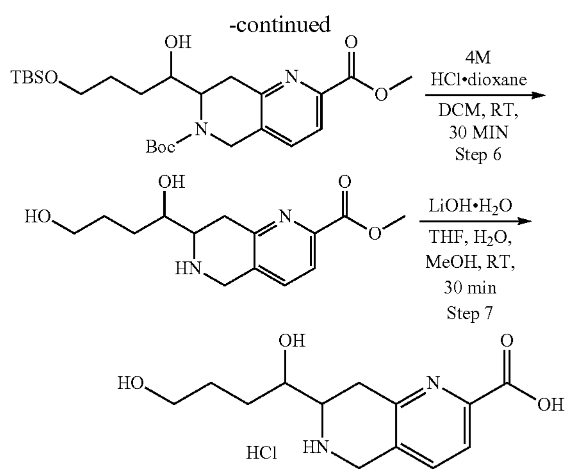

Step 1: preparation of 6-(tert-butoxycarbonyl)-2-chloro-5,6,7,8-tetrahydro-1,6-naphthyridine-7-carboxylic acid 6-(Tert-butyl) 7-methyl 2-chloro-7,8-dihydro-1,6-naphthyridine-6,7(5H)-dicarboxylate (1 g) was dissolved in a system of tetrahydrofuran (3 mL), methanol (3 mL), and water (3 mL) at room temperature, lithium hydroxide hydrate (0.257 g) was added, the reaction was stirred for 30 minutes, and the reaction was completed as indicated by LCMS. The pH was adjusted to 4-5 with dilute hydrochloric acid (1M) under ice-bath cooling, ethyl acetate and water were added and the layers were separated. The aqueous layer was extracted with ethyl acetate, and organic phases were combined, dried over anhydrous sodium sulfate, filtered, and concentrated under reduced pressure to give the title compound (0.95 g).

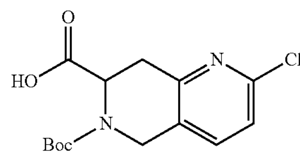 [SMILES: CC(C)(C)OC(=O)N1Cc2ccc(Cl)nc2CC1C(=O)O]

MS (ESI) m/z $(M+H)^+$=313.1.

Step 2: preparation of tert-butyl 2-chloro-7-(methoxy(methyl) carbamoyl)-7,8-dihydro-1,6-naphthyridine-6(5H)-carboxylate 6-(Tert-butoxycarbonyl)-2-chloro-5,6,7,8-tetrahydro-1,6-naphthyridine-7-carboxylic acid (0.95 g) was dissolved in dichloromethane (20 mL) at room temperature, and N,N-diisopropylethylamine (3.0 mL), 2-(7-azabenzotriazol-1-yl)-N,N,N',N'-tetramethyluronium hexafluorophosphate (1.28 g) and methoxymethylamine hydrochloride (0.6 g) were added successively and stirred overnight, and TLC indicated completion of the reaction. Dichloromethane and water were added and the layers were separated. The aqueous layer was extracted with dichloromethane and the extract was washed with saturated sodium chloride solution. The organic phases were combined, dried over anhydrous sodium sulfate, filtered and concentrated under reduced pressure, and the resulting crude product was purified by silica gel column chromatography to give the title compound (900 mg).

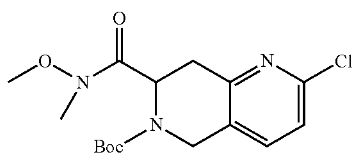 [SMILES: CON(C)C(=O)C1Cc2nc(Cl)ccc2CN1C(=O)OC(C)(C)C]

MS (ESI) m/z $(M+H)^+$=356.1.

Step 3: preparation of tert-butyl 2-chloro-7-formyl-7,8-dihydro-1,6-naphthyridine-6(5H)-carboxylate Tert-butyl 2-Chloro-7-(methoxy(methyl)carbamoyl)-7,8-dihydro-1,6-naphthyridine-6(5H)-carboxylate (0.9 g) was dissolved in anhydrous tetrahydrofuran (20 mL), the system was cooled to −78° C. under nitrogen atmosphere, and diisobutylaluminum hydride solution (7.6 mL) was added. After completion of the addition, the system was slowly warmed to room temperature and stirred for 3 hours. LCMS indicated completion of the reaction. The reaction system was placed in an ice bath, quenched by adding water dropwise over 10 minutes, then saturated potassium sodium tartrate solution (20 mL) was added and stirred for 20 minutes. Extracting with ethyl acetate, the organic phases were combined, dried over anhydrous sodium sulfate, filtered and concentrated under reduced pressure, and the resulting crude product was purified by silica gel column chromatography to give the title compound (0.54 g).

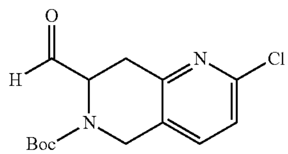 [SMILES: CC(C)(C)OC(=O)N1Cc2ccc(Cl)nc2CC1C=O]

MS (ESI) m/z $(M+H)^+$=297.0.

Step 4: preparation of tert-butyl 7-(4-((tert-butyldimethylsilyl)oxy)-1-hydroxybutyl)-2-chloro-7,8-dihydro-1,6-naphthyridine-6(5H)-carboxylate Tert-butyl 2-chloro-7-formyl-7,8-dihydro-1,6-naphthyridine-6(5H)-carboxylate (128 mg) was dissolved in anhydrous tetrahydrofuran (20 mL), the system was evacuated and backfilled with nitrogen (3 times), cooled to 0° C., and 2M solution of 3-(tert-butyldimethylsiloxy)propylmagnesium bromide (0.42 mL) was added dropwise. After the addition, keeping the temperature and reacting for 20 minutes. LCMS showed completion of the reaction. The reaction system was placed in an ice bath, quenched by adding water dropwise over 10 minutes. Extracting 3 times with ethyl acetate, the organic phases were combined, dried over anhydrous sodium sulfate, filtered and concentrated under reduced pressure, and the resulting crude product was purified by silica gel column chromatography to give the title compound (70 mg).

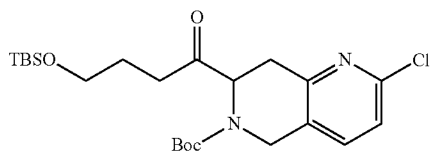 [SMILES: CC(C)(C)OC(=O)N1Cc2ccc(Cl)nc2CC1C(=O)CCCO[Si](C)(C)C(C)(C)C]

MS (ESI) m/z $(M+H)^+$=471.2.

Step 5: preparation of 6-(tert-butyl) 2-methyl 7-(4-(((tert-butyldimethylsilyl)oxy)-1-hydroxybutyl)-7,8-dihydro-1,6-naphthyridine-2,6(5H)-dicarboxylate Tert-butyl 7-(4-((tert-butyldimethyl silyl)oxy)-1-hydroxybutyl)-2-chloro-7,8-dihydro-1,6-naphthyridine-6(5H)-carboxylate (70 mg) was weighed out and dissolved in methanol (10 mL), and triethylamine (30.1 mg), palladium acetate (16.7 mg) and 1,1'-bis(diphenylphosphino)ferrocene (82.5 mg) were added. Carbon monoxide gas was introduced into the reaction system and the reaction was heated to 65° C. to react overnight. LC-MS showed completion of the reaction, and the system was concentrated and the residue was purified by column chromatography to give the title compound (80 mg).

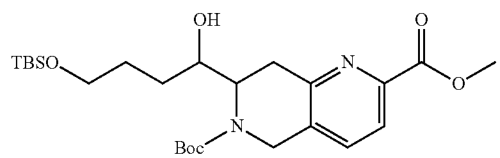 [SMILES: COC(=O)c1ccc2c(n1)CC(C(O)CCCO[Si](C)(C)C(C)(C)C)N(C(=O)OC(C)(C)C)C2]

MS (ESI) m/z $(M+H)^+$=495.2.

Step 6: preparation of methyl 7-(1,4-dihydroxybutyl)-5,6,7,8-tetrahydro-1,6-naphthyridine-2-carboxylate 6-(Tert-butyl) 2-methyl 7-(4-(((tert-butyldimethylsilyl)oxy)-1-hydroxybutyl)-7,8-dihydro-1,6-naphthyridine-2,6(5H)-dicarboxylate (80 mg) was weighed out and dissolved in dichloromethane (3 mL), and 4M hydrogen chloride in 1,4-dioxane (3 mL) was added dropwise under ice-bath cooling, keeping the temperature and reacting for 30 minutes. LC-MS showed completion of the reaction, and the system was concentrated to give crude title compound (50 mg).

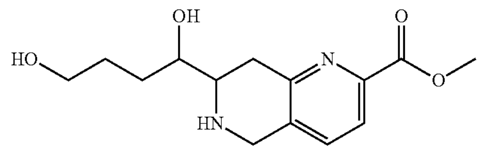 [SMILES: COC(=O)c1ccc2c(n1)CC(C(O)CCCO)NC2]

MS (ESI) m/z $(M+H)^+$=281.1.

Step 7: preparation of 7-(1,4-dihydroxybutyl)-5,6,7,8-tetrahydro-1,6-naphthyridine-2-carboxylic acid hydrochloride Methyl 7-(1,4-dihydroxybutyl)-5,6,7,8-tetrahydro-1,6-naphthyridine-2-carboxylate (70 mg) was weighed out and dissolved in a solution of tetrahydrofuran (1 mL), water (1 mL) and methanol (1 mL), and lithium hydroxide monohydrate (13.44 mg) was added under ice-bath cooling. The reaction was allowed to proceed at room temperature for 30 minutes. LC-MS showed the reaction was complete, and the reaction mixture was adjusted to pH=4-5 with hydrochloric acid solution. The system was concentrated to give crude product, which was purified by pre-HPLC to give the title compound (7 mg).

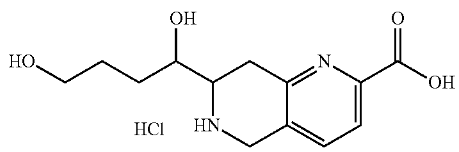 [SMILES: O=C(O)c1ccc2c(n1)CC(C(O)CCCO)NC2 ; Cl]

MS (ESI) m/z $(M+H)^+$=267.0

$^1$H NMR (400 MHz, Deuterium Oxide) δ 7.63-7.51 (m, 2H), 4.02 (d, J=7.8 Hz, 2H), 3.77 (dt, J=7.6, 3.8 Hz, 1H), 3.57 (q, J=4.4, 2.9 Hz, 2H), 3.10 (dt, J=11.2, 4.2 Hz, 1H), 3.01-2.70 (m, 2H), 1.73-1.44 (m, 4H).

Example 14: preparation of 8-((3-isobutylpiperazin-1-yl)-5,6,7,8-tetrahydro-1,6-naphthyridine-2-carboxylic acid hydrochloride

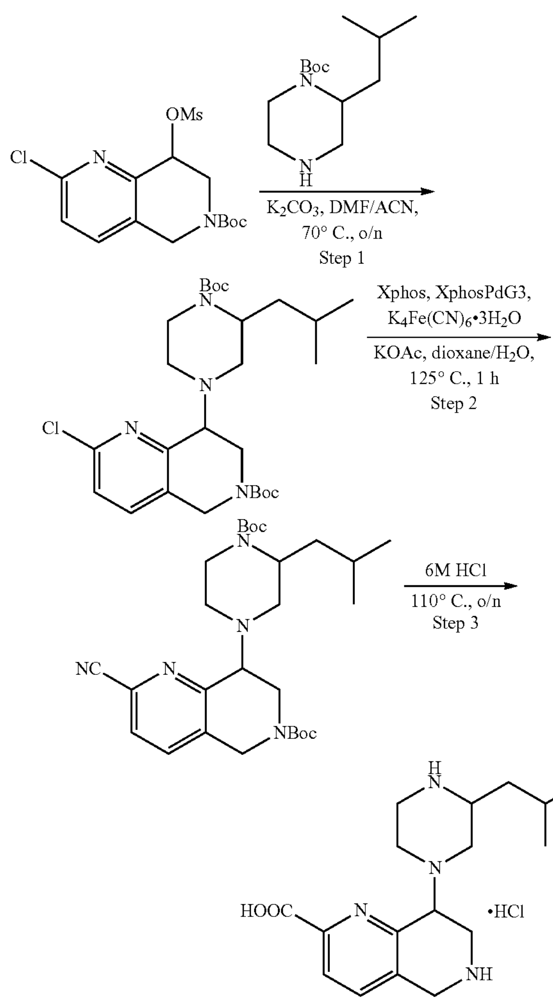

Step 1: preparation of tert-butyl 8-(4-(tert-butoxycarbonyl)-3-isobutylpiperazin-1-yl)-2-chloro-7,8-dihydro-1,6-naphthyridine-6(5H)-carboxylate Tert-butyl 2-chloro-8-((methylsulfonyl)oxy)-7,8-dihydro-1,6-naphthyridine-6(5H)-carboxylate (50 mg) was dissolved in a mixed solvent of N,N-dimethylformamide (0.5 mL) and acetonitrile (0.5 mL), and tert-butyl 2-isobutylpiperazine-1-carboxylate (51 mg) and potassium carbonate (40 mg) were added. The temperature of the reaction was raised to 70° C. to react overnight, and TLC showed disappearance of the starting material. The reaction was cooled to room temperature, quenched with water, extracted with ethyl acetate, and the combined organic phases were washed once with saturated brine, dried over anhydrous sodium sulfate and concentrated, and the residue was purified by column chromatography to give the title compound (30 mg).

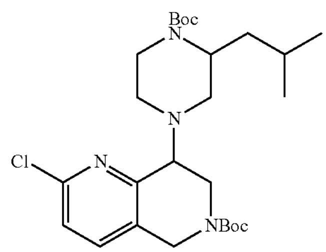 [SMILES: CC(C)CC1CN(C2CN(C(=O)OC(C)(C)C)Cc3ccc(Cl)nc32)CCN1C(=O)OC(C)(C)C]

MS (ESI) m/z $(M+H)^+$=509.0/510.9.

Step 2: preparation of tert-butyl 8-(4-(tert-butoxycarbonyl)-3-isobutylpiperazin-1-yl)-2-cyano-7,8-dihydro-1,6-naphthyridine-6(5H)-carboxylate Tert-butyl 8-(4-(tert-butoxycarbonyl)-3-isobutylpiperazin-1-yl)-2-chloro-7,8-dihydro-1,6-naphthyridine-6(5H)-carboxylate (30 mg) was weighed out and dissolved in a mixed solvent of 1,4-dioxane (1 mL) and water (0.5 mL), and potassium acetate (12 mg), potassium hexacyanoferrate trihydrate (13 mg), 2-(dicyclohexylphosphino)-2,4,6-triisopropylbiphenyl (3 mg), methanesulfonic acid (2-dicyclohexylphosphino-2',4',6'-triisopropyl-1,1'-biphenyl) (2'-amino-1,1'-biphenyl-2-yl)palladium (II) (3 mg) were added successively. The system was evacuated and backfilled with nitrogen (3 times), sealed, and then reacted at 125° C. for 1 hour. LC-MS showed completion of the reaction. The reaction was cooled to room temperature and filtered, the filter cake was washed several times with ethyl acetate. Water was added to the filtrate, the organic layer was separated, and the aqueous phase was extracted three times with ethyl acetate. The organic phases were combined, dried over anhydrous sodium sulfate and concentrated to dryness under reduced pressure, and the residue was purified by column chromatography to give the title compound (20 mg).

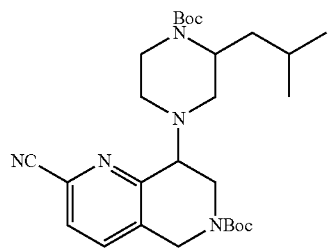 [SMILES: CC(C)CC1CN(C2CN(C(=O)OC(C)(C)C)Cc3ccc(C#N)nc32)CCN1C(=O)OC(C)(C)C]

MS (ESI) m/z $(M+H)^+$=500.0

Step 3: preparation of 8-((3-isobutylpiperazin-1-yl)-5,6,7,8-tetrahydro-1,6-naphthyridine-2-carboxylic acid hydrochloride Tert-butyl 8-(4-(tert-butoxycarbonyl)piperazin-1-yl)-2-cyano-7,8-dihydro-1,6-naphthyridine-6(5H)-carboxylate (20 mg) was weighed out and dissolved in 6M aqueous hydrochloric acid (2 mL). The reaction was carried out overnight at 110° C. and monitored by LC-MS for completion of the reaction. Concentrated under reduced pressure and purified by pre-HPLC to give the title compound (1.48 mg).

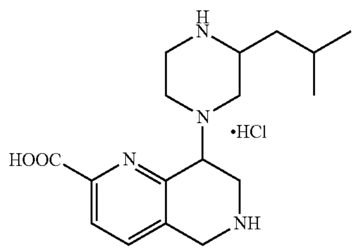 [SMILES: CC(C)CC1CN(C2CNCc3ccc(C(=O)O)nc32)CCN1 ; Cl]

MS (ESI) m/z $(M+H)^+$=319.1.

$^1$H NMR (400 MHz, Deuterium Oxide) δ 7.84-7.78 (dd, J=13.3, 8.0 Hz, 1H), 7.72-7.68 (m, 1H), 4.20-4.14 (dd, J=16.8, 4.3 Hz, 1H), 4.10-4.03 (m, 2H), 3.43-3.32 (m, 2H), 3.25-3.20 (m, 1H), 3.18-2.67 (m, 5H), 2.65-2.45 (dt, J=56.1, 11.6 Hz, 1H), 1.50-1.42 (dq, J=13.2, 6.7 Hz, 1H), 1.32-1.28 (q, J=8.4, 7.6 Hz, 2H), 0.74 (t, J=5.2 Hz, 6H)

Example 15: preparation of 8-(2-benzylmorpholino)-5,6,7,8-tetrahydro-1,6-naphthyridine-2-carboxylic acid hydrochloride

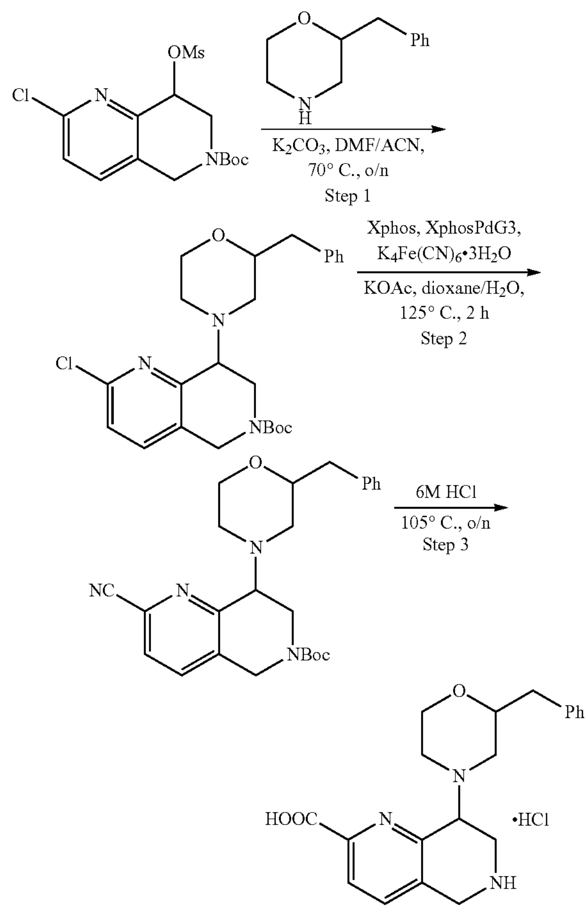

Step 1: preparation of tert-butyl 8-(2-benzylmorpholino)-2-chloro-7,8-dihydro-1,6-naphthyridine-6(5H)-carboxylate Tert-butyl 2-chloro-8-((methylsulfonyl)oxy)-7,8-dihydro-1,6-naphthyridine-6(5H)-carboxylate (50 mg) was dissolved in a mixed solvent of N,N-dimethylformamide (0.5 mL) and acetonitrile (0.5 mL), and 2-benzylmorpholine (38 mg) and potassium carbonate (40 mg) were added. The temperature of the reaction was raised to 70° C. to react overnight, and TLC showed disappearance of the starting material. The reaction was cooled to room temperature, quenched with water, extracted with ethyl acetate, and the combined organic phases were washed once with saturated brine, dried over anhydrous sodium sulfate and concentrated, and the residue was purified by column chromatography to give the title compound (25 mg).

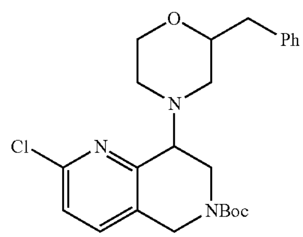 [SMILES: CC(C)(C)OC(=O)N1Cc2ccc(Cl)nc2C(N2CCOC(Cc3ccccc3)C2)C1]

MS (ESI) m/z $(M+H)^+$=444.0/446.0.

Step 2: preparation of tert-butyl 8-(2-benzylmorpholino)-2-cyano-7,8-dihydro-1,6-naphthyridine-6(5H)-carboxylate Tert-butyl 8-(2-benzylmorpholino)-2-chloro-7,8-dihydro-1,6-naphthyridine-6(5H)-carboxylate (25 mg) was weighed out and dissolved in in a mixed solvent of 1,4-dioxane (1 mL) and water (0.5 mL), and potassium acetate (12 mg), potassium hexacyanoferrate trihydrate (13 mg), 2-(dicyclohexylphosphino)-2,4,6-triisopropylbiphenyl (3 mg), methanesulfonic acid (2-dicyclohexylphosphino-2',4',6'-triisopropyl-1,1'-biphenyl) (2'-amino-1,1'-biphenyl-2-yl) palladium (II) (3 mg) were added successively. The system was evacuated and backfilled with nitrogen (3 times), sealed, and then reacted at 125° C. for 2 hour. LC-MS showed completion of the reaction. The reaction was cooled to room temperature and filtered, the filter cake was washed several times with ethyl acetate. Water was added to the filtrate, the organic layer was separated, and the aqueous phase was extracted three times with ethyl acetate. The organic phases were combined, dried over anhydrous sodium sulfate and concentrated to dryness under reduced pressure, and the residue was purified by column chromatography to give the title compound (20 mg).

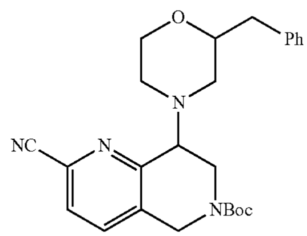 [SMILES: CC(C)(C)OC(=O)N1Cc2ccc(C#N)nc2C(N2CCOC(Cc3ccccc3)C2)C1]

MS (ESI) m/z $(M+H)^+$=435.0.

Step 3: preparation of 8-(2-benzylmorpholino)-5,6,7,8-tetrahydro-1,6-naphthyridine-2-carboxylic acid hydrochloride Tert-butyl 8-(2-benzylmorpholino)-2-cyano-7,8-dihydro-1,6-naphthyridine-6(5H)-carboxylate (20 mg) was weighed out and dissolved in 6M aqueous hydrochloric acid (2 mL). The reaction was carried out overnight at 105° C. and monitored by LC-MS for completion of the reaction. Concentrated under reduced pressure and purified by pre-HPLC to give the title compound (10.34 mg).

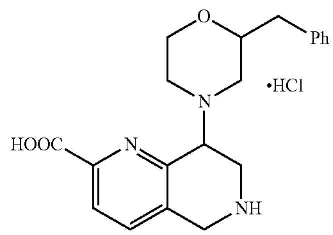 [SMILES: O=C(O)c1ccc2c(n1)C(N1CCOC(Cc3ccccc3)C1)CNC2 ; Cl]

MS (ESI) m/z $(M+H)^+$=354.0.

$^1$H NMR (400 MHz, Methanol-d4) δ 7.99-7.97 (d, J=8.0 Hz, 1H), 7.77-7.74 (d, J=8.1 Hz, 1H), 7.29-7.16 (m, 5H), 4.43-4.27 (m, 3H), 4.21-4.16 (m, 1H), 3.95-3.92 (m, 1H), 3.82-3.72 (m, 2H), 3.50-3.46 (dd, J=13.3, 3.6 Hz, 1H), 2.90 (d, J=10.9 Hz, 1H), 2.84-2.51 (m, 5H).

Example 16 5, preparation of 6,7,8-tetrahydro-1,6-naphthyridine-2, 7-dicarboxylic acid hydrochloride

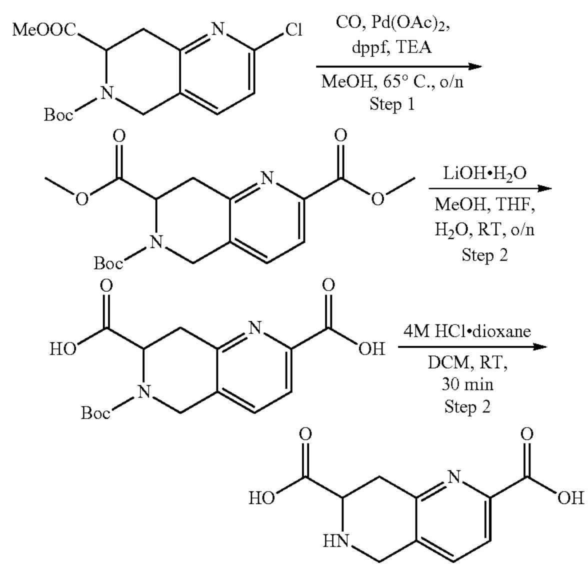

Step 1: preparation of 6-(tert-butyl) 2,7-dimethyl 7,8-dihydro-1,6-naphthyridine-2,6,7(5H)-tricarboxylate 6-(Tert-butyl) 7-methyl 2-chloro-7,8-dihydro-1,6-naphthyridine-6,7(5H)-dicarboxylate (100 mg) was weighed out and dissolved in methanol (10 mL), and triethylamine (0.085 mL), palladium acetate (34.3 mg) and 1,1'-bis(diphenylphosphino)ferrocene (169.5 mg) were added. Carbon monoxide gas was introduced into the system, and the reaction was heated to 65° C. to react overnight. LC-MS showed the reaction was complete, and the system was concentrated and the residue was purified by column chromatography to give the title compound (70 mg).

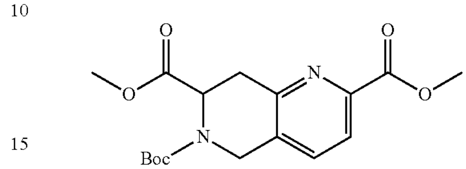

MS (ESI) m/z $(M+H)^+$=351.1.

Step 2: preparation of 6-(tert-butoxycarbonyl)-5,6,7,8-tetrahydro-1,6-naphthyridine -2,7-dicarboxylic acid 6-(Tert-butyl) 2,7-dimethyl 7,8-dihydro-1,6-naphthyridine-2,6,7(5H)-tricarboxylate (70 mg) was weighed out and dissolved in a solution of tetrahydrofuran (3 mL), water (3 mL) and methanol (3 mL), and lithium hydroxide monohydrate (16.6 mg) was added under ice-bath cooling. The reaction was allowed to proceed at room temperature overnight. LC-MS showed completion of the reaction. The pH of the reaction was adjusted to weakly acidic with hydrochloric acid solution, and the system was concentrated to give crude title compound (100 mg).

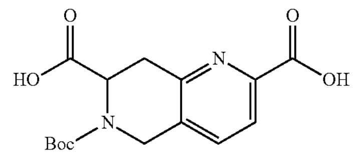

MS (ESI) m/z $(M+H)^+$=323.1.

Step 3: preparation of 5,6,7,8-tetrahydro-1,6-naphthyridine-2,7-dicarboxylic acid hydrochloride 6-(Tert-Butoxycarbonyl)-5,6,7,8-tetrahydro-1,6-naphthyridine-2,7-dicarboxylic acid (63.4 mg) was weighed out and dissolved in dichloromethane (3 mL), and 4M hydrogen chloride in 1,4-dioxane (3 mL) was added dropwise under ice-bath cooling. Keeping the temperature and reacting for 30 minutes. LC-MS showed the reaction was complete. The system was concentrated and the residue was purified by pre-HPLC to give the title compound (35 mg).

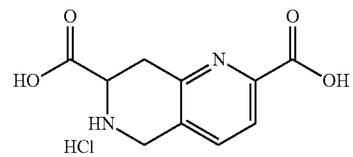 [SMILES: O=C(O)c1ccc2c(n1)CC(C(=O)O)NC2 ; Cl]

MS (ESI) m/z $(MM+H)^+$=223.0.

$^1H$ NMR (400 MHz, Deuterium Oxide) δ 7.75 (s, 2H), 4.45 (q, J=16.1 Hz, 2H), 4.10 (dd, J=11.7, 5.1 Hz, 1H), 3.55-3.38 (m, 1H), 3.19 (dd, J=18.0, 11.7 Hz, 1H).

Example 17: preparation of 3-fluoro-5,6,7,8-tetrahydro-1,6-naphthyridine-2-carboxylic acid hydrochloride

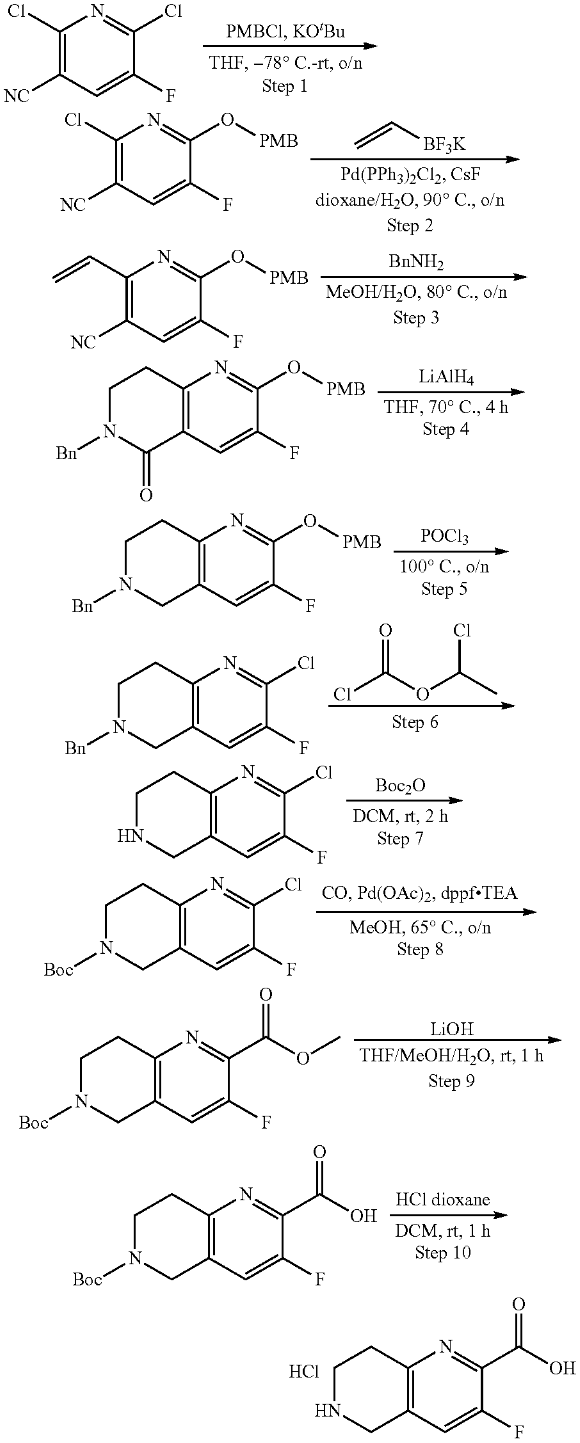

Step 1: preparation of 2-chloro-5-fluoro-6-((4-methoxybenzyl)oxy)nicotinonitrile

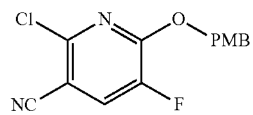

2,6-Dichloro-5-fluoronicotinonitrile (5.0 g) was weighed out and dissolved in tetrahydrofuran (50 mL). The solution was cooled to −78° C. and stirred. Potassium tert-butoxide (3.5 g) was added under nitrogen atmosphere. The system was cooled to −78° C. and a solution of 4-methoxybenzyl chloride (3.95 g) in tetrahydrofuran (50 mL) was added dropwise. After the addition was complete, the reaction solution was warmed up to room temperature and reacted overnight. TLC showed the reaction was complete. The reaction solution was concentrated under reduced pressure, ethyl acetate and water were added thereto, the aqueous layer was separated and extracted, and the organic phase was concentrated to dryness. The resulting crude product was purified by column chromatography to give the title compound (6.2 g).

MS (ESI) m/z $(M+H)^+$=293.1.

Step 2: preparation of 5-fluoro-6-((4-methoxybenzyl)oxy)-2-vinyl-nicotinonitrile

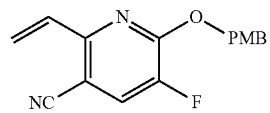

2-Chloro-5-fluoro-6-((4-methoxybenzyl)oxy)nicotinonitrile (6.0 g), potassium vinyltrifluoroborate (5.5 g), [1,1'-bis(diphenylphosphino)ferrocene]dichloropalladium (0.29 g) and cesium fluoride (6.23 g) were weighed into a reaction flask, 1,4-dioxane (60 mL) and water (6 mL) were added. The system was evacuated and backfilled with nitrogen, and the reaction was allowed to proceed overnight at 90° C. TLC indicated substantial completion of the reaction. The mixture was concentrated under reduced pressure to dryness, added with ethyl acetate and water, the aqueous layer was separated and extracted, and the organic phase was concentrated to dryness. The resulting crude product was purified by column chromatography to give the title compound (2.68 g).

MS (ESI) m/z $(M+H)^+$=285.1.

Step 3: preparation of 6-benzyl-3-fluoro-2-((4-methoxybenzyl)oxy)-7,8-dihydro-1,6-naphthyridine-5(6H)-one

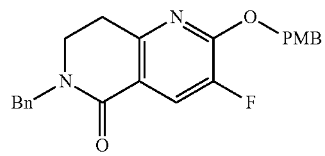

5-Fluoro-6-((4-methoxybenzyl)oxy)-2-vinyl-nicotinonitrile (2.68 g) was weighed out and dissolved in methanol (20 mL) and water (4 mL), and benzylamine (12.44 g) was added. The reaction was allowed to proceed overnight at 80° C. and TLC showed substantial completion of the reaction. The mixture was concentrated under reduced pressure, added with dichloromethane and water, the aqueous layer was separated and extracted, the organic phase was washed with 1M dilute hydrochloric acid and then concentrated to dryness. The resulting crude product was purified by column chromatography to give the title compound (2.37 g).

MS (ESI) m/z $(M+H)^+$=393.1.

Step 4: preparation of 6-benzyl-3-fluoro-24(4-methoxybenzyl)oxy)-5,6,7,8-tetrahydro-1,6-naphthyridine

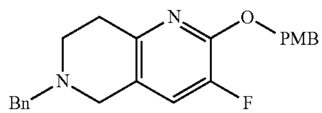

6-Benzyl-3-fluoro-24(4-methoxybenzyl)oxy)-7,8-dihydro-1,6-naphthyridine-5(6H)-one (1.19 g) was weighed out and dissolved in tetrahydrofuran (20 mL), lithium aluminium hydride (0.29 g) was added in portions under ice-bath cooling, and the reaction was carried out at 70° C. for 4 hours. TLC showed substantial completion of the reaction. Under ice-bath cooling, 0.5 mL of water, 0.5 mL of a 15% aqueous sodium hydroxide solution and 1.5 mL of water were added dropwise successively, and the mixture was stirred at room temperature for 15 minutes, and then anhydrous magnesium sulfate was added thereto and stirred for 15 minutes. The mixture was filtered through celite and anhydrous sodium sulfate, the filter residue was washed with ethyl acetate, and the filtrate was concentrated to dryness to give the title compound (1.15 g).

MS (ESI) m/z $(M+H)^+$=379.1.

Step 5: preparation of 6-benzyl-2-chloro-3-fluoro-5,6,7,8-tetrahydro-1,6-naphthyridine

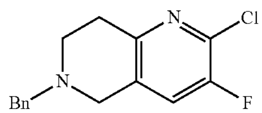 [SMILES: Fc1cc2c(nc1Cl)CCN(Cc1ccccc1)C2]

6-Benzyl-3-fluoro-24(4-methoxybenzyl)oxy)-5,6,7,8-tetrahydro-1,6-naphthyridine (1.14 g) was weighed out and phosphorus oxychloride (10 mL) was added thereto under ice-bath cooling. The reaction was allowed to proceed overnight at 100° C., and TLC showed substantial completion of the reaction. The mixture was concentrated under reduced pressure, diluted with ethyl acetate, added dropwise to crushed ice, and the pH was adjusted to 10 by adding saturated sodium carbonate solution. The mixture was extracted with ethyl acetate and the extract was washed with saturated aqueous sodium chloride solution. The organic phase was dried over anhydrous sodium sulfate, filtrated, and the filtrate was concentrated to dryness to give the crude title compound (0.82 g).

MS (ESI) m/z $(M+H)^+$=277.1.

Step 6: preparation of 2-chloro-3-fluoro-5,6,7,8-tetrahydro-1,6-naphthyridine

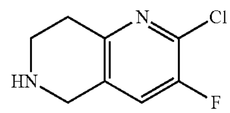

6-Benzyl-2-chloro-3-fluoro-5,6,7,8-tetrahydro-1,6-naphthyridine (0.82 g) was weighed out and dissolved in 1,2-dichloroethane (8 mL), N,N-diisopropylethylamine (1.93 g) and 1-chloroethyl chloroformate (2.57 g) were added successively under ice-bath cooling. The reaction was carried out at 80° C. for 1.5 hours, and TLC showed that the reaction was substantially complete. The system was concentrated to dryness, dissolved with methanol, and reacted at 60° C. for 1.5 hours. TLC showed that the reaction was substantially complete. The system was concentrated to dryness under reduced pressure to obtain the crude title compound.

MS (ESI) m/z $(M+H)^+$=187.1.

Step 7: preparation of 6-(tert-butoxycarbonyl)-2-chloro-3-fluoro-5,6,7,8-tetrahydro-1,6-naphthyridine

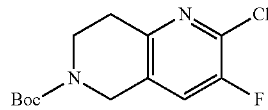 [SMILES: CC(C)(C)OC(=O)N1CCc2nc(Cl)c(F)cc2C1]

2-Chloro-3-fluoro-5,6,7,8-tetrahydro-1,6-naphthyridine was weighed out and dissolved in dichloroethane (10 mL), triethylamine (0.91 g) and di-tert-butyl dicarbonate (0.98 g) were added under ice-bath cooling, and the reaction was carried out at room temperature for 2 hours. TLC showed that the reaction was substantially complete. Dichloromethane and water were added, the aqueous layer was separated and extracted, and the organic phase was concentrated to dryness. The resulting crude product was purified by column chromatography to give the title compound (0.28 g).

MS (ESI) m/z $(M+H)^+$=287.1.

Step 8: preparation of 6-(tert-butyl) 2-methyl 3-fluoro-5,6,7,8-tetrahydro-1,6-naphthyridine-2,6-dicarboxylate

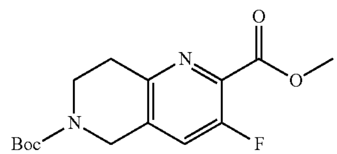 [SMILES: COC(=O)c1nc2c(cc1F)CN(C(=O)OC(C)(C)C)CC2]

6-(Tert-Butoxycarbonyl)-2-chloro-3-fluoro-5,6,7,8-tetrahydro-1,6-naphthyridine (100 mg) was weighed out and dissolved in methanol (10 mL), and palladium acetate (40 mg), 1,1'-bis(diphenylphosphino)ferrocene (200 mg) and triethylamine (71 mg) were added successively. The system was evacuated and backfilled with carbon monoxide (3 times) and reacted overnight at 65° C. under carbon monoxide atmosphere. TLC showed substantial completion of the reaction. The mixture was concentrated to dryness under reduced pressure, and the resulting crude product was purified by column chromatography to give the title compound (100 mg).

MS (ESI) m/z $(M+H)^+$=311.1.

Step 9: preparation of 6-(tert-butoxycarbonyl)-3-fluoro-5,6,7,8-tetrahydro-1,6-naphthyridine-2-carboxylic acid

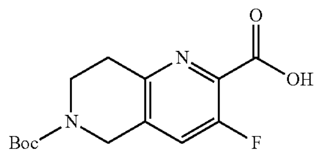 [SMILES: CC(C)(C)OC(=O)N1CCc2nc(C(=O)O)c(F)cc2C1]

6-(Tert-butyl) 2-methyl 3-fluoro-5,6,7,8-tetrahydro-1,6-naphthyridine-2,6-dicarboxylate (100 mg) was weighed out and dissolved in a system of methanol (2 mL), tetrahydrofuran (2 mL) and water (2 mL), and lithium hydroxide monohydrate (27 mg) was added. The reaction was allowed to proceed at room temperature for 1 hour, and TLC showed substantial completion of the reaction. The system was concentrated to dryness to give a crude product, which was used directly in the next reaction.

MS (ESI) m/z $(M+H)^+$=297.1.

Step 10: preparation of 3-fluoro-5,6,7,8-tetrahydro-1,6-naphthyridine-2-carboxylic acid hydrochloride

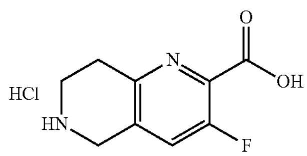 [SMILES: Cl ; O=C(O)c1nc2c(cc1F)CNCC2]

To 6-(Tert-butoxycarbonyl)-3-fluoro-5,6,7,8-tetrahydro-1,6-naphthyridine-2-carboxylic acid (94 mg) was added dichloromethane (3 mL) and a solution of hydrogen chloride in 1,4-dioxane (2 mL, 4.0M), the reaction was allowed to proceed at room temperature for 1 hour, and TLC showed substantial completion of the reaction. The system was concentrated to dryness and the residue was purified by reverse phase preparative column chromatography to give the title compound (62.6 mg).

MS (ESI) m/z $(M+H)^+$=197.1.

$^1$H NMR (400 MHz, Deuterium Oxide) δ 7.64 (d, J=10.2 Hz, 1H), 4.47 (s, 2H), 3.61 (t, J=6.4 Hz, 2H), 3.18 (t, J=6.5 Hz, 2H).

Example 45: preparation of 7,7-diethyl-5,6,7,8-tetrahydro-1,6-naphthyridine-2-carboxylic acid hydrochloride

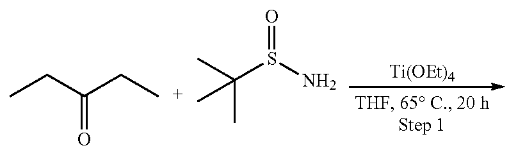

-continued

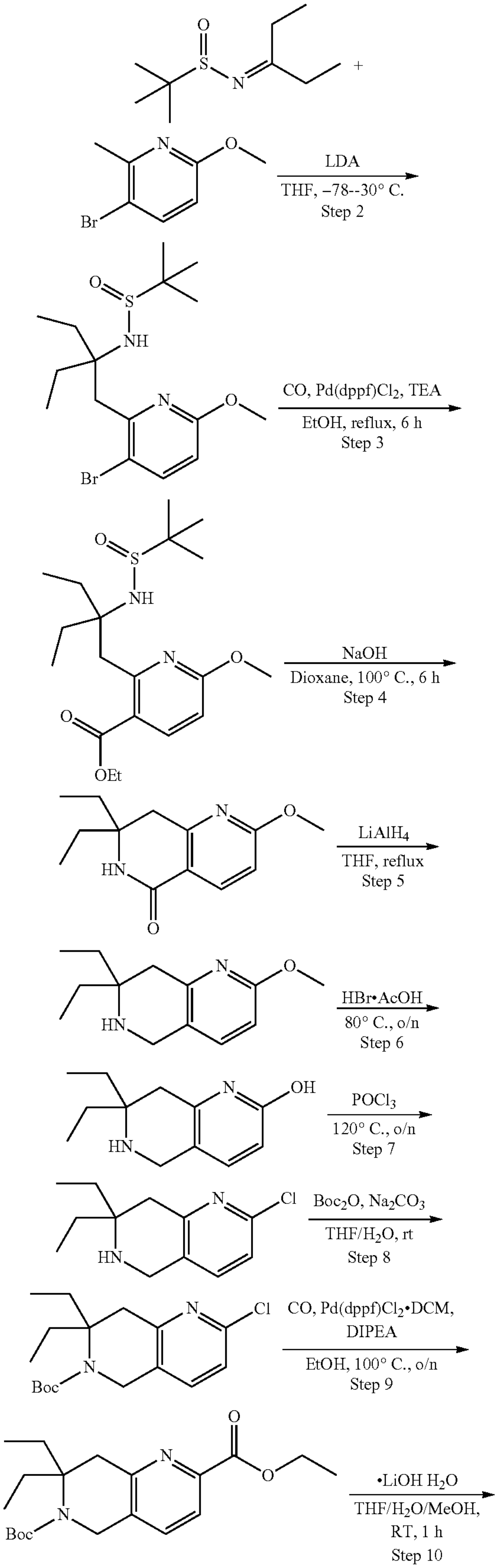

-continued

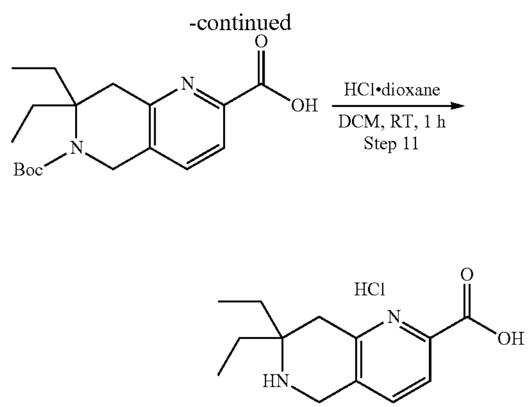

Step 1: preparation of 2-methyl-N-(pentan-3-ylidene)propane-2-sulfinamide

Pentan-3-one (10.73 g) was weighed out and dissolved in tetrahydrofuran (300 mL), and tetraethyl titanate (46 g) and 2-methylpropane-2-sulfinamide (12 g) were added thereto. After completion of addition, the system was evacuated and backfilled with nitrogen (3 times). The reaction was heated to 65° C. and allowed to react for 20 hours. LC-MS showed that the reaction was complete. Water (30 mL) was added to the system to precipitate a large amount of solid, the mixture was filtered with suction, the organic phase was dried and concentrated to dryness, and the residue was purified by column chromatography to give the title compound (10.8 g).

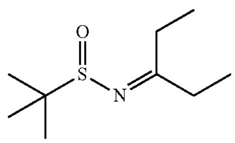

MS (ESI) m/z $(M+H)^+$=190.1.

Step 2: preparation of N-(34(3-bromo-6-methoxy-pyridin-2-yl)methyl)pent-3-yl)-2-methylpropane-2-sulfinamide To a dry reaction flask was added tetrahydrofuran (50 mL), the system was evacuated and backfilled with nitrogen (3 times), and 2M lithium diisopropylamide (25 mL) was added and the temperature was reduced to −78° C. A solution of 3-bromo-6-methoxy-2-methylpyridine (9.4 g) in tetrahydrofuran (50 mL) was added and the mixture was stirred at −78° C. for 1 hour. A solution of 2-methyl-N-(pentan-3-ylidene)propane-2-sulfinamide (8 g) in tetrahydrofuran (50 mL) was added and the temperature was slowly raised from −78° C. to −30° C. The mixture was stirred for 2 hours, and LC-MS showed the reaction was complete. The reaction was quenched with saturated ammonium chloride solution and extracted 3 times with ethyl acetate. The organic phase was dried and concentrated to dryness, and the residue was purified by column chromatography to give the title compound (11.3 g).

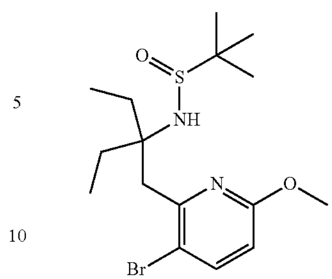

MS (ESI) m/z $(M+H)^+$=391.1.

Step 3: preparation of ethyl 2-(2-((tert-butylsulfinyl)amino)-2-ethylbutyl)-6-methoxynicotinate N-(3 ((3-bromo-6-methoxypyridin-2-yl)methyl)pent-3-yl)-2-methylpropane-2-sulfinamide (11.3 g) was added into a dry reaction flask and dissolved in ethanol (10 mL), and 1,1'-Bis(diphenylphosphino)ferrocene-palladium(II)dichloride dichloromethane complex (4.73 g) and triethylamine (9.6 mL) were added. The system was evacuated and backfilled with carbon monoxide (3 times), and then heated to reflux for 6 hours. LC-MS showed that the reaction was complete. The system was concentrated to dryness. Purification by column chromatography gave the title compound (9.3 g).

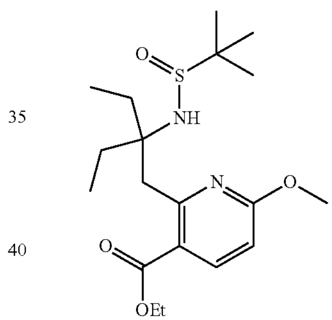

MS (ESI) m/z $(M+H)^+$=385.2.

Step 4: preparation of 7,7-diethyl-2-methoxy-7,8-dihydro-1,6-naphthyridine-5(6H)-one Ethyl 2-(2-((tert-butylsulfinyl)amino)-2-ethylbutyl)-6-methoxynicotinate (9.3 g) was added into a dry reaction flask and dissolved in dioxane (10 mL), sodium hydroxide (4.8 g) was added and the reaction was heated to 100° C. for 6 hours. LC-MS showed that the reaction was complete. The system was filtered through celite, and the filtrate was concentrated to dryness. Purification by column chromatography gave the title compound (4.6 g).

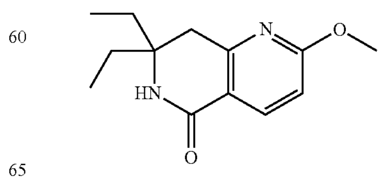

MS (ESI) m/z $(M+H)^+$=235.1.

Step 5: preparation of 7,7-diethyl-2-methoxy-5,6,7,8-tetrahydro-1,6-naphthyridine 7,7-Diethyl-2-methoxy-7,8-dihydro-1,6-naphthyridine-5(6H)-one (3 g) was weighed out and dissolved in tetrahydrofuran (100 mL), and lithium aluminium hydride (1.9 g) was added in portions under ice-bath cooling. The reaction was heated to reflux and stirred overnight. LC-MS showed that the reaction was complete. The mixture was concentrated to dryness. Purification by silica gel column chromatography gave the title compound (2.8 g).

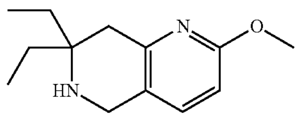 [SMILES: CCC1(CC)Cc2nc(OC)ccc2CN1]

MS (ESI) m/z $(M+H)^+$=221.1.

Step 6: preparation of 7,7-diethyl-5,6,7,8-tetrahydro-1,6-naphthyridine-2-ol 7,7-Diethyl-2-methoxy-5,6,7,8-tetrahydro-1,6-naphthyridine (2.8 g) was weighed out and dissolved in 33% hydrogen bromide in acetic acid (w/w, 20 mL). The reaction was heated to 80° C. and stirred overnight. LC-MS showed that the reaction was complete. The mixture was concentrated to dryness. The resulting crude product was slurried with acetonitrile to give the title compound (4.3 g).

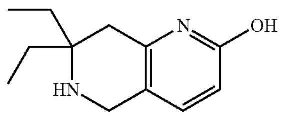

MS (ESI) m/z $(M+H)^+$=207.1.

Step 7: preparation of 2-chloro-7,7-diethyl-5,6,7,8-tetrahydro-1,6-naphthyridine 7,7-Diethyl-5,6,7,8-tetrahydro-1,6-naphthyridine-2-ol (2.8 g) was weighed out and dissolved in phosphorus oxychloride (40 mL). The reaction was heated to 120° C. and reacted overnight. LC-MS showed that the reaction was complete, and the mixture was concentrated to dryness under reduced pressure. Diluting with dichloromethane, water was added and the pH was adjusted to 9-10 with sodium carbonate. The obtained crude title compound was directly used in the next reaction without purification.

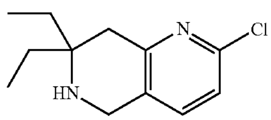

MS (ESI) m/z $(M+H)^+$=225.1.

Step 8: preparation of tert-butyl 2-chloro-7,7-diethyl-7,8-dihydro-1,6-naphthyridine-6(5H)-carboxylate The crude product obtained in the previous step was dissolved in $THF/H_2O$, the system was treated with sodium carbonate, di-tert-butyl dicarbonate (4.67 mL) was added and the mixture was stirred overnight at room temperature. LC-MS showed that the reaction was complete. The mixture was extracted with dichloromethane for 3 times, and the organic phase was dried and concentrated. Purification by silica gel column chromatography gave the title compound (1.5 g).

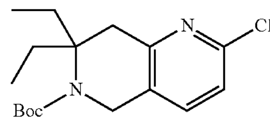 [SMILES: CCC1(CC)Cc2nc(Cl)ccc2CN1C(=O)OC(C)(C)C]

MS (ESI) m/z $(M+H)^+$=325.1.

Step 9: preparation of 6-(tert-butyl) 2-ethyl 7,7-diethyl-7,8-dihydro-1,6-naphthyridine-2,6(5H)-dicarboxylate Tert-butyl 2-chloro-7,7-diethyl-7,8-dihydro-1,6-naphthyridine-6(5H)-carboxylate (100 mg) was added in a dry reaction flask and dissolved in ethanol (10 mL), and [1,1'-bis(diphenylphosphino)ferrocene]palladium dichloride dichloromethane complex (50.3 mg) and N,N-diisopropylethylamine (0.11 mL) were added. The system was introduced with carbon monoxide gas and heated to 100° C. The reaction was allowed to proceed overnight. LC-MS showed that the reaction was complete, and the system was concentrated to dryness. Purification by column chromatography gave the title compound (80 mg).

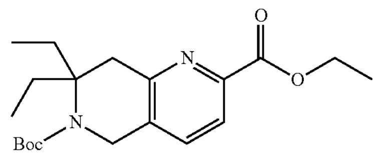 [SMILES: CCOC(=O)c1ccc2c(n1)CC(CC)(CC)N(C(=O)OC(C)(C)C)C2]

MS (ESI) m/z $(M+H)^+$=363.2.

Step 10: preparation of 6-(tert-butoxycarbonyl)-7,7-diethyl-5,6,7,8-tetrahydro-1,6-naphthyridine-2-carboxylic acid 6-(Tert-butyl) 2-ethyl 7,7-diethyl-7,8-dihydro-1,6-naphthyridine-2,6(5H)-dicarboxylate (45 mg) was weighed out and dissolved in a solution of tetrahydrofuran (1 mL), water (1 mL) and methanol (1 mL), and lithium hydroxide hydrate (10.6 mg) was added at room temperature. The reaction was allowed to proceed at room temperature for 1 hour. LC-MS showed that the reaction was complete, and the system was concentrated to give the crude product as a white solid.

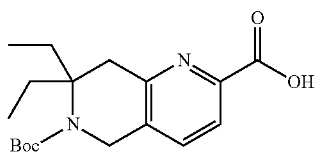 [SMILES: CCC1(CC)Cc2nc(C(=O)O)ccc2CN1C(=O)OC(C)(C)C]

MS (ESI) m/z $(M+H)^+$=335.1.

Step 11: preparation of 7,7-diethyl-5,6,7,8-tetrahydro-1,6-naphthyridine-2-carboxylic acid hydrochloride The crude solid from the previous step was dissolved in dichloromethane (1.5 mL), and 4M hydrogen chloride in 1,4-dioxane (1.5 mL) was added dropwise under ice-bath cooling. After completion of addition, the reaction was allowed to proceed at room temperature for 1 hour. LC-MS showed the reaction was complete and the system was concentrated to give the crude product, which was purified by pre-HPLC to give the title compound (5 mg).

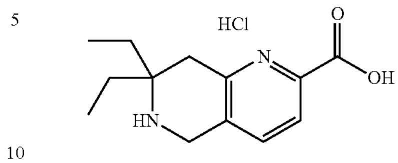

MS (ESI) m/z $(M+H)^+$=235.1

$^1$H NMR (400 MHz, Deuterium Oxide) δ 8.32 (dd, J=7.9, 2.8 Hz, 1H), 8.06 (t, J=7.7 Hz, 1H), 4.59 (s, 2H), 3.37 (s, 2H), 1.78 (q, J=7.5 Hz, 4H), 0.95 (t, J=7.5 Hz, 6H).

The following compounds were prepared using conventional commercially available starting materials and reagents, referring to the preparation methods of the foregoing examples in combination with conventional separation and purification methods in the field:

| Exp. | Structure | MS (ESI) m/z $(M + H)^+$ and $^1$H NMR data | Preparation method |
| --- | --- | --- | --- |
| 18 | 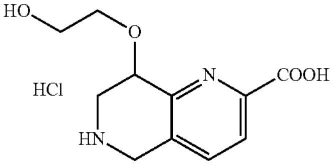 [SMILES: O=C(O)c1ccc2c(n1)C(OCCO)CNC2 ; Cl] | MS (ESI) m/z $(M + H)^+$ = 239.0. $^1$H NMR (400 MHz, Deuterium Oxide) δ 7.97-7.71 (m, 2H), 4.75 (s, 1H), 4.45 (q, J = 16.5 Hz, 2H), 3.95 (d, J = 14.1 Hz, 1H), 3.88-3.72 (m, 2H), 3.66 (t, J = 4.5 Hz, 2H), 3.51 (dd, J = 13.7, 2.1 Hz, 1H). | Refererring to Example 2 |
| 19 | 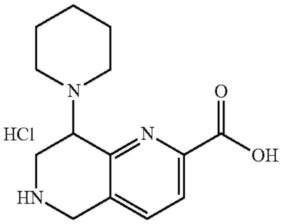 [SMILES: Cl ; O=C(O)c1ccc2c(n1)C(N1CCCCC1)CNC2] | MS (ESI) m/z $(M + H)^+$ = 262.0. $^1$H NMR (400 MHz, Deuterium Oxide) δ 7.85 (d, J = 8.0 Hz, 1H), 7.69 (d, J = 8.1 Hz, 1H), 4.55 (t, J = 7.3 Hz, 1H), 4.10-3.89 (m, 2H), 3.61 (dd, J = 13.4, 6.2 Hz, 1H), 3.40 (dd, J = 13.4, 8.6 Hz, 1H), 3.32-2.97 (m, 4H), 1.83 (t, J = 6.3 Hz, 1H), 1.58 (s, 2H). | Referring to Example 5 |
| 20 | 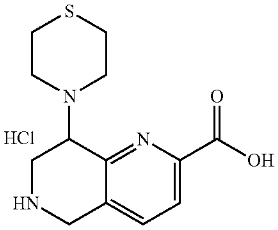 [SMILES: Cl ; O=C(O)c1ccc2c(n1)C(N1CCSCC1)CNC2] | MS (ESI) m/z $(M + H )^+$ = 280.0. $^1$H NMR (400 MHz, Deuterium Oxide) δ 7.85 (d, J = 8.0 Hz, 1H), 7.72 (d, J = 8.0 Hz, 1H), 4.45 (s, 1H), 4.26 (q, J = 16.5 Hz, 2H), 3.78-3.53 (m, 2H), 3.25-2.98 (m, 4H), 2.80 (dt, J = 7.1, 3.3 Hz, 4H). | Referring to Example 5 |
| 21 | 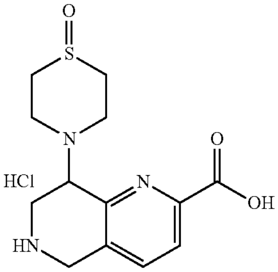 [SMILES: Cl ; O=C(O)c1ccc2c(n1)C(N1CCS(=O)CC1)CNC2] | MS (ESI) m/z $(M + H)^+$ = 295.9. $^1$H NMR (400 MHz, Deuterium Oxide) δ 7.99 (dd, J = 48.2, 8.2 Hz, 2H), 4.60-4.46 (m, 3H), 3.88-3.72 (m, 2H), 3.46-3.21 (m, 2H), 3.13-2.79 (m, 6H). | Referring to Example 5 |

-continued

| Exp. | Structure | MS (ESI) m/z $(M + H)^+$ and $^1H$ NMR data | Preparation method |
|---|---|---|---|
| 22 | 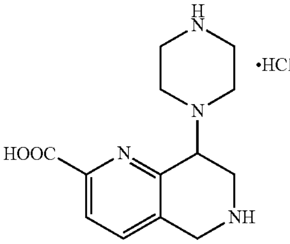 [SMILES: O=C(O)c1ccc2c(n1)C(N1CCNCC1)CNC2 ; Cl] | MS (ESI) m/z $(M + H)^+$: 263.1. $^1H$ NMR (400 MHz, $D_2O$) δ 8.01 (s, 1H), 7.88 (s, 1H), 4.50 (q, J = 16.5 Hz, 2H), 4.14 (s, 1H), 3.76-3.73 (m, 1H), 3.61-3.47 (m, 1H), 3.16 (m, 4H), 2.92-2.90 (s, J = 10.1 Hz, 2H), 2.63 (d, J = 10.1 Hz, 2H). | Referring to Example 5 |
| 23 | 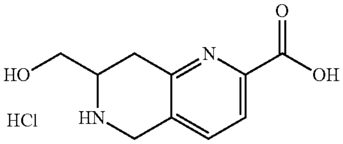 [SMILES: Cl ; O=C(O)c1ccc2c(n1)CC(CO)NC2] | MS (ESI) m/z $(M + H)^+$ = 209.1. $^1H$ NMR (400 MHz, Deuterium Oxide) δ 8.06 (q, J = 8.1 Hz, 2H), 4.65-4.49 (m, 2H), 3.97 (dd, J = 12.5, 3.1 Hz, 1H), 3.78 (td, J = 14.7, 12.3, 7.3 Hz, 2H), 3.30 (dd, J = 37.1, 15.2 Hz, 2H). | Referring to Example 7 |
| 24 | 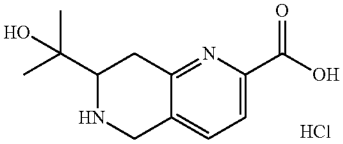 [SMILES: CC(C)(O)C1Cc2nc(C(=O)O)ccc2CN1 ; Cl] | MS (ESI) m/z $(M + H)^+$ = 237.1. $^1H$ NMR (400 MHz, Deuterium Oxide) δ 7.70 (s, 2H), 4.46 (d, J = 2.4 Hz, 2H), 3.57 (d, J = 10.9 Hz, 1H), 3.23 (d, J = 17.7 Hz, 1H), 3.07 (s, 1H), 1.36 (s, 3H), 1.27 (s, 3H). | Referring to Example 9 |
| 25 | 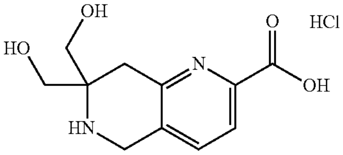 [SMILES: O=C(O)c1ccc2c(n1)CC(CO)(CO)NC2 ; Cl] | MS (ESI) m/z $(M + H)^+$ = 239.1. $^1H$ NMR (400 MHz, Deuterium Oxide) δ 8.26-7.97 (m, 2H), 4.55 (s, 2H), 3.78 (d, J = 12.7 Hz, 2H), 3.67 (d, J = 12.7 Hz, 2H), 3.24 (s, 2H). | Referring to Example 7 |
| 26 | 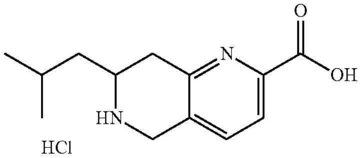 [SMILES: CC(C)CC1Cc2nc(C(=O)O)ccc2CN1 ; Cl] | MS (ESI) m/z $(M + H)^+$ = 235.1. $^1H$ NMR (400 MHz, Deuterium Oxide) δ 7.66 (s, 2H), 4.39 (s, 2H), 3.72 (dt, J = 6.9, 3.7 Hz, 1H), 3.26 (dd, J = 18.1, 4.9 Hz, 1H), 2.90 (dd, J = 18.1, 10.7 Hz, 1H), 1.83-1.70 (m, 1H), 1.60 (t, J = 7.2 Hz, 2H), 0.86 (dd, J = 12.2, 6.5 Hz, 6H). | Referring to Example 12 |
| 27 | 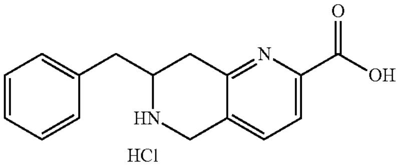 [SMILES: O=C(O)c1ccc2c(n1)CC(Cc1ccccc1)NC2 ; Cl] | MS (ESI) m/z $(M + H)^+$ = 269.0. $^1H$ NMR (400 MHz, Deuterium Oxide) δ 7.65 (s, 2H), 7.39-7.21 (m, 5H), 4.37 (s, 2H), 4.01-3.89 (m, 1H), 3.24-2.96 (m, 4H). | Referring to Example 12 |
| 28 | 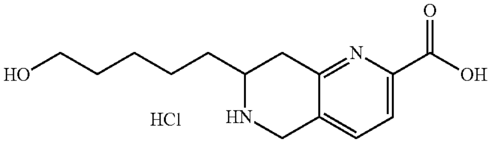 [SMILES: O=C(O)c1ccc2c(n1)CC(CCCCCO)NC2 ; Cl] | MS (ESI) m/z $(M + H)^+$ = 265.1. $^1H$ NMR (400 MHz, Deuterium Oxide) δ 7.64 (s, 2H), 4.39 (s, 2H), 3.64 (d, J = 11.0 Hz, 1H), 3.50 (t, J = 6.5 Hz, 2H), 3.24 (dd, J = 18.1, 4.8 Hz, 1H), 2.93 (dd, J = 18.1, 10.8 Hz, 1H), 1.86-1.64 (m, 2H), 1.47 (ddd, J = 16.3, 11.9, 6.4 Hz, 4H), 1.32 (q, J = 7.7 Hz, 2H). | Referring to Example 10 |
| 29 | 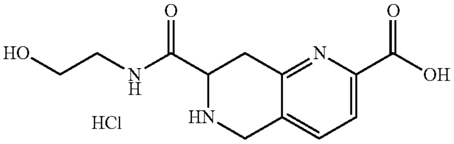 [SMILES: O=C(O)c1ccc2c(n1)CC(C(=O)NCCO)NC2 ; Cl] | MS (ESI) m/z (M + H)+ = 266.0. $^1H$ NMR (400 MHz, Deuterium Oxide) δ 8.06 (d, J = 4.7 Hz, 2H), 4.53 (d, J = 16.8 Hz, 2H), 4.41 (dd, J = 11.8, 4.9 Hz, 1H), 3.58 (t, J = 5.2 Hz, 3H), 3.41-3.23 (m, 3H). | Referring to Example 8 |
| 30 | 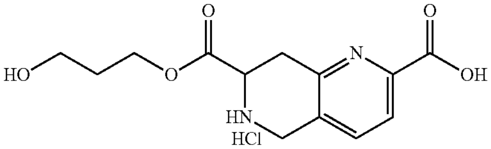 [SMILES: O=C(O)c1ccc2c(n1)CC(C(=O)OCCCO)NC2 ; Cl] | MS (ESI) m/z $(M + H)^+$ = 281.1. $^1H$ NMR (400 MHz, Deuterium Oxide) δ 7.71 (s, 2H), 4.61-4.51 (m, 1H), 4.52-4.21 (m, 4H), 3.65-3.44 (m, 3H), 3.28 (dd, J = 17.9, 11.0 Hz, 1H), 1.85 (p, J = 6.3 Hz, 2H). | Referring to Example 8 |

-continued

| Exp. | Structure | MS (ESI) m/z $(M + H)^+$ and $^1H$ NMR data | Preparation method |
|---|---|---|---|
| 31 | 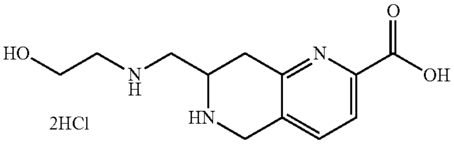 [SMILES: O=C(O)c1ccc2c(n1)CC(CNCCO)NC2 ; "2HCl"] | MS (ESI) m/z $(M + H)^+$ = 252.1. $^1H$ NMR (400 MHz, Deuterium Oxide) δ 8.07 (d, J = 8.1 Hz, 1H), 7.99 (d, J = 8.1 Hz, 1H), 4.67-4.55 (m, 2H), 4.20 (dq, J = 11.4, 5.9 Hz, 1H), 3.83 (t, J = 5.1 Hz, 2H), 3.70-3.46 (m, 3H), 3.35-3.15 (m, 3H). | Referring to Example 11 |
| 32 | 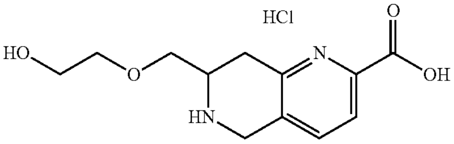 [SMILES: O=C(O)c1ccc2c(n1)CC(COCCO)NC2 ; Cl] | MS (ESI) m/z $(M + H)^+$ = 253.1. $^1H$ NMR (400 MHz, Deuterium Oxide) δ 7.68-7.45 (m, 2H), 4.15 (s, 2H), 3.71 (t, J = 7.3 Hz, 1H), 3.68-3.37 (m, 6H), 3.02-2.91 (m, 1H), 2.79 (dd, J = 17.7, 9.7 Hz, 1H). | Referring to Example 7 |
| 33 | 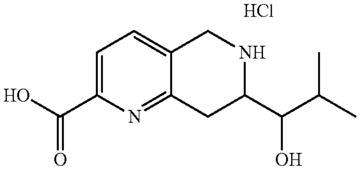 [SMILES: Cl ; CC(C)C(O)C1Cc2nc(C(=O)O)ccc2CN1] | MS (ESI) m/z $(M + H)^+$ = 251.1. $^1H$ NMR (400 MHz, Deuterium Oxide) δ 7.69 (d, J = 2.5 Hz, 2H), 4.42 (s, 2H), 3.69 (td, J = 11.6, 9.9, 5.1 Hz, 1H), 3.56 (dd, J = 8.2, 3.8 Hz, 1H), 3.20 (dd, J = 17.9, 5.0 Hz, 1H), 3.06-2.99 (m, 1H), 1.92 (td, J = 6.9, 4.0 Hz, 1H), 0.92 (d, J = 6.8 Hz, 3H), 0.82 (d, J = 6.7 Hz, 3H). | Referring to Example 12 |
| 34 | 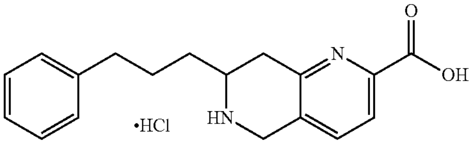 [SMILES: O=C(O)c1ccc2c(n1)CC(CCCc1ccccc1)NC2 ; Cl] | MS (ESI) m/z $(M + H)^+$ = 297.0. $^1H$ NMR (400 MHz, Deuterium Oxide) δ 7.69-7.61 (m, 2H), 7.32-7.14 (m, 5H), 4.37 (s, 2H), 3.70-3.60 (m, 1H), 3.24 (dd, J = 18.1, 4.8 Hz, 1H), 2.92 (dd, J = 18.1, 10.7 Hz, 1H), 2.64 (s, 2H), 1.75 (dt, J = 14.0, 6.3 Hz, 4H). | Referring to Example 45 |
| 35 | 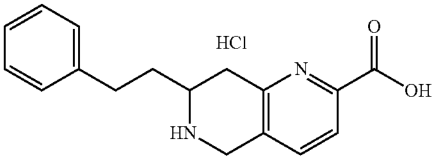 [SMILES: O=C(O)c1ccc2c(n1)CC(CCc1ccccc1)NC2 ; Cl] | MS (ESI) m/z $(M + H)^+$ = 283.1 $^1H$ NMR (400 MHz, Deuterium Oxide) δ 7.79-7.60 (m, 2H), 7.51-7.10 (m, 5H), 4.38 (d, J = 8.3 Hz, 2H), 3.60 (dp, J = 13.5, 5.5, 4.8 Hz, 1H), 3.31 (dd, J = 18.1, 4.8 Hz, 1H), 3.01 (dd, J = 18.1, 10.9 Hz, 1H), 2.93-2.63 (m, 2H), 2.21-1.93 (m, 2H). | Referring to Example 45 |
| 36 | 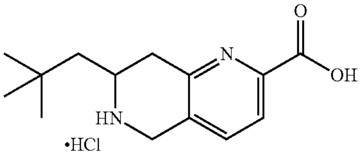 [SMILES: CC(C)(C)CC1Cc2nc(C(=O)O)ccc2CN1 ; Cl] | MS (ESI) m/z $(M + H)^+$ = 249.1. $^1H$ NMR (400 MHz, Deuterium Oxide) δ 7.60 (s, 2H), 4.43-4.30 (m, 2H), 3.71 (ddd, J = 10.2, 5.1, 2.1 Hz, 1H), 3.31 (dd, J = 18.1, 4.9 Hz, 1H), 2.96 (dd, J = 18.1, 10.3 Hz, 1H), 1.67-1.57 (m, 2H), 0.98-0.76 (m, 9H). | Referring to Example 45 |
| 37 | 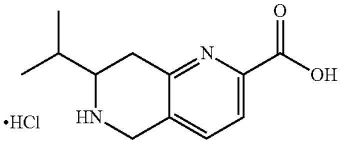 [SMILES: Cl ; CC(C)C1Cc2nc(C(=O)O)ccc2CN1] | MS (ESI) m/z $(M + H)^+$ = 221.1. $^1H$ NMR (400 MHz, Deuterium Oxide) δ 7.66 (s, 2H), 4.48-4.34 (m, 2H), 3.52 (dt, J = 10.8, 5.1 Hz, 1H), 3.16 (dd, J = 18.0, 4.7 Hz, 1H), 3.02 (dd, J = 18.1, 11.8 Hz, 1H), 2.09 (dq, J = 13.4, 6.8 Hz, 1H), 1.01 (dd, J = 8.4, 6.9 Hz, 6H). | Referring to Example 45 |
| 38 | 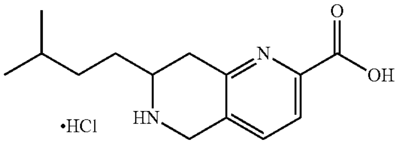 [SMILES: CC(C)CCC1Cc2nc(C(=O)O)ccc2CN1 ; Cl] | MS (ESI) m/z $(M + H)^+$ = 249.2. $^1H$ NMR (400 MHz, Deuterium Oxide ) δ 7.65 (s, 2H), 4.39 (s, 2H), 3.63 (dt, J = 7.7, 5.3 Hz, 1H), 3.25 (dd, J = 18.1, 4.8 Hz, 1H), 2.94 (dd, J = 18.1, 10.8 Hz, 1H), 1.84-1.67 (m, 2H), 1.56-1.47 (m, 1H), 1.35-1.25 (m, 2H), 0.81 (d, J = 6.6 Hz, 6H). | Referring to Example 45 |
| 39 | 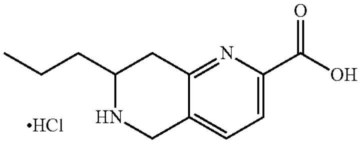 [SMILES: CCCC1Cc2nc(C(=O)O)ccc2CN1 ; Cl] | MS (ESI) m/z $(M + H)^+$ = 221.1. $^1H$ NMR (400 MHz, Deuterium Oxide) δ 7.71 (s, 2H), 4.42 (s, 2H), 3.67 (t, J = 6.4 Hz, 1H), 3.28 (dd, J = 18.2, 4.8 Hz, 1H), 2.96 (dd, J = 18.2, 10.8 Hz, 1H), 1.83-1.66 (m, 2H), 1.50-1.37 (m, 2H), 0.89 (t, J = 7.3 Hz, 3H). | Referring to Example 45 |

-continued

| Exp. | Structure | MS (ESI) m/z (M + H)+ and $^1$H NMR data | Preparation method |
|---|---|---|---|
| 40 | 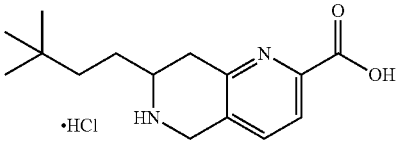 [SMILES: CC(C)(C)CCC1Cc2nc(C(=O)O)ccc2CN1 ; Cl] | MS (ESI) m/z (M + H)$^+$ = 263.2. $^1$H NMR (400 MHz, Deuterium Oxide) δ 7.72 (s, 2H), 4.44 (s, 2H), 3.69-3.60 (m, 1H), 3.30 (dd, J = 18.2, 4.8 Hz, 1H), 3.00 (dd, J = 18.2, 10.7 Hz, 1H), 1.85-1.68 (m, 2H), 1.32 (ddd, J = 11.5, 9.4, 5.4 Hz, 2H), 0.84 (s, 9H). | Referring to Example 45 |
| 41 | 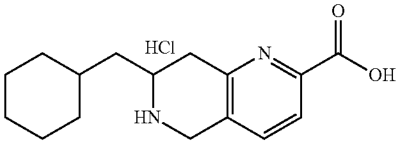 [SMILES: O=C(O)c1ccc2c(n1)CC(CC1CCCCC1)NC2 ; Cl] | MS (ESI) m/z (M + H)$^+$ = 275.1. $^1$H NMR (400 MHz, Deuterium Oxide) δ 7.77 (d, J = 8.1 Hz, 1H), 7.72 (d, J = 8.1 Hz, 1H), 4.44 (s, 2H), 3.80 (ddt, J = 14.9, 10.8, 5.7 Hz, 1H), 3.31 (dd, J = 18.3, 4.8 Hz, 1H), 2.95 (dd, J = 18.3, 10.7 Hz, 1H), 1.77-1.37 (m, 8H), 1.25-1.03 (m, 3H), 0.98-0.82 (m, 2H). | Referring to Example 45 |
| 42 | 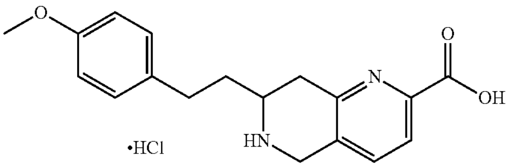 [SMILES: COc1ccc(CCC2Cc3nc(C(=O)O)ccc3CN2)cc1 ; Cl] | MS (ESI) m/z (M + H)$^+$ = 313.2. $^1$H NMR (400 MHz, Deuterium Oxide) δ 7.68 (t, J = 5.5 Hz, 2H), 7.21 (d, J = 8.5 Hz, 2H), 6.98-6.85 (m, 2H), 4.46-4.31 (m, 2H), 3.73 (s, 3H), 3.60 (q, J = 8.4, 7.7 Hz, 1H), 3.32 (dd, J = 18.1, 4.8 Hz, 1H), 3.02 (dd, J = 18.0, 10.8 Hz, 1H), 2.83-2.67 (m, 2H), 2.06 (dt, J = 36.9, 7.8 Hz, 2H). | Referring to Example 45 |
| 43 | 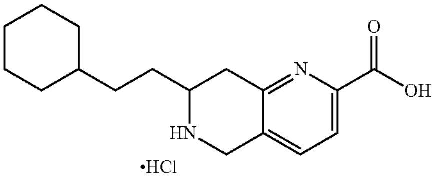 [SMILES: O=C(O)c1ccc2c(n1)CC(CCC1CCCCC1)NC2 ; Cl] | MS (ESI) m/z (M + H)$^+$ = 289.1. $^1$H NMR (400 MHz, Deuterium Oxide) δ 7.67 (s, 2H), 4.39 (s, 2H), 3.66-3.60 (m, 1H), 3.25 (dd, J = 18.1, 4.8 Hz, 1H), 2.94 (dd, J = 18.2, 10.8 Hz, 1H), 1.87-1.43 (m, 7H), 1.36-0.98 (m, 6H), 0.85 (t, J = 12.2 Hz, 2H). | Referring to Example 45 |
| 44 | 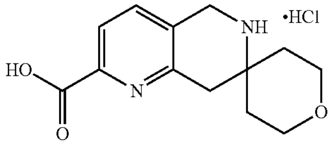 [SMILES: O=C(O)c1ccc2c(n1)CC1(CCOCC1)NC2 ; Cl] | MS (ESI) m/z (M + H)$^+$ = 249.1. $^1$H NMR (400 MHz, Deuterium Oxide) δ 7.96-7.90 (m, 2H), 4.53 (s, 2H), 3.94-3.91 (m, 2H), 3.73-3.67 (t, J = 10.7 Hz, 2H), 3.43 (s, 2H), 2.00-1.86 (m, 4H). | Referring to Example 45 |
| 46 | 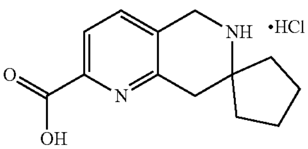 [SMILES: O=C(O)c1ccc2c(n1)CC1(CCCC1)NC2 ; Cl] | MS (ESI) m/z (M + H)$^+$ = 233.1. 1H NMR (400 MHz, Deuterium Oxide) δ 7.85 (s, 1H), 7.74 (d, J = 8.1 Hz, 1H), 4.46 (s, 2H), 3.16 (s, 2H), 1.87-1.71 (m, 8H). | Referring to Example 45 |
| 47 | 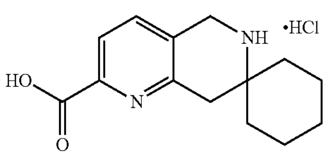 [SMILES: O=C(O)c1ccc2c(n1)CC1(CCCCC1)NC2 ; Cl] | MS (ESI) m/z (M + H)$^+$ = 247.1. $^1$H NMR (400 MHz, Deuterium Oxide) δ 7.86 (s, 2H), 4.43 (s, 2H), 3.20 (s, 2H), 1.74 (m, 2H), 1.64-1.27 (m, 8H). | Referring to Example 45 |
| 48 | 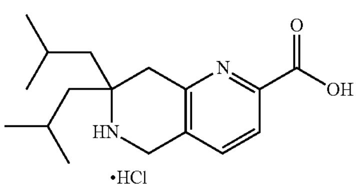 [SMILES: CC(C)CC1(CC(C)C)Cc2nc(C(=O)O)ccc2CN1 ; Cl] | MS (ESI) m/z (M + H)$^+$ = 291.2. $^1$H NMR (400 MHz, Deuterium Oxide) δ 7.69 (d, J = 1.6 Hz, 2H), 4.45-4.34 (m, 2H), 3.19 (d, J = 18.1 Hz, 1H), 3.05 (d, J = 17.9 Hz, 1H), 1.75-1.62 (m, 2H), 1.52 (ddd, J = 28.7, 13.9, 6.6 Hz, 2H), 1.39 (d, J = 9.2 Hz, 3H), 1.11-1.00 (m, 2H), 0.89 (dd, J = 21.7, 6.4 Hz, 3H), 0.81-0.62 (m, 6H). | Referring to Example 45 |
| 49 | 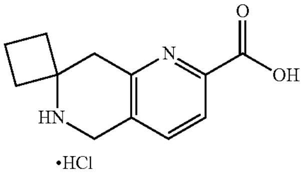 [SMILES: O=C(O)c1ccc2c(n1)CC1(CCC1)NC2 ; Cl] | MS (ESI) m/z (M + H)$^+$ = 219.1. $^1$H NMR (400 MHz, Deuterium Oxide) δ 7.93 (s, 2H), 4.47 (s, 2H), 3.44 (s, 2H), 2.47-2.36 (m, 2H), 2.12-1.90 (m, 4H). | Referring to Example 45 |

Biological Assay

Test Example 1: Plasma Clot Lysis Assay

1. Purpose

To determine the inhibitory effect of the compounds of the invention on the degradation of plasma clots.

2. Experimental Materials and Instruments

| Name(s) | Supplier | Lot number |
|---|---|---|
| Calcium chloride ($CaCl_2$•$2H_2O$) | Shanghai Aladdin Biochemical Technology Co., Ltd | C108383-500g |
| HEPES buffer solution (1M) | Thermo Fisher (Gibco) | 15630-106 |
| Tissue plasminogen activator (tPA) | Sigma-Aldrich | T0831-100UG |
| Human plasma | Provided by healthy volunteers | / |
| $ddH_2O$ | ULUPURE (Sichuan) | UPH-III-20T |
| UV-plate | Corning Inc. (America) | 3635 |
| Tranexamic acid (TXA) | Shanghai Haohong Biopharma Science and Technology Co., Ltd | Lc0701077 |
| Multimode microplate reader | BMG LABTECH | PHERAstar FSX |

3. Experimental Procedure 3.1 Collect fresh healthy human blood, mix 1 part of anticoagulant (0.109 M trisodium citrate) with 9 parts of blood, centrifuge at 2000×g for 20 min at room temperature, collect the supernatant (plasma), sub-package and store at −80° C. for later use.

3.2 On the day of experiment, the plasma was thawed in a water bath at 37° C., and all reagents except tPA were pre-warmed at 37° C.

3.3 Add 12.5 μL of 80 mM $CaCl_2$ (HEPES buffer, pH 7.4) to a 96-well plate, and then add 25 μL of different concentrations of test compound diluted with normal saline, add an equal volume of normal saline to the negative control well.

3.4 Mix 50 μL of pre-warmed plasma with 12.5 μL of 4 nM tPA (HEPES buffer, pH 7.4), immediately add to a 96-well plate, measure the absorbance at 405 nm every 2 minutes, continuously for 15 hours.

3.5 The absorption value changes with time, rising first and then decreasing. The time corresponding to the median of the absorption value in the descending section—the time corresponding to the median of the absorption value in the ascending section is the plasma clot degradation time (Clot lysis time). Taking the plasma clot lysis time of the negative control well as a reference, calculate the relative value of the plasma clot lysis time in the wells treated with different concentrations of the compound and the plasma clot lysis time of the negative control well to obtain the inhibition rate:

Inhibition rate%=(1−Clot lysis time of negative control well/Clot lysis time of compound treated well)×100%

3.6 Fitting the Dose-Response Curve

Taking the log value of the compound concentration as the X-axis, and the percentage inhibition rate as the Y-axis, and dose-response curves were fitted with the software GraphPad Prism 5 by using log (inhibitor) vs. Response-Variable slope to derive $IC_{50}$ values of compounds inhibiting the degradation of plasma clots.

Formula: $Y$=min+(max−min)/(1+10^((Log$IC_{50}$−$X$)×Hillslope).

The inhibitory effect of the compounds of the present invention on plasma clot lysis is determined by the above tests, and the calculated $IC_{50}$ values of the compounds of the present invention are all significantly lower than that of tranexamic acid, a commonly used hemostatic drug in clinical practice. For example, the inhibitory $IC_{50}$ of the compound of Example 1 of the present invention on plasma clot lysis is only ¼ of that of tranexamic acid. The relative coagulation activity of the present invention relative to tranexamic acid in vitro ($IC_{50}$ ratio=$IC_{50\ Examples}$/$IC_{50\ Tranexamic\ acid}$) is shown in the following table:

| Examples | IC50 ratio |
|---|---|
| 1 | 0.25 |
| 2 | 1.24 |
| 3 | 2.89 |
| 4 | / |
| 5 | 0.29 |
| 6 | 0.31 |
| 7 | 0.25 |
| 8 | / |
| 9 | 0.44 |
| 10 | 0.18 |
| 11 | 2.58 |
| 12 | 0.88 |
| 13 | 1.63 |
| 14 | / |
| 15 | 0.57 |
| 16 | 0.54 |
| 17 | 0.34 |
| 18 | 0.66 |
| 19 | 5.75 |
| 20 | 0.50 |
| 21 | 0.14 |
| 22 | 0.67 |
| 23 | 0.17 |
| 24 | 1.67 |
| 25 | 6.36 |
| 26 | 0.22 |
| 27 | 0.67 |
| 28 | 0.27 |
| 29 | 2.26 |
| 30 | 0.32 |
| 31 | 1.87 |
| 32 | 0.61 |
| 33 | 0.53 |
| 34 | 0.11 |
| 35 | 0.12 |
| 36 | 0.13 |
| 37 | 0.18 |
| 38 | 0.13 |
| 39 | 0.17 |
| 40 | 0.18 |
| 41 | 0.12 |
| 42 | 0.17 |
| 43 | 0.11 |
| 44 | 0.23 |
| 45 | 0.57 |
| 46 | 0.33 |
| 47 | 0.40 |
| 48 | 0.42 |
| 49 | 0.28 |

Experimental data shows that the compounds of the present invention can effectively inhibit the degradation of plasma clots, exhibit excellent coagulation and hemostatic activity, and their effective dose is far lower than that of the most frequently used hemostatic drugs in clinical practice, and therefore can effectively avoid adverse reactions and complications caused by high-dose administration, and has an excellent clinical application prospect.

Test Example 2: Monkey PK Experimental Data

1. Animals

Male Cynomolgus monkey, normal grade, 3 monkeys each group (N=3)

2. Pharmaceutical Formulation and Administration

The compound is weighed and dissolved in normal saline to prepare a 0.5 mg/mL clear solution for intravenous administration.

On the day of the experiment, the animals were administered according to the scheme in the table below. At each time point after administration, approximately 1 mL of blood was collected from the forearm vein and placed in heparin sodium anticoagulation tubes. Blood samples were placed on ice after collection, and the plasma was separated by centrifugation within 1 hour (centrifugation conditions: 2200 g, 10 minutes, 2-8° C.). The plasma samples were stored in a refrigerator at −80° C. until analysis.

| Dosage ($mg \cdot kg^{-1}$) | Volume •($mL \cdot kg^{-1}$) | Route of administration | Dosing scheme | Fasting or not | Sample collection time point |
|---|---|---|---|---|---|
| 1 | 2 | Intravenous injection | Single dose | Yes | Before administration, 5, 15 30 min, 1, 2, 4, 8, 24 h after administration |

3. Biological Analysis

The compound concentration in cynomolgus monkey plasma was determined by the following method:

Instruments and equipment: LC-MS/MS-19 (TQ5500, AB SCIEX, USA).

Internal standard: warfarin.

Chromatographic column: ACQUITY UPLC BEH C18, model 1.7 um 2.1*50 mm, purchased from Shenzhen Novah Chemical Technology Co., Ltd.;

Flow rate: 0.60 ml/min.

Column temperature: 40° C.

Mobile phase A: 0.1% formic acid in water.

Mobile phase B: 0.1% formic acid in acetonitrile.

The elution gradient is shown in Table 3.

TABLE 3

| Elution gradient | | |
|---|---|---|
| Time (min) | Mobile phase A (%) | Mobile phase B (%) |
| 0 | 98 | 2 |
| 0.60 | 12 | 88 |
| 1.10 | 12 | 88 |
| 1.11 | 98 | 2 |
| 1.40 | 98 | 2 |

MS detection conditions: electrospray ion source (ESI), positive ion mode, MRM scan.

Take 30 μL of the plasma sample prepared from item "2" , add 300 μL MeOH containing 100 ng/mL of internal standard to precipitate protein. The mixture was vortexed for 1 minute and centrifuged at 18000 g for 7 minutes. The supernatant was transferred to a 96-well plate. Inject 4 μL of supernatant into LC-MS/MS for analysis.

Pharmacokinetic parameters were calculated by using Phoenix WinNonlin7.0 software according to blood concentration data of different time points.

Compounds of the present invention were tested using the above experiments, and the measured pharmacokinetic parameters in cynomolgus monkey are shown in the table below.

| Exp. | Cmax (ng/mL) | AUC (h * ng/mL) | CL (mL/h/kg) |
|---|---|---|---|
| 1 | 10573.5 | 4108.2 | 240 |

Experiments have shown that the compounds of the present invention have the advantages of better hemostatic activity, lower effective dose, and longer duration of drug effect, which can avoid various adverse reactions that may occur in clinical high-dose administration, and therefore improve the safety and efficacy of medication for patients. Moreover, the compounds of the present invention are convenient for preparation and large-scale industrial production, and can effectively reduce the cost of medication. The compounds of the present invention have good distribution, metabolism and excretion properties, the possibility of interaction between drugs is low, and can meet the requirements of pharmacokinetic parameters required for therapeutic effect in human body.

The invention claimed is:

1. A compound represented by the structure of formula I, or a pharmaceutically acceptable salt, isomer, or mixture thereof:

Formula I

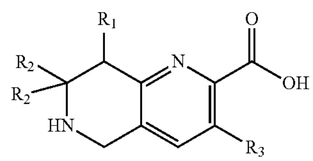

wherein $R_1$ is selected from the group consisting of hydrogen, hydroxy, amino, alkyl, alkoxy, —NH-alkyl, cycloalkyl, aryl, aliphatic heterocyclyl, and aromatic heterocyclyl; wherein said $R_1$ is optionally substituted with 1-2 groups selected from hydroxy, alkyl, arylalkyl, halogen, aryl, and cycloalkyl;

$R_2$ is independently selected from the group consisting of hydrogen, carboxyl, amido, alkyl, —NH-alkyl, —$CH_2$O-alkyl,—$CH_2$NH-alkyl, —COO-alkyl,—CONH-alkyl, cycloalkyl, aryl, aliphatic heterocyclyl, aromatic heterocyclyl, arylalkyl, and cycloalkylalkyl; wherein said $R_2$ is optionally substituted with 1-2 groups selected from hydroxy, alkyl, and alkoxy; or two $R_2$ together with the carbon atom to which they are attached form a cycloalkyl or aliphatic heterocyclyl;

$R_3$ is selected from hydrogen and halogen; and at least one of $R_1$, $R_2$ and $R_3$ is not hydrogen.

2. The compound according to claim 1, or a pharmaceutically acceptable salt, isomer, or mixture thereof, having the structure of formula I':

Formula I'

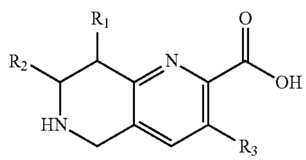

wherein $R_1$ is selected from the group consisting of hydrogen, hydroxy, amino, alkyl, alkoxy, —NH-alkyl, cycloalkyl, aryl, aliphatic heterocyclyl, and aromatic heterocyclyl; wherein said $R_1$ is optionally substituted with 1-2 groups selected from hydroxy, alkyl, halogen, aryl, and cycloalkyl;

$R_2$ is selected from the group consisting of hydrogen, carboxyl, amido, alkyl, —NH-alkyl, —$CH_2$O-alkyl, —$CH_2$NH-alkyl, —COO-alkyl, —CONH-alkyl, cycloalkyl, aryl, aliphatic heterocyclyl, and aromatic heterocyclyl; wherein said $R_2$ is optionally substituted with 1-2 groups selected from hydroxy and alkyl; and $R_3$ is selected from hydrogen and halogen.

3. The compound according to claim 2, or a pharmaceutically acceptable salt, isomer, or mixture thereof, wherein $R_1$ is selected from the group consisting of hydrogen, hydroxy, amino, $C_1$-$C_6$ alkyl, $C_1$-$C_6$ alkoxy, —NH—($C_1$-$C_6$) alkyl, $C_3$-$C_6$ cycloalkyl, 6-to 10-membered aryl, 4-to 10-membered aliphatic heterocyclyl, and 5-to 10-membered aromatic heterocyclyl; and wherein said $R_1$ is optionally substituted with 1-2 groups selected from hydroxy, $C_1$-$C_4$ alkyl, halogen, 6-to 10-membered aryl or aromatic heterocyclyl, and $C_3$-$C_6$ cycloalkyl.

4. The compound according to claim 2, or a pharmaceutically acceptable salt, isomer, or mixture thereof, wherein $R_1$ is selected from the group consisting of hydrogen, hydroxy, amino, phenyl, pyridyl, $C_1$-$C_6$ alkyl, $C_1$-$C_6$ alkoxy, —NH—($C_1$-$C_6$) alkyl, $C_3$-$C_6$ cycloalkyl, and 4-to 7-membered aliphatic heterocyclyl; wherein said R1 is optionally substituted with 1-2 groups selected from hydroxy, $C_1$-$C_4$ alkyl, F, Cl, Br, phenyl, benzyl, and cyclopropyl.

5. The compound according to claim 3, or a pharmaceutically acceptable salt, isomer, or mixture thereof, wherein $R_1$ is selected from the group consisting of hydrogen, hydroxy, amino, phenyl, benzyl, pyridyl, methyl, ethyl, propyl, isopropyl, butyl, methoxy, ethoxy, propoxy, —$NHCH_3$,—$NHCH_2CH_3$,—$NHCH_2CH_2CH_3$, cyclopropyl, cyclobutyl, cyclopentyl, piperidinyl, morpholinyl, piperazinyl, thiomorpholinyl, 1-oxido-4-thiomorpholinyl, and 1,1-dioxido-4-thiomorpholinyl; wherein said $R_1$ is optionally substituted with 1-2 groups selected from hydroxy, F, Cl, Br, methyl, ethyl, propyl, isopropyl, phenyl, benzyl, and cyclopropyl.

6. The compound according to claim 2, or a pharmaceutically acceptable salt, isomer, or mixture thereof, wherein $R_1$ is selected from the group consisting of hydrogen, $C_1$-$C_4$ alkoxy, morpholinyl, piperazinyl, thiomorpholinyl, 1-oxido-4-thiomorpholinyl, and 1,1-dioxido-4-thiomorpholinyl, wherein said $R_1$ is optionally substituted with 1-2 groups selected from hydroxy and benzyl.

7. The compound according to claim 2, or a pharmaceutically acceptable salt, isomer, or mixture thereof, wherein $R_2$ is selected from the group consisting of hydrogen, carboxyl, amido, $C_1$-$C_6$ alkyl, —$CH_2$-O—($C_1$-$C_6$) alkyl, —$CH_2$NH—($C_1$-$C_6$) alkyl, —COO—($C_1$-$C_6$) alkyl, —CONH—($C_1$-$C_6$) alkyl, $C_3$-$C_8$ cycloalkyl, 6-to 10-membered aryl, 4-to 10-membered aliphatic heterocyclyl, and 5-to 10-membered aromatic heterocyclyl; wherein said $R_2$ is optionally substituted with 1-2 groups selected from hydroxy and $C_1$-$C_4$ alkyl.

8. The compound according to claim 7, or a pharmaceutically acceptable salt, isomer, or mixture thereof, wherein $R_2$ is selected from the group consisting of hydrogen, carboxyl, amido, $C_1$-$C_6$ alkyl, —$CH_2$O-($C_1$-$C_6$) alkyl, —$CH_2$NH—($C_1$-$C_6$) alkyl, —COO—($C_1$-$C_6$) alkyl, —CONH—($C_1$-$C_6$) alkyl, $C_3$-$C_6$ cycloalkyl, 6-membered aryl, 4-to 7-membered aliphatic heterocyclyl, and 6-membered aromatic heterocyclyl; wherein said $R_2$ is optionally substituted with 1-2 groups selected from $C_1$-$C_4$alkyl.

9. The compound according to claim 8, or a pharmaceutically acceptable salt, isomer, or mixture thereof, wherein $R_2$ is selected from the group consisting of hydrogen, carboxyl, amido, methyl, ethyl, propyl, isopropyl, n-butyl, t-butyl, pentyl, —$CH_2OCH_3$,—$CH_2OCH_2CH_3$,—$CH_2OCH_2CH_2CH_3$,—$CH_2NHCH_3$,—$CH_2NHCH_2CH_3$,—$CH_2NHCH_2CH_2CH_3$,—$COOCH_3$,—$COOCH_2CH_3$,—$COOCH_2CH_2CH_3$,—$CONHCH_3$,—$CONHCH_2CH_3$,—$CONHCH_2CH_2CH_3$, cyclopropyl, cyclobutyl, cyclopentyl, cyclohexyl, phenyl, benzyl, pyridyl, piperidinyl, morpholinyl, thiomorpholinyl, and 1-oxido-thiomorpholinyl, 1,1-dioxido-4-thiomorpholinyl; wherein said $R_2$ is optionally substituted with 1-2 groups selected from hydroxy, methyl, ethyl, propyl, and isopropyl.

10. The compound according to claim 1, or a pharmaceutically acceptable salt, isomer, or mixture thereof, wherein $R_2$ is independently selected from the group consisting of hydrogen, carboxyl, $C_1$-$C_6$ alkyl, —$CH_2$O—($C_1$-$C_6$) alkyl, —COO—($C_1$-$C_6$) alkyl, $C_3$-$C_6$ cycloalkyl, phenyl-($C_1$-$C_4$) alkyl and ($C_3$-$C_6$) cycloalkyl-($C_1$-$C_4$) alkyl, wherein said alkyl, cycloalkyl and phenyl are optionally substituted with 1-2 groups selected from hydroxy and $C_1$-$C_4$ alkoxy; or two $R_2$ together with the carbon atom to which they are attached form a $C_3$-$C_6$ cycloalkyl or tetrahydropyranyl.

11. The compound according to claim 2, or a pharmaceutically acceptable salt, isomer, or mixture thereof, wherein $R_3$ is selected from hydrogen, fluorine, chlorine and bromine.

12. The compound according to claim 2, or a pharmaceutically acceptable salt, isomer, or mixture thereof, wherein $R_1$ and $R_2$ are not hydrogen simultaneously.

13. The compound according to claim 1, or a pharmaceutically acceptable salt, isomer, or mixture thereof, having the structure:

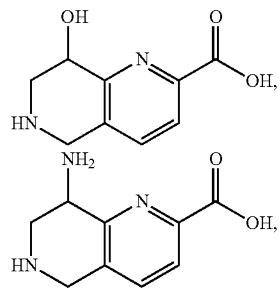

-continued
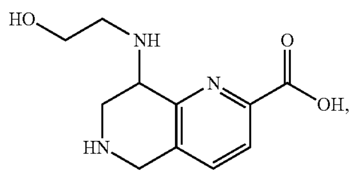
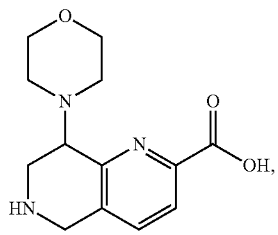
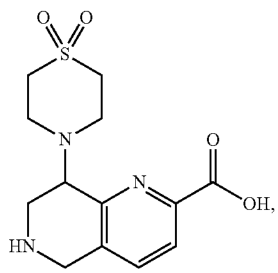
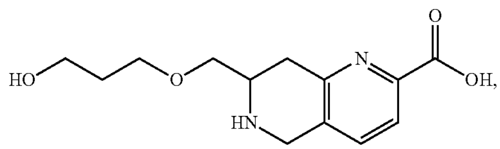
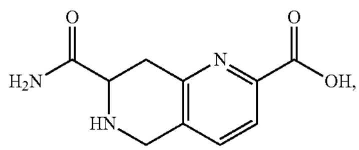
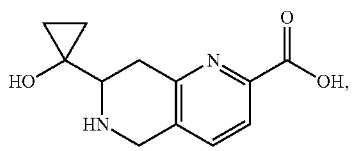
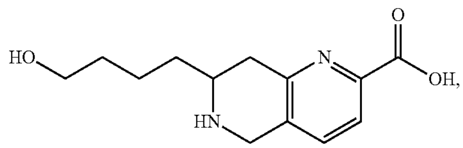
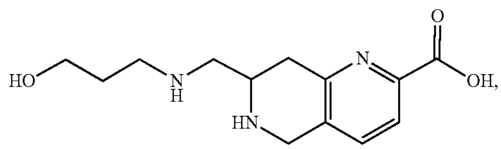
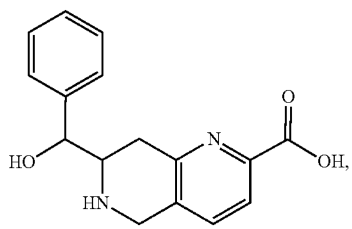
-continued
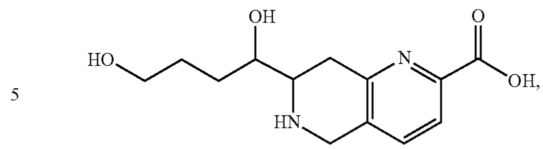
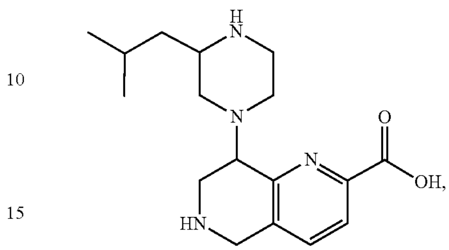
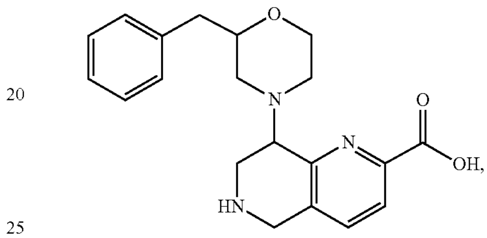
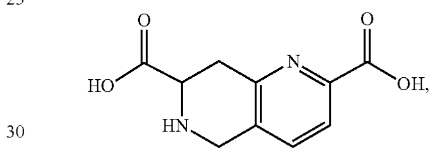
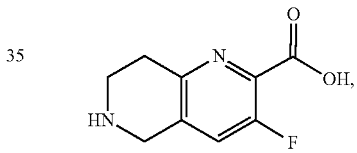
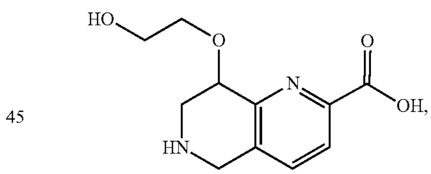
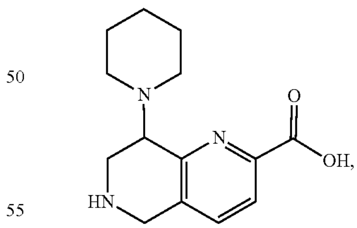
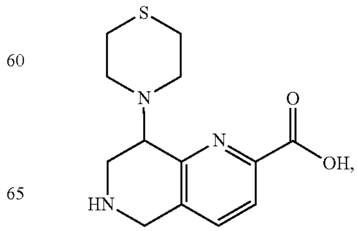

-continued
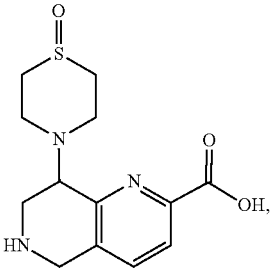
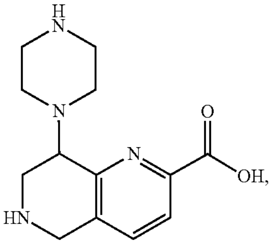
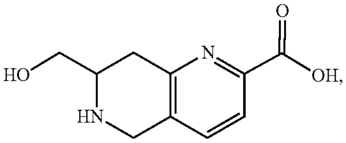
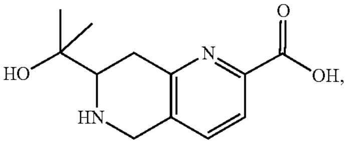
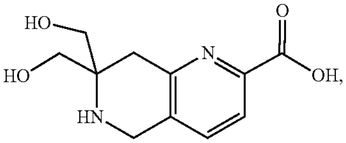
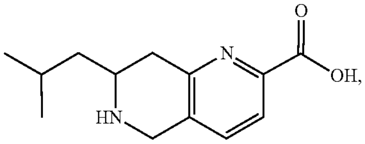
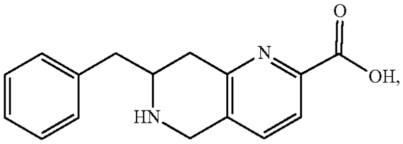
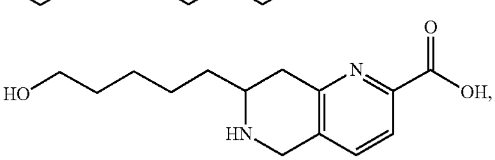
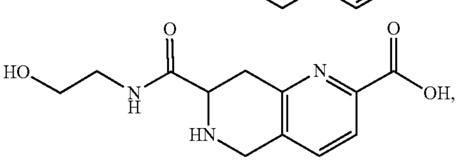
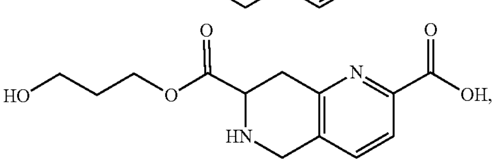
-continued
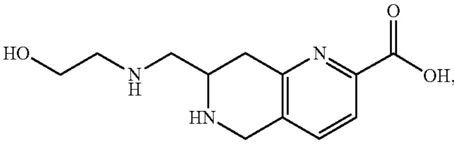
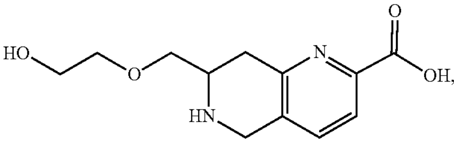
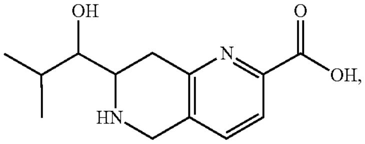
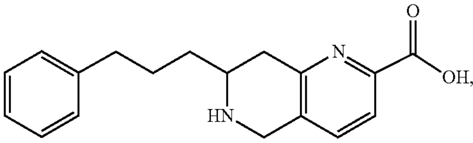
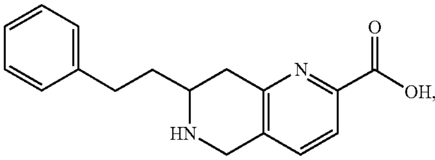
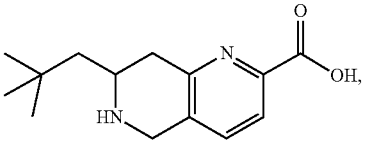
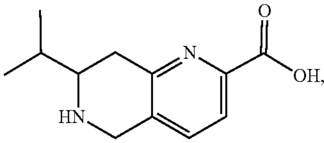
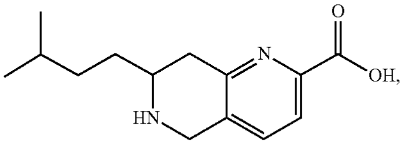
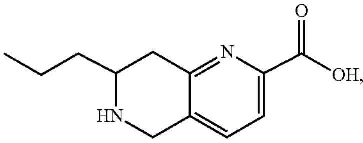
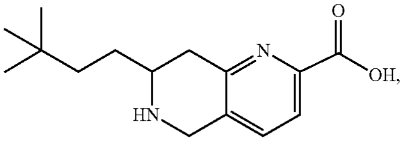
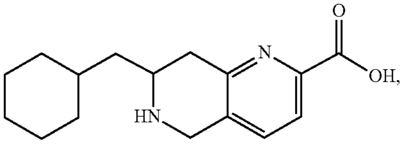

-continued

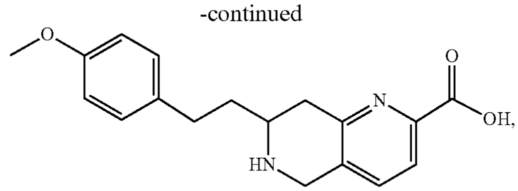

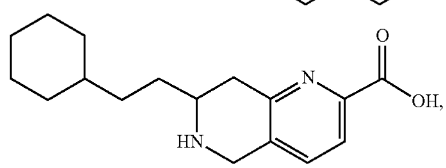

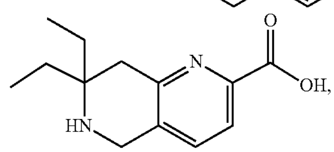

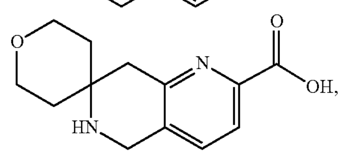

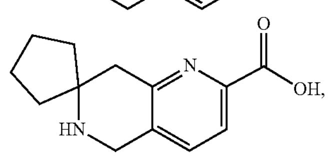

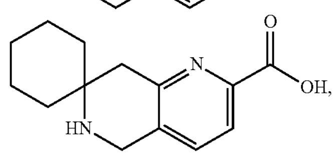

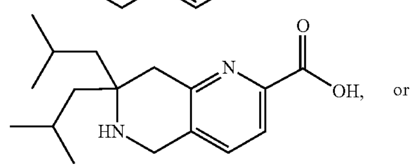

or

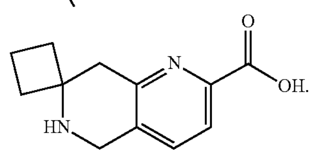

14. A pharmaceutical composition comprising at least one compound according to claim 1, or a pharmaceutically acceptable salt, isomer, or mixture thereof, and at least one pharmaceutically acceptable excipient.

15. A method of treating and/or alleviating bleeding diseases or conditions, comprising administering to a patient in need thereof one or more compounds of formula I according to claim 1, or a pharmaceutically acceptable salt, isomer, or mixture thereof.

16. The method according to claim 15, wherein said bleeding diseases or conditions is selected from abnormal bleeding caused by hyperfibrinolysis, surgical and post-operative bleeding.

17. A method of treating and/or alleviating bleeding diseases or conditions, comprising administering to a patient in need thereof one or more compounds according to claim 13, or a pharmaceutically acceptable salt, isomer, or mixture thereof.

18. The method according to claim 17, wherein said bleeding diseases or conditions is selected from abnormal bleeding caused by hyperfibrinolysis, surgical and post-operative bleeding.

19. The compound according to claim 10, or a pharmaceutically acceptable salt, isomer, or mixture thereof, wherein $R_1$ is selected from the group consisting of hydrogen, $C_1$-$C_4$ alkoxy, morpholinyl, piperazinyl, thiomorpholinyl, 1-oxido-4-thiomorpholinyl, and 1,1-dioxido-4-thiomorpholinyl, wherein said $R_1$ is optionally substituted with 1-2 groups selected from hydroxy and benzyl.

20. A method of treating and/or alleviating bleeding diseases or conditions, comprising administering to a patient in need thereof a compound represented by the following structure, or a pharmaceutically acceptable salt, isomer or mixture thereof;

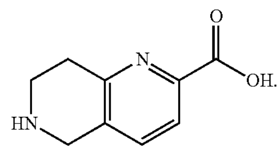 [SMILES: O=C(O)c1ccc2c(n1)CCNC2]

21. The method according to claim 20, wherein said bleeding diseases or conditions is selected from abnormal bleeding caused by hyperfibrinolysis, surgical and post-operative bleeding.

* * * * *